(12) United States Patent
Fry et al.

(10) Patent No.: US 8,778,843 B1
(45) Date of Patent: Jul. 15, 2014

(54) SEMI-PAN-PROTOZOAL BY QUANTITATIVE PCR

(71) Applicants: Stephen E. Fry, Scottsdale, AZ (US); Jeremy Ellis, Mesa, AZ (US)

(72) Inventors: Stephen E. Fry, Scottsdale, AZ (US); Jeremy Ellis, Mesa, AZ (US)

(73) Assignee: Fry Laboratories, L.L.C., Scottsdale, AZ (US)

( * ) Notice: Subject to any disclaimer, the term of this patent is extended or adjusted under 35 U.S.C. 154(b) by 0 days.

(21) Appl. No.: 13/834,441

(22) Filed: Mar. 15, 2013

Related U.S. Application Data

(63) Continuation-in-part of application No. 13/566,972, filed on Aug. 3, 2012.

(60) Provisional application No. 61/514,845, filed on Aug. 3, 2011.

(51) Int. Cl.
*C12Q 1/68* (2006.01)
*C12P 19/34* (2006.01)
*G01N 33/68* (2006.01)
*C07H 21/04* (2006.01)

(52) U.S. Cl.
USPC ............. 506/7; 435/6.11; 435/6.15; 435/91.2

(58) Field of Classification Search
USPC ............................................. 506/7
See application file for complete search history.

(56) References Cited

U.S. PATENT DOCUMENTS

| | | | |
|---|---|---|---|
| 4,683,195 A | 7/1987 | Mullis et al. | |
| 4,883,202 A | 11/1989 | Wahl | |
| 5,130,238 A | 7/1992 | Malek et al. | |
| 5,210,015 A | 5/1993 | Gelfand et al. | |
| 5,487,792 A | 1/1996 | King et al. | |
| 5,804,375 A | 9/1998 | Gelfand et al. | |
| 5,925,517 A | 7/1999 | Tyagi et al. | |
| 6,194,454 B1 * | 2/2001 | Dow | 514/522 |
| 6,214,979 B1 | 4/2001 | Gelfand et al. | |
| 8,114,601 B2 * | 2/2012 | Bergeron et al. | 435/6.12 |
| 2010/0233766 A1 * | 9/2010 | Igarashi et al. | 435/126 |

FOREIGN PATENT DOCUMENTS

CN     101092646 A * 12/2007 ............... C12Q 1/68

OTHER PUBLICATIONS

Guy et al., Applied Environmental Microbiology, Sep. 2003, pp. 5178-5185.*
Hardick et al., Journal of Clinical Microbiology, Nov. 2006, vol. 44, No. 11, pp. 4197-4199.*
Odongo et al., Parasitology Research, Jan. 2010, 106(2), pp. 357-365.*
Ogden et al., Veterinary Parasitology, 112 (2003), pp. 177-183.*

* cited by examiner

*Primary Examiner* — Larry Riggs
*Assistant Examiner* — Karla Dines
(74) *Attorney, Agent, or Firm* — Snell & Wilmer L.L.P.

(57) ABSTRACT

Disclosed are compositions, kits, and methods for detecting, extracting, visualizing, and identifying a pathogenic protozoan. Quantitative real time polymerase chain reaction in connection with specifically designed oligonucleotide probes are used to detect a variety of pathogenic protozoans in patient samples.

12 Claims, 39 Drawing Sheets

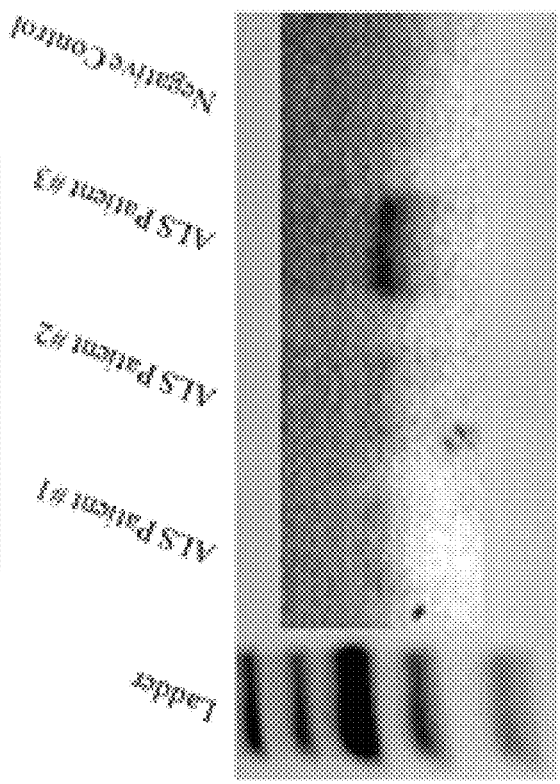
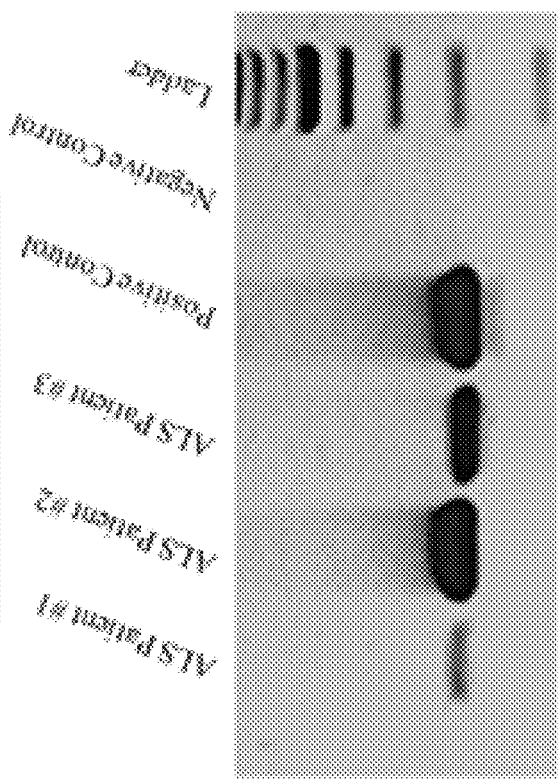
FIG. 4

| Probes | Fluorophore | 16S_Probe | Pmyx_Clade_A1 | Pmyx_Clade_B1 | Pmyx_Clade_C2 | Pmyx_Clade_D1 | Pmyx_Clade_E1 | Pmyx_Clade_E2 | Pmyx_Clade_E3 | Pmyx_Clade_F1 | Pmyx_Clade_G1 | Pmyx_Clade_H1 |
|---|---|---|---|---|---|---|---|---|---|---|---|---|
| 16S_Probe | FAM | x | - | - | - | - | - | - | - | - | - | - |
| Pmyx_Clade_A1 | ROX | o | x | - | - | - | - | - | - | - | - | - |
| Pmyx_Clade_B1 | HEX | o | - | x | - | - | - | - | - | - | - | - |
| Pmyx_Clade_C2 | Cy3 | o | - | - | x | - | - | - | - | - | - | - |
| Pmyx_Clade_D1 | Cy3 | x | - | - | - | x | - | - | - | - | - | - |
| Pmyx_Clade_E1 | FAM | o | - | - | - | - | x | - | - | - | - | - |
| Pmyx_Clade_E2 | Cy5 | o | - | - | - | - | o | x | - | - | - | - |
| Pmyx_Clade_E3 | Cy5 | o | - | - | - | - | o | o | x | - | - | - |
| Pmyx_Clade_F1 | FAM | x | - | - | - | - | - | - | - | x | - | - |
| Pmyx_Clade_G1 | Cy5 | o | - | - | - | - | - | - | - | - | x | - |
| Pmyx_Clade_H1 | Cy5 | o | - | - | - | - | - | - | - | - | - | x |

A

| Fluorophore | 1 | 2 | 3 | 4 |
|---|---|---|---|---|
| FAM | 16S_Probe | Pmyx_Clade_E1 | Pmyx_Clade_E2 | Pmyx_Clade_G1 |
| ROX | Pmyx_Clade_A1 | - | - | - |
| HEX | Pmyx_Clade_B1 | - | - | - |
| Cy3 | - | Pmyx_Clade_C2 | Pmyx_Clade_E3 | - |
| Cy5 | - | Pmyx_Clade_F1 | Pmyx_Clade_D1 | Pmyx_Clade_H1 |

| Sample | 166 | A1 | B1 | C2 | D1 | E1 | E2 | E3 | F1 | G1 | H1 | B-Actin |
|---|---|---|---|---|---|---|---|---|---|---|---|---|
| FL-A | NoCt | 38.21 | 40.10 | NoCt | NoCt | NoCt | NoCt | NoCt | NoCt | 46.02 | 49.38 | 31.77 |
| FL-B | NoCt | 43.63 | NoCt | NoCt | NoCt | 42.42 | NoCt | NoCt | 42.49 | NoCt | 39.57 | 25.38 |
| +Ctrl | 37.70 | 37.90 | 48.98 | NoCt | NoCt | NoCt | NoCt | NoCt | NoCt | NoCt | 36.34 | 28.88 |
| -Ctrl | NoCt | NoCt | NoCt | NoCt | NoCt | NoCt | NoCt | NoCt | NoCt | NoCt | NoCt | NoCt |
| Ct Value | 500.00 | 526.46 | 375.00 | 175.00 | 175.00 | 500.00 | 500.00 | 588.29 | 588.29 | 500.00 | 588.29 | 375.00 |

FIG. 8

SEMI-PAN-PROTOZOAL BY QUANTITATIVE PCR

CROSS REFERENCE TO RELATED APPLICATION

The present application claims priority to and is a Continuation-In-Part of U.S. patent application Ser. No. 13/566,972, filed Aug. 3, 2012, which claims the benefit of the earlier U.S. Provisional Patent Application Ser. No. 61/514,845, filed Aug. 3, 2011. Each of the foregoing applications is hereby incorporated by reference in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,897 byte ASCII (text) file named "1041_034_Sequence_Listing" created on Mar. 1, 2013.

TECHNICAL FIELD

The present disclosure relates to the field of medical diagnostics and specifically, to clinical assays and kits for the detection of pathogenic protozoa.

BACKGROUND

This document relates to compositions and methods for detecting, extracting, visualizing, and identifying pathogenic protozoa.

Various ailments including rheumatic and inflammatory diseases have had a long history of links with infectious agents ranging from molecular mimicry effects to the direct activity of human pathogens.

SUMMARY

The present disclosure is directed to a number of clinical assays to detect DNA segments in pathogenic protozoa including a novel group knows as *Protomyxzoa*. In addition, there are at least ten other "clades" or groups of protozoans that may be identified by the methods and compositions of the present disclosure. *Protomyxzoa* spp. and other newly discovered protozoans are currently under intense scientific study, and initial data suggests they may be a critical lynch pin in a variety of chronic and neurologic illnesses that have some aspects that suggest an infectious process may be involved.

In one aspect, the clinical assays may utilize standard PCR methods, a single probe based assay, and is reproducible from sample to sample. In another aspect, the clinical assays may be expanded to a multiplex (for example, eleven probes) assay to survey a complete suite of newly discovered protozoal sequences. The disclosed multiplex assays use inclusive primer pairs that include, but extend beyond the window of surveillance of a standard PCR method with the addition of several more sequence specific fluorescently labeled probes. As these protozoal organisms were only recently discovered via next generation sequencing methods, no serology or alternative methods of detection exist at this time.

Another aspect of this disclosure relates to a method for determining whether a sample contains or has an increased likelihood of containing a pathogenic protozoan comprising:
a) providing a vessel containing a reaction mixture, wherein the reaction mixture comprises at least one forward primer comprising CCATGCATGTCTAAGTATAAGC (SEQ ID NO: 6), at least one reverse primer comprising CAGAAACTTGAATGATCTATCG (SEQ ID NO: 7), and a nucleic acid target from the sample; wherein the reaction mixture is capable of amplifying, by a polymerase chain reaction (PCR), a segment of the nucleic acid target to produce an amplicon; and wherein production of the amplicon is primed by the at least one forward primer and the at least one reverse primer;
b) incubating the vessel under conditions allowing production of the amplicon if the sample contains the pathogenic protozoan; and
c) determining that the sample contains the pathogenic protozoan or that the sample has an increased likelihood of containing the pathogenic protozoan if the amplicon is detected, or determining that the sample does not contain the pathogenic protozoan or that the sample does not have an increased likelihood of containing the pathogenic protozoan if the amplicon is not detected.

The method may further comprise (d) detecting fluorescence from the oligonucleotide probe in the reaction mixture; and (e) identifying the pathogenic protozoan using an alignment of a sequence of the oligonucleotide probe with a genomic sequence from the pathogenic protozoan.

In some embodiments, the alignment indicates at least 30%, at least 40%, at least 50%, at least 60%, at least 70%, at least 80%, at least 85%, at least 90%, or at least 95% identity between the sequence of the oligonucleotide probe and the genomic sequence. The alignment may indicate 100% identity between the sequence of the oligonucleotide probe and the genomic sequence. Alignment of the oligonucleotide probes of the present invention and known protozoal genomic sequences are shown in FIG. 9-18.

The sample may be an extracted sample obtained by an Expanded Extraction Method or a Combined Sample Enrichment and Expanded Extraction Method as described below.

The method of the present disclosure may involve multiplex quantitative real time PCR (qPCR) with an oligonucleotide probe comprising a fluorophore and/or a quencher.

The present disclosure is also directed to a diagnostic kit used to determine whether a sample contains or has an increased likelihood of containing a pathogenic protozoan comprising:
at least one forward primer comprising SEQ ID NO: 6 and at least one reverse primer comprising SEQ ID NO: 7;
an indication of a result of the presence of a nucleic acid from a pathogenic protozoan;
instructions for using the kit.

The kit may utilize multiplex quantitative real time PCR (qPCR) and further comprise at least one oligonucleotide probe comprising a fluorophore and/or a quencher.

The foregoing and other aspects, features, and advantages will be apparent to those of ordinary skill in the art from the DESCRIPTION and DRAWINGS, and from the CLAIMS.

BRIEF DESCRIPTION OF THE DRAWINGS

Implementations will hereinafter be described in conjunction with the appended DRAWINGS, where any like designations denote like elements.

FIG. 4 show the gel results for a detection study revealing a mixed population of organisms, including Proteobacteria (primarily *Ralstonia* spp.), fungi, and sequences suggestive of a novel protozoan species *Protomyxzoa rheumatica*.

FIG. 7A shows the compatibility in multiplex reactions of the following probes: 166_Probe (aka FL1953_PROBE), (FAM), (SEQ ID NO: 4); Pmyx_Clade_A1, (ROX), (SEQ ID NO: 8); Pmyx_Clade_B1, (HEX), (SEQ ID NO: 9); Pmyx_Clade_C2, (Cy3), (SEQ ID NO: 10); Pmyx_Clade_D1, (Cy3), (SEQ ID NO: 11); Pmyx_Clade_E1, (FAM), (SEQ ID NO: 12); Pmyx_Clade_E2, (FAM), (SEQ ID NO: 13); Pmyx_Clade_E3, (Cy5), (SEQ ID NO: 14); Pmyx_Clade_F1, (Cy5), (SEQ ID NO: 15); Pmyx_Clade_G1, (Cy5), (SEQ ID NO: 16); and Pmyx_Clade_H1, (FAM), (SEQ ID NO: 17). X=compatible; O=incompatible. FIG. 7B shows suggested pools of the probes listed in FIG. 7A for use in multiplex reactions.

FIG. 8 depicts the results of a qPCR assay with two patient samples (FL-A and FL-B) and a positive and negative control ("+Ctrl" and "−Ctrl", respectively) using the probes shown if FIG. 7. "NoCt" indicates a lack of fluorescence above background. The values in each sample row are indicative of the number of cycles at which each reaction reached the threshold cycle ($C_t$). The $C_t$ values used for each probe are indicated in the bottom row.

DETAILED DESCRIPTION

Figure 1:
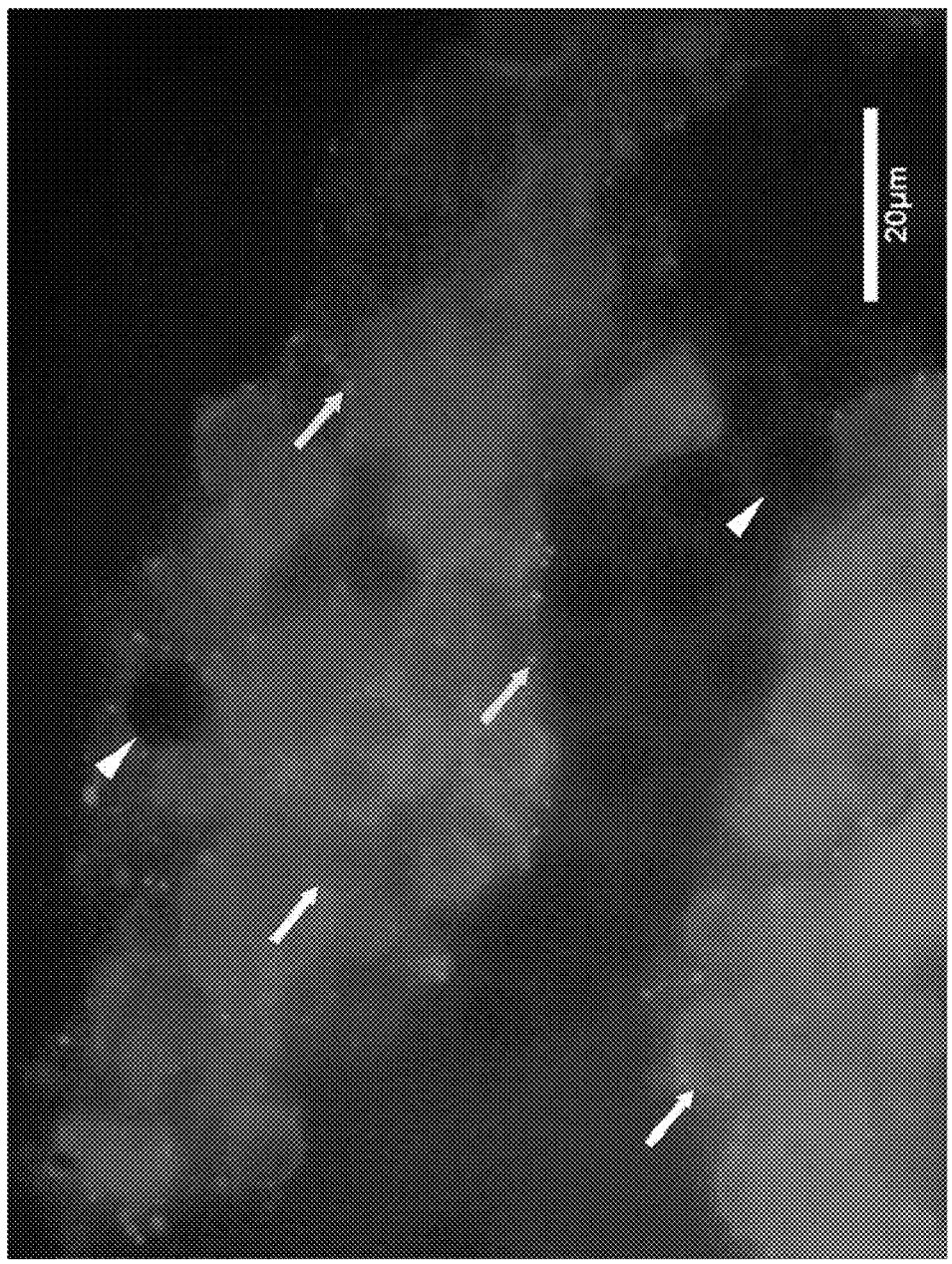
FIG. 1 is a dual Dual Höechst and EtBr DNA stain (1000×) revealing large amorphous clusters, 20-100 μm in diameter, including bacteria (yellow arrows) and organisms, *Protomyxzoa rheumatica*, (white arrows) with varying dye permeability, and red blood cells (arrow heads).

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage. Nucleotides may also be identified as indicated as shown below in Table 1.

TABLE 1

List of Nucleotide Abbreviations

| Symbol | Meaning | Origin of designation |
| --- | --- | --- |
| A | A | adenine |
| G | G | guanine |
| C | C | cytosine |
| T | T | thymine |
| U | U | uracil |
| R | G or A | purine |
| Y | T/U or C | pyrimidine |
| M | A or C | amino |
| K | G or T/U | keto |
| S | G or C | strong interactions 3H-bonds |
| W | A or T/U | weak interactions 2H-bonds |
| B | G or C or T/U | not a |
| D | A or G or T/U | not c |
| H | A or C or T/U | not g |
| V | A or G or C | not t, not u |
| N | A or G or C or T/U, unknown, or other | any |

The term "pathogenic protozoa" as used herein refers to unicellular eukaryotic organisms that are known or suspected to contribute to human disease.

The majority of genes act by specifying polypeptide chains that form proteins. Proteins in turn make up living matter and catalyze all cellular processes.

Chemically, a genome is composed of deoxy-ribonucleic acid ("DNA"). Each DNA molecule is made up of repeating units of four nucleotide bases—adenine ("A"), thymine ("T"), cytosine ("C"), and guanine ("G")—which are covalently linked, or bonded, together via a sugar-phosphate, or phosphodiester, backbone. DNA generally exists as two DNA strands intertwined as a double helix in which each base on a strand pairs, or hybridizes, with a complementary base on the other strand: A pairs with T, and C with G.

The linear order of nucleotide bases in a DNA molecule is referred to as its "sequence." The sequence of a gene is thus denoted by a linear sequence of As, Ts, Gs, and Cs. "DNA sequencing" or "gene sequencing" refers to the process by which the precise linear order of nucleotides in a DNA segment or gene is determined. A gene's nucleotide sequence in turn encodes for a linear sequence of amino acids that comprise the protein encoded by the gene. Most genes have both "exon" and "intron" sequences. Exons are DNA segments that are necessary for the creation of a protein, i.e., that code for a protein. Introns are segments of DNA interspersed between the exons that, unlike exons, do not code for a protein.

The creation of a protein from a gene comprises two steps: transcription and translation. First, the gene sequence is "transcribed" into a different nucleic acid called ribonucleic acid ("RNA"). RNA has a chemically different sugar-phosphate backbone than DNA, and it utilizes the nucleotide base uracil ("U") in place of thymine ("T"). For transcription, the DNA double helix is unwound and each nucleotide on the non-coding, or template, DNA strand is used to make a complementary RNA molecule of the coding DNA strand, i.e., adenine on the template DNA strand results in uracil in the RNA molecule, thymine results in adenine, guanine in cytosine, and cytosine in guanine. The resulting "pre-RNA," like the DNA from which it was generated, contains both exon and intron sequences. Next, the introns are physically excised from the pre-RNA molecule, in a process called "splicing," to produce a messenger RNA ("mRNA").

Following transcription, the resulting mRNA is "translated" into the encoded protein. Genes, and their corresponding mRNAs, encode proteins via three-nucleotide combinations called codons. Each codon corresponds to one of the twenty amino acids that make up all proteins or a "stop" signal that terminates protein translation. For example, the codon adenine-thymine-guanine (ATG, or UTG in the corresponding mRNA), encodes the amino acid methionine. The relationship between the sixty-four possible codon sequences and their corresponding amino acids is known as the genetic code.

Changes, or mutations, in the sequence of a gene can alter the structure as well as the function of the resulting protein. Small-scale changes include point mutations in which a change to a single nucleotide alters a single amino acid in the encoded protein. For example, a base change in the codon GCU to CGU changes an alanine in the encoded protein to an arginine. Larger scale variations include the deletion, rearrangement, or duplication of larger DNA segments, ranging from several hundreds to over a million nucleotides, and result in the elimination, misplacement, or duplication of an entire gene or genes. While some mutations have little or no effect on processes, others result in disease, or an increased risk of developing a particular disease. DNA sequencing is used in clinical diagnostic testing to determine whether a gene contains mutations associated with a particular disease or risk of a particular disease.

Nearly every cell contains an entire genome. DNA in the cell, called "native" or "genomic" DNA, is packaged into chromosomes. Chromosomes are complex structures of a single DNA molecule wrapped around proteins called histones.

Genomic DNA can be extracted from its cellular environment using a number of well-established laboratory techniques. A particular segment of DNA, such as a gene, can then be excised or amplified from the DNA to obtain the isolated DNA segment of interest. DNA molecules can also be synthesized in the laboratory. One type of synthetic DNA molecule is complementary DNA ("cDNA"). cDNA is synthesized from mRNA using complementary base pairing in a manner analogous to RNA transcription. The process results in a double-stranded DNA molecule with a sequence corresponding to the sequence of an mRNA produced by the body. Because it is synthesized from mRNA, cDNA contains only the exon sequences, and thus none of the intron sequences, from a native gene sequence.

An oligonucleotide is a short segment of RNA or DNA, typically comprising approximately thirty or fewer nucleotide bases. Oligonucleotides may be formed by the cleavage or division of longer RNA/DNA segments, or may by synthesized by polymerizing individual nucleotide precursors, such as by polymerase chain reaction (PCR) and/or other known techniques. Automated synthesis techniques such as PCR may allow the synthesis of oligonucleotides up to 160 to 200 nucleotide bases. With respect to PCR, an oligonucleotide is commonly referred to as a "primer," which allows DNA polymerase to extend the oligonucleotide and replicate the complementary strand. The length of an oligonucleotide is typically denoted in terms of "mer." By way of non-limiting example, an oligonucleotide having 25 nucleotide bases would be characterized as a 25-mer oligonucleotide. Because oligonucleotides readily bind to their respective complementary nucleotide, they may used as probes for detecting particular DNA or RNA. The oligonucleotides can be made with standard molecular biology techniques known in the art and disclosed in manuals such as Sambrook et al., Molecular Cloning: A Laboratory Manual, Cold Spring Harbor Laboratory Press, Cold Spring Harbor, N.Y., USA (1989) or conventional nucleotide phosphoramidite chemistry and commercially available synthesizer instruments. The oligonucleotides can be DNA or RNA. Also contemplated are the RNA equivalents of the oligonucleotides and their complements.

The term "primer" refers to an isolated single stranded oligonucleotide sequence capable of acting as a point of initiation for synthesis of a primer extension product, which is complementary to the nucleic acid strand to be copied. The length and the sequence of the primer must be such that they allow to prime the synthesis of the extension products. A primer is about 5-50 nucleotides long, more specifically from 10 to 40 nucleotides long. Specific length and sequence will depend on the complexity of the required DNA or RNA targets, as well as on the conditions of primer use such as temperature and ionic strength.

As used herein, the terms "quantitative real time polymerase chain reaction," "real-time polymerase chain reaction," and "qPCR" are synonymous and refer to a laboratory technique based on a polymerase chain reaction used to amplify and simultaneously quantify a targeted DNA molecule. Frequently, real-time PCR is combined with reverse transcription to quantify messenger RNA and non-coding RNA in cells or tissues.

The oligonucleotides used as primers or probes may also comprise nucleotide analogues such as phosphorothiates, alkylphosphorothiates or peptide nucleic acids or may contain intercalating agents.

As most other variations or modifications introduced into the original DNA sequences, these variations will necessitate adaptions with respect to the conditions under which the oligonucleotide should be used to obtain the required specificity and sensitivity. However the eventual results of hybridization will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The two main pan-genus polymerase chain reaction (PCR) based detection methods may be used to survey the presence of rare and/or unknown variants of organisms. Both PCR assays have distinct advantages and disadvantages that differ from both a scientist and clinician perspective.

First, traditional PCR based detection methods utilize specific primers to amplify identifying sequences of an organism. Amplified products are visualized via gel electrophoresis and bands that are within a certain size range can be further analyzed by restriction enzyme digest or by sequence analysis. This approach has significant advantages due to the flexibility in choices of primer design. Primers can be designed intentionally to amplify entire groups of related organisms and the stringency can be controlled by altering the primer positions, primer degeneracy, and primer annealing temperatures. Having the flexibility to make few assumptions about the target organism could provide detection of rare or novel species, thus providing immediate benefit to clinicians and their patients.

However, this method is not without some weaknesses. Moderate stringency PCRs produces some potential positives that, upon sequence analysis, are identified as artifacts, which give the false appearance of a positive PCR signal. Therefore, effort spent on sequencing these false bands was wasted. Furthermore, the fact that this method intentionally is of moderate stringency opposes finely tuned and optimized detection levels. Other PCR based methods could allow exceptionally sensitive detection down to even a single organismal genome in an entire patient sample. Thus far, it appears as if clinicians are willing to accept some loss of sensitivity for the increased chance at detecting rare or novel species.

Second, a newer PCR based detection technique utilizes quantitative PCR (qPCR) that uses either fluorescently labeled nucleotides or probes to spectroscopically measure the levels of amplified product. This technique requires highly optimized and stringent probes, thus reducing the probability of pan-genus detection. However, qPCR is sensitive enough to detect exceptionally low copy numbers of the organismal genome.

The term "probe" refers to isolated single stranded sequence-specific oligonucleotides, which have a sequence that is complementary to the target sequence to be detected. Complementarity of the probe sequence to the target sequence is essential and complete for the central part of the probe (=core of the probe), where no mismatches to the target sequence are allowed. Towards the extremities (3' or 5') of the probe, minor variations in the probe sequence may sometimes occur, without affecting the species specific hybridization behavior of the probe. The "core sequence" of the probe is the central part, and represents more than 70%, more than 80%, most often more than 90% of the total probe sequence.

The probes disclosed herein specifically hybridize to nucleic acids from pathogenic protozoa for which they are designed. Throughout this document, the sequences of the probes are always represented from the 5' end to the 3' end. They are represented as single stranded DNA molecules. It should be understood however that these probes may also be used in their RNA form (wherein T is replaced by U), or in their complementary form.

Probes may be formed by cloning of recombinant plasmids containing inserts comprising the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phospho-triester method.

Some of the probes disclosed herein have a length from about 10 to about 30 nucleotides. Variations are possible in the length of the probes and it should be clear that, since the central part of the probe is essential for its hybridization characteristics, possible deviations of the probe sequence versus the target sequence may be allowable towards head and tail of the probe, especially when longer probe sequences are used. These variant probes, should however always be evaluated experimentally, in order to check if they result in equivalent hybridization characteristics than the original probes.

The term "isolated" as used herein means that the oligonucleotides disclosed herein are isolated from the environment in which they naturally occur. In particular, it means that they are not an % more part of the genome of the respective species, and thus liberated from the remaining flanking nucleotides in the target region of the species. On the contrary, new (=heterologous) flanking regions may be added to the 3' and/or 5' end of the probe, in order to enhance its functionality. Functional characteristics possibly provided by said heterologous flanking sequences are e.g. ease of attachment to a solid support, ease of synthesis, ease of purification, labeling function etc.

The term "complementary" nucleic acid as used herein means that the nucleic acid sequences can form a perfect base-paired double helix with each other.

The term "specific hybridization" refers to a selective hybridization of the probes disclosed herein to the nucleic acids of a pathogenic protozoan to be detected (=target organism), and not to nucleic acids originating from strains belonging to other species (=non-target organisms). Specific hybridization in the context of the present disclosure also implies a selective hybridization of the disclosed probes to the target region of a pathogenic protozoan to be detected, and limits occasional "random" hybridization to other genomic sequences. Specificity is a feature which has to be experimentally determined. Although it may sometimes be theoretically predictable, specificity can only refer to those non-target organisms which have been tested experimentally.

The term "sample" represents any material possibly containing nucleic acids, which may have to be released from the cells. Preferably, the term "sample" refers to a clinical sample, such as a sample taken from blood, from the respiratory tract (sputum, bronchoalveolar lavage (BAL)), from cerebrospinal fluid (CSF), from the urogenital tract (vaginal secretions, urine), from the gastrointestinal tract (saliva, feces) or biopsies taken from organs, tissue, skin, teeth, bone, etc. The term "sample" may also refer to a sample of cultured cells, either cultured in liquid medium or on solid growth media. DNA present in said samples may be prepared or extracted according to any of the techniques known in the art.

The "target" material in these samples may be either genomic DNA or precursor ribosomal RNA of the organism to be detected (=target organism), or amplified versions thereof. These molecules are called target nucleic acids.

The term "isolated" oligonucleotide refers to an oligonucleotide that is found in a condition other than its native environment. In a preferred form, the oligonucleotide is substantially free from other nucleic acid sequences, such as other chromosomal and extrachromosomal DNA and RNA, that normally accompany or interact with it as found in its naturally occurring environment. The term "isolated" oligonucleotide also embraces recombinant oligonucleotides and chemically synthesized oligonucleotides.

The term "sample" as used herein, means anything designated for testing for the presence of an organism and/or the nucleic acid of an organism. The test sample is, or can be derived from any biological source, such as for example, blood, blood plasma, cell cultures, tissues and mosquito samples. The test sample can be used directly as obtained from the source, or following a pre-treatment to modify the character of the sample. Thus, the test sample can be pre-treated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, and purifying nucleic acid.

A large number of protozoal pathogens are known. The methods and kits of the present disclosure may be used to detect a pathogenic protozoan selected, from the group consisting of *Protomyxzoa* spp., *Sarcocystis* spp., *Cyclophora* spp., *Eimeria* spp., *Goussia* spp., *Entamoeba histolytica*, *Acanthamoeba castellanii*, *Balamuthia mandrillaris*, *Trichomonas* spp., *Thpanosoma* spp., *Leishmania* spp., *Pneumocystis pneumonia*, *Naegleria fowleri*, *Giardia intestinalis*, *Blastocystis hominis*, *Babesia microti*, *Cryptosporidium* spp., *Cyclospora cayetanensis*, *Toxoplasma gondii*, an *Theileria* spp. The *Protomyxzoa* spp. may be *Protomyxzoa rheumatica*. The *Cryptosporidium* spp. may be *Cryptosporidium parvum*, *Cryptosporidium hominis*, *Cryptosporidium canis*, *Cryptosporidium felis*, *Cryptosporidium meleagridis*, or *Cryptosporidium muris*. The *Trichomonas* spp. may be *Trichomonas tenas*, *Trichomonas hominis*, or *Trichomonas vaginalis*. The *Trypanosoma* spp. may be *Trypanosoma gambiense*, *Trypanosoma rhodesiense*, *Trypanosoma cruzi* and *Trypanosoma brucei*. The *Leishmania* spp. may be *Leishmania donovani*, *Leishmania tropica*, or *Leishmania braziliensis*. The *Theileria* spp. may be *Theileria lawrenci* or *Theileria parva*.

In one aspect of the present disclosure, the pathogenic protozoa belongs to a phylum selected from the group consisting of Euglenozoa (e.g., *Trypanosoma cruzi*, *Trypanosoma brucei*, *Leishmania* spp.); Heterolobosea (e.g., *Naegleria fowler*); Diplomonadida (e.g., *Giardia intestinalis*); Amoebozoa (e.g., *Acanthamoeba castellanii*, *Balamuthia mandrillaris*, *Entamoeba histolytica*); Blastocystis (e.g., *Blastocystis hominis*); Apicomplexa (e.g., *Babesia microti*, *Cryptosporidium parvum*, *Cyclospora cayetanensis*, *Toxoplasma gondii*). See Ecker D J, et al. (2005) "The Microbial Rosetta Stone Database: A compilation of global and emerging infectious microorganisms and bioterrorist threat agents" BMC Microbiol. 5:19.

There are many aspects of compositions and methods for detecting a pathogenic protozoan disclosed herein, of which one, a plurality, or all aspects may be used in any particular implementation.

It is to be understood that various implementations may be utilized, and compositional, as well as procedural, changes may be made without departing from the scope of this document. As a matter of convenience, various compositions and methods will be described using exemplary materials, sizes, specifications, and the like. However, this document is not limited to the stated examples and other configurations are possible and within the teachings of the present disclosure.

Implementations of the disclosed compositions and methods relate generally to oligonucleotides useful in methods for determining whether a sample contains a pathogenic protozoan. Although, any recombinant products such as peptides and the like are within the scope of this disclosure, which could also be used as diagnostics for markers or in immunological testing as antigens.

In one aspect, a pathogenic protozoan may be identified using the following PCR primers:

Primers:

```
Protozoal_F(forward primer)            (SEQ ID NO: 6)
CCATGCATGTCTAAGTATAAGC Protozoal_R (reverse primer)           (SEQ ID NO: 7)
CAGAAACTTGAATGATCTATCG
```

In another aspect, the pathogenic protozoan can be detected with qPCR utilizing any one of the following probes:

```
Pmyx_Clade_A_Probe1 (ROX)                          (SEQ ID NO: 8)
/56-ROXN/GGATAACCGTAGTAATTCTGGAGCTAATACAT/
3IABRQSp/

Pmyx_Clade_B_Probe1 (HEX)                          (SEQ ID NO: 9)
/HEX/TAAACTRTA/ZEN/ACTGWTWTAATGAGCYWTYCGCAGTTTY/
3IABkFQ/

Pmyx_Clade_C_Probe2 (Cy3)                          SEQ ID NO: 10)
/5Cy3/GGAGCTAATACATGATACAGGACCCG/3IAbRQSp/

Pmyx_Clade_D_Probe1 (Cy3)                          (SEQ ID NO: 11)
/5Cy3/GAATGGCTCATTAWAWCAGTTAYAGTTTATTTGATGAT/
3IAbRQSp/

Pmyx_Clade_E_Probe1_(FAM)                          (SEQ ID NO: 12)
/56-FAM/CTACGTGGATAACTGTAGTAATTCTAGAGCTAA/3IABkFQ/

Pmyx_Clade_E_Probe2_(FAM)                          (SEQ ID NO: 13)
/56-FAM/TTATTTGAT/ZEN/GGTTTYYTACTTGGATAACCCGAGT/
3IABkFQ/

Pmyx_Clade_E_Probe3 (Cy5)                          (SEQ ID NO: 14)
/5Cy5/CTCTGGCTAATATACGCTGAAGACC/3IAbRQSp/
```

-continued

Pmyx_Clade_F_Probe1 (Cy5)                    (SEQ ID NO: 15)
/5Cy5/TGGATAACCGYRGTAATWCTRKRGCTAAKACATG/3IAbRQSp/

Pmyx_Clade_G_Probe1 (Cy5)                    (SEQ ID NO: 16)
/5Cy5/GTGAAACTGCGAATGGCTCATTATATCAGTTAT/3IAbRQSp/

Pmyx_Clade_H_Probe1 (FAM)                    (SEQ ID NO: 17)
/56-FAM/WAYDGYGAA/ZEN/ACTGCGAATGGCTCATTAWAWCA/
3IABkFQ/

In another aspect, implementations of the disclosed compositions and methods relate generally to oligonucleotides, recombinant products such as peptides, and the like useful in methods for determining whether a sample contains a pathogenic protozoan, or has an increased likelihood of containing a pathogenic protozoan, which may be seen in conjunction with CFS, Fibromyalgia, the autoimmune diseases, ALS, MS, Parkinson's disease, Autism, and the like.

Isolated oligonucleotides (by way of non-limiting example, a forward primer, a reverse primer, or a probe such as a molecular beacon) are capable of detecting a unique biomarker for the pathogenic protozoan species.

In still another aspect, the present disclosure provides test kits useful for detecting a pathogenic protozoan from a sample that may comprise at least one oligonucleotide disclosed in this document. The test kits may contain one or more pairs of oligonucleotides such as the primer pairs disclosed herein, or one or more oligonucleotide sets as disclosed herein. The assay kit can further comprise the four-deoxynucleotide phosphates (dATP, dGTP, dCTP, dTTP) and an effective amount of a nucleic acid polymerizing enzyme. A number of enzymes are known in the art which are useful as polymerizing agents. These include, but are not limited to E. coli DNA polymerase I, Klenow fragment, bacteriophage T7 RNA polymerase, reverse transcriptase, and polymerases derived from thermophilic bacteria, such as Thermus aquaticus. The latter polymerases are known for their high temperature stability, and include, for example, the Taq DNA polymerase I. Other enzymes such as Ribonuclease H can be included in the assay kit for regenerating the template DNA. Other optional additional components of the kit include, for example, means used to label the probe and/or primer (such as a fluorophore, quencher, chromogen, etc.), and the appropriate buffers for reverse transcription, PCR, or hybridization reactions. The kit may also contain instructions for carrying out the methods.

In yet another aspect, methods useful for detecting a pathogenic protozoan from one or more samples may comprise aligning nucleotide sequences pair wise and determining the percent identities (percentage of identical matches) between universal or specific primers and the sample to be tested. In particular implementations, a reaction mixture or a kit may be provided comprising an isolated oligonucleotide (a forward primer, in particular implementations). In other particular implementations, a second isolated oligonucleotide, different than the first isolated oligonucleotide (a reverse primer, in particular implementations) may be provided. The primers are capable of hybridizing under highly stringent hybridization conditions to a polynucleotide present in the sample.

Methods useful for detecting pathogenic protozoan from one or more samples may further comprise a method for determining whether a sample (by way of non-limiting examples, a blood sample, or other a biological sample, such as a swab specimen) contains a pathogenic protozoan or has an increased likelihood of containing a pathogenic protozoan, wherein the method comprises the following:

a) providing a vessel containing a reaction mixture, wherein the reaction mixture comprises at least one forward primer comprising CCATGCATGTCTAAGTATAAGC (SEQ ID NO: 6), at least one reverse primer comprising CAGAAACTTGAATGATCTATCG (SEQ ID NO: 7), and a nucleic acid target from the sample; wherein the reaction mixture is capable of amplifying, by a polymerase chain reaction (PCR), a segment of the nucleic acid target to produce an amplicon; and wherein production of the amplicon is primed by the at least one forward primer and the at least one reverse primer;

b) incubating the vessel under conditions allowing production of the amplicon if the sample contains the pathogenic protozoan; and c) determining that the sample contains the pathogenic protozoan or that the sample has an increased likelihood of containing the pathogenic protozoan if the amplicon is detected, or determining that the sample does not contain the pathogenic protozoan or that the sample does not have an increased likelihood of containing the pathogenic protozoan if the amplicon is not detected.

Alternatively, in step a) of the method above, the reaction mixture may further comprise an oligonucleotide probe (by way of non-limiting example, a molecular beacon) capable of detecting the amplicon if the amplicon is produced.

Nucleic acids, including oligonucleotide probes, in the methods and compositions described herein may be labeled with a reporter. A reporter is a molecule that facilitates the detection of a molecule to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl] cyclobutenediylium-1,3-dioxolate, an infrared dye such as 2,4Bis[3,3-dimethyl-2-(1H-benz[e]indolinylidenemethyl)] cyclobutenediylium-1,3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red®. A signal amplification reagent, such as tyramide (PerkinElmer), may be used to enhance the fluorescence signal. Indirect reporter molecules include biotin, which must be bound to another molecule such as streptavidin-phycoerythrin for detection. In a multiplex reaction, the reporter attached to the primer or the dNTP may be the same for all reactions in the multiplex reaction if the identities of the amplification products can be determined based on the specific location or identity of the solid support to which they hybridize.

It is also contemplated that fluorophore/quencher-based detection systems may be used with the methods and compositions disclosed herein. When a quencher and fluorophore are in proximity to each other, the quencher quenches the signal produced by the fluorophore. A conformational change in the nucleic acid molecule separates the fluorophore and quencher to allow the fluorophore to emit a fluorescent signal. Fluorophore/quencher-based detection systems reduce background and therefore allow for higher multiplexing of primer sets compared to free floating fluorophore methods, particularly in closed tube and real-time detection systems.

In particular embodiments, molecules useful as quenchers include, but are not limited to tetramethylrhodamine (TAMRA), DABCYL (DABSYL, DABMI or methyl red) anthroquinone, nitrothiazole, nitroimidazole, malachite green, Black Hole Quenchers®, e.g., BHQ1 (Biosearch Technologies), Iowa Black® or ZEN quenchers (from Integrated DNA Technologies, Inc.) (e.g., 3' Iowa Black® RQ-Sp aka 31ABRQSp and 3' Iowa Black® FQ aka 31ABkFQ), TIDE Quencher 2 (TQ2) and TIDE Quencher 3 (TQ3) (from AAT Bioquest).

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Preferably, commercially available linking moieties are employed that can be attached to an oligonucleotide during synthesis, e.g., available from Integrated DNA Technologies (Coralville, Iowa) or Eurofins MWG Operon (Huntsville, Ala.).

Rhodamine and fluorescein dyes are also conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928.

The amplifying step can be performed using any type of nucleic acid template-based method, such as PCR technology.

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions (Mg2+); and monovalent cation potassium ions.

PCR technology relies on thermal strand separation followed by thermal dissociation. During this process, at least one primer per strand, cycling equipment, high reaction temperatures and specific thermostable enzymes are used (U.S. Pat. Nos. 4,683,195 and 4,883,202). Alternatively, it is possible to amplify the DNA at a constant temperature (Nucleic Acids Sequence Based Amplification (NASBA) Kievits, T., et al., J. Virol Methods, 1991; 35, 273-286; and Malek, L. T., U.S. Pat. No. 5,130,238; T7 RNA polymerase-mediated amplification (TMA) (Giachetti C, et al. J Clin Microbiol 2002 July; 40(7):2408-19; or Strand Displacement Amplification (SDA), Walker, G. T. and Schram, J. L., European Patent Application Publication No. 0 500 224 A2; Walker, G. T., et al., Nuc. Acids Res., 1992; 20, 1691-1696).

Thermal cycling subjects the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step—94-96° C.; denaturation step—94-98° C.; annealing step—50-65° C.; extension/elongation step—70-74° C.; final elongation—70-74° C.; final hold—4-10° C.

Real-time polymerase chain reaction, also called quantitative real time polymerase chain reaction (QRT-PCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

Mulitplex-PCR and multiplex real-time PCR may also use unique sets or pools of oligonucleotide probes to detect multiple amplicons at once. In some embodiments, the method of the present invention comprises multiplex quantitative real time PCR (qPCR) with unique pools of oligonucleotide probes. FIG. 7A shows the compatibility of the various probes disclosed herein in multiplex qPCR reactions, and FIG. 7B shows suggested pools of probes. In one embodiment, the reaction mixture in the multiplex qPCR comprises a pool of oligonucleotide probes selected from:
a) SEQ ID NO: 4, SEQ ID NO: 8, and SEQ ID NO: 9;
b) SEQ ID NO: 10, SEQ ID NO: 12, and SEQ ID NO: 15;
c) SEQ ID NO: 11, SEQ ID NO: 13, and SEQ ID NO: 14; and
d) SEQ ID NO: 16 and SEQ ID NO: 17.

The methods disclosed herein may also utilize asymmetric priming techniques during the PCR process, which may enhance the binding of the reporter probes to complimentary target sequences. Asymmetric PCR is carried with an excess of the primer for the chosen strand to preferentially amplify one strand of the DNA template more than the other.

Amplified nucleic acid can be detected using a variety of detection technologies well known in the art. For example, amplification products may be detected using agarose gel by performing electrophoresis with visualization by ethidium bromide staining and exposure to ultraviolet (UV) light, by sequence analysis of the amplification product for confirmation, or hybridization with an oligonucleotide probe.

The oligonucleotide probe may comprise a fluorophore and/or a quencher. The oligonucleotide probe may also contain a detectable label including any molecule or moiety having a property or characteristic that is capable of detection, such as, for example, radioisotopes, fluorophores, chemiluminophores, enzymes, colloidal particles, and fluorescent microparticles.

Probe sequences can be employed using a variety of methodologies to detect amplification products. Generally all such methods employ a step where the probe hybridizes to a strand of an amplification product to form an amplification product/probe hybrid. The hybrid can then be detected using labels on the primer, probe or both the primer and probe. Examples of homogeneous detection platforms for detecting amplification products include the use of FRET (fluorescence resonance energy transfer) labels attached to probes that emit a signal in the presence of the target sequence. "TaqMan" assays described in U.S. Pat. Nos. 5,210,015; 5,804,375; 5,487,792 and 6,214,979 (each of which is herein incorporated by reference) and Molecular Beacon assays described in U.S. Pat. No. 5,925,517 (herein incorporated by reference) are examples of techniques that can be employed to detect nucleic acid sequences. With the "TaqMan" assay format, products of the amplification reaction can be detected as they are formed or in a so-called "real time" manner. As a result, amplification product/probe hybrids are formed and detected while the reaction mixture is under amplification conditions.

For example, the PCR probes may be TaqMan® probes that are labeled at the 5' end with a fluorophore and at the 3'-end with a quencher molecule. Suitable fluorophores and quenchers for use with TaqMan® probes are disclosed in U.S. Pat. Nos. 5,210,015, 5,804,375, 5,487,792 and 6,214,979 and WO 01/86001 (Biosearch Technologies). Quenchers may be Black Hole Quenchers disclosed in WO 01/86001.

Nucleic acid hybridization can be done using techniques and conditions known in the art. Specific hybridization conditions will depend on the type of assay in which hybridization is used. Hybridization techniques and conditions can be found, for example, in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York) and Sambrook et al. (1989) Molecular Cloning. A Laboratory Manual (2d ed., Cold Spring Harbor Laboratory Press, Plainview, N.Y.).

Hybridization of nucleic acid may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified. Alternatively, stringency conditions can be adjusted to allow some mismatching in sequences so that lower degrees of similarity are detected.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30.degree. C. for short probes (e.g., 10 to 50 nucleotides) and at least about 60.degree. C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37.degree. C., and a wash in 1.times. to 2.times.SSC (20.times.SSC=3.0 M NaCl/0.3 M trisodium citrate) at 50 to 55.degree. C. Exemplary moderate stringency conditions include hybridization in 40 to 45% formamide, 1.0 M NaCl, 1% SDS at 37.degree. C., and a wash in 0.5.times. to 1.times.SSC at 55 to 60.degree. C. Exemplary high stringency conditions include hybridization in 50% formamide, 1 M NaCl, 1% SDS at 37.degree. C., and a wash in 0.1.times.SSC at 60 to 65.degree. C. The duration of hybridization is generally less than about 24 hours, usually about 4 to about 12 hours, or less depending on the assay format.

It should be noted that the oligonucleotides of this disclosure can be used as primers or probes, depending on the intended use or assay format. For example, an oligonucleotide used as a primer in one assay can be used as a probe in another assay. The grouping of the oligonucleotides into primer pairs and primer/probe sets reflects certain implementations only. However, the use of other primer pairs comprised of forward and reverse primers selected from different preferred primer pairs is specifically contemplated.

Quantitative Real-Time PCR (qPCR) Detection Chemistries

There are several commercially available nucleic acid detection chemistries currently used in qPCR. These chemistries include DNA binding agents, FRET based nucleic acid detection, hybridization probes, molecular beacons, hydrolysis probes, and dye-primer based systems. Each of these chemistries is discussed in more detail below.

DNA Binding Agents

The first analysis of kinetic PCR was performed by Higuchi et al. who used ethidium bromide to bind double-stranded DNA products (Higuchi et al., 1992; Higuchi et al., 1993; U.S. Pat. No. 5,994,056; U.S. Published Application No. 2001/6171785). Ethidium bromide, like all other DNA binding agents used in kinetic PCR, is able to increase in fluorescent intensity upon binding. The resulting increase in signal can be recorded over the course of the reaction, and plotted versus the cycle number. Recording the data in this way is more indicative of the initial concentration of the sample of interest compared to end-point analysis.

Binding dyes are relatively inexpensive as compared to other detection chemistries. The advantages of using these binding dyes are their low cost and excellent signal to noise ratios. Disadvantages include their non-specific binding properties to any double-stranded DNA in the PCR reaction, including amplicons created by primer-dimer formations (Wittwer et al., 1997). In order to confirm the production of a specific amplicon, a melting curve analysis should be performed (Ishiguro et al., 1995). Another drawback is that amplification of a longer product will generate more signal than a shorter one. If amplification efficiencies are different, quantification may be even more inaccurate (Bustin and Nolan, 2004).

SYBR® Green I from Invitrogen™ (Carlsbad, Calif.) is a popular intercalating dye (Bengtsson et al., 2003). SYBR® Green I is a cyclically substituted asymmetric cyanine dye (Zipper et al., 2004; U.S. Pat. No. 5,436,134; U.S. Pat. No. 5,658,751). A minor groove binding asymmetric cyanine dye known as BEBO, has been used in real-time PCR. BEBO causes a non-specific increase in fluorescence with time, perhaps due to a slow aggregation process and is less sensitive compared to SYBR® Green I. A similar dye called BOXTO has also been reported for use in qPCR (Bengtsson et al., 2003; U.S. Published Application No. 2006/0211028). Like BEBO, BOXTO is less sensitive than SYBR® Green I (U.S. Published Application No. 2006/0211028).

Other common reporters include YO-PRO-1 and thiazole orange (TO) which are intercalating asymmetric cyanine dyes (Nygren et al., 1998). While these dyes exhibit large increases in fluorescence intensity upon binding, TO and Oxazole Yellow (YO) have been reported to perform poorly in real-time PCR (Bengtsson et al., 2003). Other dyes that may be used include, but are not limited to, pico green, acridinium orange, and chromomycin A3 (U.S. Published Application No. 2003/6569627). Dyes that may be compatible with real-time PCR can be obtained from various vendors such as, Invitrogen, Cambrex Bio Science (Walkersville, Md.), Rockland Inc. (Rockland, Me.), Aldrich Chemical Co. (Milwaukee, Wis.), Biotium (Hayward, Calif.), TATAA Biocenter AB. (Goteborg, Sweden) and Idaho Technology (Salt Lake City, Utah) (U.S. Published Application No. 2007/0020672).

A dye known as EvaGreen™ (Biotium) has shown promise in that it is designed to not inhibit PCR, and is more stable in alkaline conditions as compared to SYBR® Green I (Dorak, 2006; U.S. Published Application No. 2006/0211028). Other newer dyes include the LCGreen® dye family (Idaho Technology). LCGreen® I and LCGreen® Plus are the most commercially competitive of these dyes. LCGreen® Plus is considerably brighter than LCGreen® (U.S. Published Application No. 2007/0020672; Dorak, 2006; U.S. Published Application No. 2005/0233335; U.S. Published Application No. 2066/0019253).

FRET Based Nucleic Acid Detection

Many real-time nucleic acid detection methods utilize labels that interact by Förster Resonance Energy Transfer (FRET). This mechanism involves a donor and acceptor pair wherein the donor molecule is excited at a particular wavelength, and subsequently transfers its energy non-radiatively to the acceptor molecule. This typically results in a signal change that is indicative of the proximity of the donor and acceptor molecules to one another.

Early methods of FRET based nucleic acid detection that lay a foundation for this technology in general, include work by Heller et al. (U.S. Pat. Nos. 4,996,143; 5,532,129; and 5,565,322, which are incorporated by reference). These patents introduce FRET based nucleic acid detection by including two labeled probes that hybridize to the target sequence in close proximity to each other. This hybridization event causes a transfer of energy to produce a measurable change in spectral response, which indirectly signals the presence of the target.

Cardullo et al. (incorporated by reference) established that fluorescence modulation and nonradiative fluorescence resonance energy transfer can detect nucleic acid hybridization in solution (Cardullo et al., 1988). This study used three FRET based nucleic acid detection strategies. The first includes two 5' labeled probes that were complementary to one another, allowing transfer to occur between a donor and acceptor fluorophore over the length of the hybridized complex. In the second method, fluorescent molecules were covalently attached to two nucleic acids, one at the 3' end and the other at the 5' end. The fluorophore-labeled nucleic acids hybridized to distinct but closely spaced sequences of a longer, unlabeled nucleic acid. Finally, an intercalating dye was used as a donor for an acceptor fluorophore that was covalently attached at the 5' end of the probe.

Morrison et al. (1989), incorporated by reference, used complementary labeled probes to detect unlabeled target DNA by competitive hybridization, producing fluorescence signals which increased with increasing target DNA concentration. In this instance, two probes were used that were complementary to one another and labeled at their 5' and 3' ends with fluorescein and fluorescein quencher, respectively. Later work also showed that fluorescence melting curves could be used to monitor hybridization (Morrison and Stols, 1993).

Hybridization Probes

Hybridization probes used in real-time PCR were developed mainly for use with the Roche LightCycler® instruments (U.S. Published Application No. 2001/6174670; U.S. Published Application No. 2000/6140054). These are sometimes referred to as FRET probes, LightCycler® probes, or dual FRET probes (Espy et al., 2006).

Hybridization probes are used in a format in which FRET is measured directly (Wilhelm and Pingoud, 2003). Each of the two probes is labeled with a respective member of a fluorescent energy transfer pair, such that upon hybridization to adjacent regions of the target DNA sequence, the excitation energy is transferred from the donor to the acceptor, and subsequent emission by the acceptor can be recorded as reporter signal (Wittwer et al., 1997). The two probes anneal to the target sequence so that the upstream probe is fluorescently labeled at its 3' end and the downstream probe is labeled at its 5' end. The 3' end of the downstream probe is typically blocked by phosphorylation or some other means to prevent extension of the probe during PCR. The dye coupled to the 3' end of the upstream probe is sufficient to prevent extension of this probe. This reporter system is different from other FRET based detection methods (molecular beacons, TaqMan®, etc.) in that it uses FRET to generate rather than to quench the fluorescent signal (Dorak, 2006).

Typical acceptor fluorophores include the cyanine dyes (Cy3 and Cy5), 6-carboxy-4,7,2',7'-tetrachlorofluorescein (TET), 6-carboxy-N,N,N',N'-tetramethylrhodamine (TAMRA), and 6-carboxyrhodamine X (ROX). Donor fluorophores are usually 6-carboxyfluoroscein (FAM) (Wilhelm and Pingoud, 2003). Hybridization probes are particularly advantageous for genotyping and mismatch detection. Melting curve analysis can be performed in addition to the per-cycle monitoring of fluorescence during the PCR reaction. A slow heating of the sample after probe hybridization can provide additional qualitative information about the sequence of interest (Lay and Wittwer, 1997; Bernard et al., 1998a; Bernard et al., 1998b). Base-pair mismatches will shift the stability of a duplex, in varying amounts, depending on the mismatch type and location in the sequence (Guo et al., 1997).

Molecular Beacons

Molecular beacons, also known as hairpin probes, are stem-loop structures that open and hybridize in the presence of a complementary target sequence, typically causing an increase in fluorescence (U.S. Pat. No. 5,925,517); U.S. Published Application No. 2006/103476). Molecular beacons typically have a nucleic acid target complement sequence flanked by members of an affinity pair that, under assay conditions in the absence of target, interact with one another to form a stem duplex. Hybridization of the probes to their preselected target sequences produces a conformational change in the probes, forcing the "arms" apart and eliminating the stem duplex and thereby separating the fluorophore and quencher.

Hydrolysis Probes

Hydrolysis probes, also known as the TaqMan° assay (U.S. Pat. No. 5,210,015), are popular because they only involve a single probe per target sequence, as opposed to two probes (as in hybridization probes). This results in a cost savings per sample. The design of these probes is also less complicated than that of molecular beacons. These are typically labeled with a reporter on the 5' end and a quencher on the 3' end. When the reporter and quencher are fixed onto the same probe, they are forced to remain in close proximity. This proximity effectively quenches the reporter signal, even when the probe is hybridized to the target sequence. During the extension or elongation phase of the PCR reaction, a polymerase known as Taq polymerase is used because of its 5' exonuclease activity. The polymerase uses the upstream primer as a binding site and then extends. Hydrolysis probes are cleaved during polymerase extension at their 5' end by the 5'-exonuclease activity of Taq. When this occurs, the reporter fluorophore is released from the probe, and subsequently, is no longer in close proximity to the quencher. This produces a perpetual increase in reporter signal with each extension phase as the PCR reaction continues cycling. In order to ensure maximal signal with each cycle, hydrolysis probes are designed with a Tm that is roughly 10° C. higher than the primers in the reaction.

However, the process of cleaving the 5' end of the probe need not require amplification or extension of the target sequence (U.S. Pat. No. 5,487,972). This is accomplished by placing the probe adjacent to the upstream primer, on the target sequence. In this manner, sequential rounds of annealing and subsequent probe hydrolysis can occur, resulting in a significant amount of signal generation in the absence of polymerization. Uses of the real-time hydrolysis probe reaction are also described in U.S. Pat. Nos. 5,538,848 and 7,205,105, both of which are incorporated by references.

Dye-Primer Based Systems

There are numerous dye-labeled primer based systems available for real-time PCR. These range in complexity from simple hairpin primer systems to more complex primer structures where the stem-loop portion of the hairpin probe is attached via a non-amplifiable linker to the specific PCR primer. These methods have the advantage that they do not require an additional intervening labeled probe that is essential for probe-based assay systems and they also allow for multiplexing that is not possible with DNA binding dyes. However, the success of each of these methods is dependent upon careful design of the primer sequences.

Hairpin primers contain inverted repeat sequences that are separated by a sequence that is complementary to the target DNA (Nazarenko et al., 1997; Nazarenko et al., 2002; U.S. Pat. No. 5,866,336). The repeats anneal to form a hairpin structure, such that a fluorophore at the 5'-end is in close proximity to a quencher at the 3'-end, quenching the fluorescent signal. The hairpin primer is designed so that it will preferentially bind to the target DNA, rather than retain its hairpin structure. As the PCR reaction progresses, the primer anneals to the accumulating PCR product, the fluorophore and quencher become physically separated, and the level of fluorescence increases.

Invitrogen's LUX™ (Light Upon eXtension) primers are fluorogenic hairpin primers which contain a short 4-6 nucleotide extension at the 5' end of the primer that is complementary to an internal sequence near the 3' end and overlaps the position of a fluorophore attached near the 3' end (Chen et al., 2004; Bustin, 2002). Basepairing between the complementary sequences forms a double-stranded stem which quenches the reporter dye that is in close proximity at the 3' end of the primer. During PCR, the LUX™ primer is incorporated into the new DNA strand and then becomes linearized when a new complementary second strand is generated. This structural change results in an up to 10-fold increase in the fluorescent signal. These primers can be difficult to design and secondary structure must be carefully analyzed to ensure that the probe anneals preferentially to the PCR product. Design and validation services for custom LUX™ primers are available from Invitrogen.

More recently, hairpin probes have become part of the PCR primer (Bustin, 2002). In this approach, once the primer is extended, the sequence within the hairpin anneals to the newly synthesized PCR product, disrupting the hairpin and separating the fluorophore and quencher.

Scorpion® primers are bifunctional molecules in which an upstream hairpin probe sequence is covalently linked to a downstream primer sequence (U.S. Published Application No. 2001/6270967; U.S. Published Application No. 2005/0164219; Whitcombe et al., 1999). The probe contains a fluorophore at the 5' end and a quencher at the 3' end. In the absence of the target, the probe forms a 6-7 base stem, bringing the fluorophore and quencher in close proximity and allowing the quencher to absorb the fluorescence emitted by the fluorophore. The loop portion of the scorpion probe section consists of sequence complementary to a portion of the target sequence within 11 bases downstream from the 3' end of the primer sequence. In the presence of the target, the probe becomes attached to the target region synthesized in the first PCR cycle. Following the second cycle of denaturation and annealing, the probe and the target hybridize. Denaturation of the hairpin loop requires less energy than the new DNA duplex produced. Thus, the scorpion probe loop sequence hybridizes to a portion of the newly produced PCR product, resulting in separation of the fluorophore from the quencher and an increase in the fluorescence emitted.

As with all dye-primer based methods, the design of Scorpion primers follows strict design considerations for secondary structure and primer sequence to ensure that a secondary reaction will not compete with the correct probing event. The primer pair should be designed to give an amplicon of approximately 100-200 bp. Ideally, the primers should have as little secondary structure as possible and should be tested for hairpin formation and secondary structures. The primer should be designed such that it will not hybridize to the probe element as this would lead to linearization and an increase in non-specific fluorescence emission. The Tm's of the two primers should be similar and the stem Tm should be 5-10° C. higher than the probe Tm. The probe sequence should be 17-27 bases in length and the probe target should be 11 bases or less from the 3' end of the scorpion. The stem sequence should be 6 to 7 bases in length and should contain primarily cytosine and guanine. The 5' stem sequence should begin with a cytosine as guanine may quench the fluorophore. Several oligonucleotide design software packages contain algorithms for Scorpion primer design and custom design services are available from some oligonucleotide vendors as well.

The Plexor™ system from Promega is a real-time PCR technology that has the advantage that there are no probes to design and only one PCR primer is labeled (U.S. Pat. No. 5,432,272; U.S. Published Application No. 2000/6140496; U.S. Published Application No. 2003/6617106). This technology takes advantage of the specific interaction between two modified nucleotides, isoguanine (iso-dG) and 5'-methylisocytosine (iso-dC) (Sherrill et al., 2004; Johnson et al., 2004; Moser and Prudent, 2003). Main features of this technology are that the iso-bases will only base pair with the complementary iso-base and DNA polymerase will only incorporate an iso-base when the corresponding complementary iso-base is present in the existing sequence. One PCR primer is synthesized with a fluorescently-labeled iso-dC residue as the 5'-terminal nucleotide. As amplification progresses, the labeled primer is annealed and extended, becoming incorporated in the PCR product. A quencher-labeled iso-dGTP (dabsyl-iso-dGTP), available as the free nucleotide in the PCR master mix, specifically base pairs with the iso-dC and becomes incorporated in the complementary PCR strand, quenching the fluorescent signal. Primer design for the Plexor system is relatively simple as compared to some of the other dye-primer systems and usually follows typical target-specific primer design considerations. A web-based Plexor Primer Design Software, available from Promega, assists in selecting the appropriate dye and quencher combinations, and provides links to oligonucleotide suppliers licensed to provide iso-base containing primers.

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

The following references, to the extent that they provide exemplary procedural or other details supplementary to those set forth herein, are specifically incorporated herein by reference.

Bengtsson et al., Nucleic Acids Res., 31:e45, 2003.
Bernard et al., Am. J. Pathol., 153:1055-1061, 1998.
Bernard et al., Anal. Biochem., 255:101-107, 1998.
Bustin et al., J. Biomol. Tech., 15:155-166, 2004.
Bustin, J. Mol. Endocrinol., 29(1):23-39, 2002.
Cardullo et al., Proc. Natl. Acad. Sci. USA, 85:8790-8804, 1988.
Chen et al., J. Virol. Methods, 122(1):57-61, 2004.
Dorak, In: Real-time PCR, Bios Advanced Methods, 1st Ed., Taylor & Francis, 2006.
Egholm et al., Nature, 365(6446):566-568, 1993.
Espy et al., Clin. Microbiol. Rev., 19(1):165-256, 2006.
Guo et al., Nat. Biotechnol., 4:331-335, 1997.
Higuchi et al., Biotechnol., 10: 412-417, 1992.
Higuchi et al., Biotechnol., 11:1026-1030, 1993.
Ishiguro et al., Anal. Biochemistry, 229(2): 207-213, 1995.
Johnson et al., Nucl. Acids Res., 32:1937-1941, 2004.
Koshkin and Dunford, J. Biol. Chem., 273(11):6046-6049, 1998a.
Koshkin and Wengel, J. Org. Chem., 63(8):2778-2781, 1998b.
Lay and Wittwer, Clin. Chem., 1997; 43: 2262-2267, 1997.
Morrison et al., Anal. Biochem., 183:231-244, 1989.
Morrison et al., Biochemistry, 32:3095-3104, 1993.
Moser et al., Nucl. Acids Res., 31:5048-5053, 2003.
Mueller et al., Current Protocols in Mol. Biol.; 15:5, 1993.
Nazarenko et al., Nucleic Acids Res., 25(12):2516-2521, 1997.
Nazarenko et al., Nucleic Acids Res., 30(9):37, 2002.
Nygren et al., Biopolymers, 46:39-51, 1998.
Sano, T. et al., Science, 258:120-122, 1992.
Santalucia et al., Biochemistry; 38:3468-3477, 1999.
Sherrill et al., J. Am. Chem. Soc., 126:4550-4556, 2004.
Sims, P W et al., Anal Biochem. 281:230-232, 2000.
Wahlestedt et al., Proc. Natl. Acad. Sci. USA, 97(10):5633-5638, 2000.
Whitcombe et al., Nat. Biotechnol., 17:804-807, 1999.
Wilhelm and Pingoud, Chem. BioChem., 4:1120-1128, 2003.
Wittwer et al., Biotechniques, 22:130-138, 1997.
Zipper et al., Nucleic Acids Res., 32(12):103, 2004.

EXAMPLES

Example 1

Case Study—In Situ Hematologic Biofilm Communities in 3 patients with ALS

Spontaneous Amyotrophic Lateral Sclerosis, Lou Gehrig's disease (ALS) is a debilitating neurologic disease with an unknown cause and poor prognosis. Efforts to determine the etiology have not been conclusive. It is believed that ALS has an infectious trigger and the causative pathogen could be found in the peripheral circulation, and that the utilization of careful microscopic, histological, and molecular techniques could provide insight into the mechanism of disease. Suspecting that ALS is an infectious disease with great antibiotic resistance, the existence of a biofilm-based pathogen was postulated. Peripheral smears from three ALS patients were examined with a variety of stains and techniques. Molecular analysis of peripheral blood samples using broad fungal, prokaryotic and protozoan probes was done. Results indicated the presence of biofilm communities. Molecular analysis suggested the presence of protozoan, bacterial, and fungal organisms.

Case Report: Spontaneous Amyotrophic Lateral Sclerosis, Lou Gehrig's disease (ALS) is a debilitating neurologic disease with an unknown cause and poor prognosis. Recent work has demonstrated chronic cerebral venous insufficiency (CCVI) in Multiple Sclerosis (MS) patients (1). Clearance of CCVI membranous obstruction by percutaneous transluminal angioplasty results in clinical improvement in MS. It has been suggested that the same mechanism may be present in ALS (2). It is believed that ALS is an infectious disease with great antibiotic resistance, and the existence of a biofilm based pathogen was postulated. This biofilm could manifest as the macroscopic membranes visualized in the work by Zamboni.

Peripheral blood samples from three ALS patients were collected after obtaining informed consent. This study was approved by the Fry Laboratories institutional review committee. All three patients were diagnosed by a board certified neurologist. A number of techniques were utilized including Höechst staining, modified May-Grünewald, Periodic Acid-Schiff Reagent, Giemsa and light microscopy techniques (3). Molecular analysis by PCR was done by using bacterial, fungal, and protozoan primers. Microscopic examination of stained smears revealed an abundance of epierythrocytic bacteria attached to peripheral red blood cells. These were 1-2 micrometers in diameter, coccoid and coccobacillary, and consistent with the description of Hemobartonella published in the human and veterinary literature (4).

Examination of histological preparations revealed amorphous clusters of material that on first impression appear to be artifact or 'dirt'. Further examination with high power microscopy, Höechst stain, Ethidium Bromide, or Giemsa staining revealed a mixed population of eukaryotic appearing organisms, adherent lymphocytes, and smaller bacterial shapes consistent with the organisms previously observed and described as Hemobartonella. The sizes of these clusters were 20-100 micrometers. PAS stain revealed a polysaccharide matrix found throughout contributing to cluster morphology. The composition and appearance of these clusters were consistent with previous published and observed biofilm communities (5).

DNA was extracted from peripheral blood and assessed by PCR using general and specific bacterial, fungal and protozoan primers. Analysis of PCR products by sequencing and BLAST confirmed mixed populations of organisms. These consisted of Proteobacteria (primarily *Ralstonia* spp.), fungi, human DNA, and evidence suggestive of protozoans. All three patients with ALS displayed similar findings.

Figure 2:
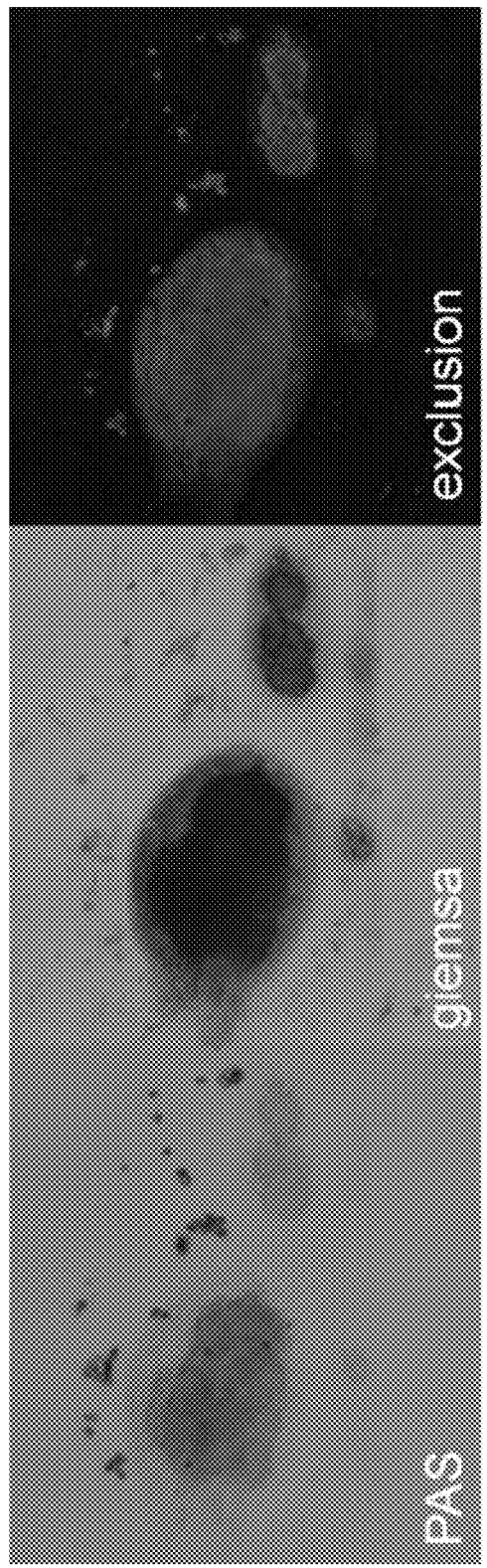
FIGS. 2 and 3 are PAS and Höechst stains respectively revealing that the extracellular matrix material associated with the clusters of FIG. 1 contain both DNA and polysaccharides.
Figure 3:
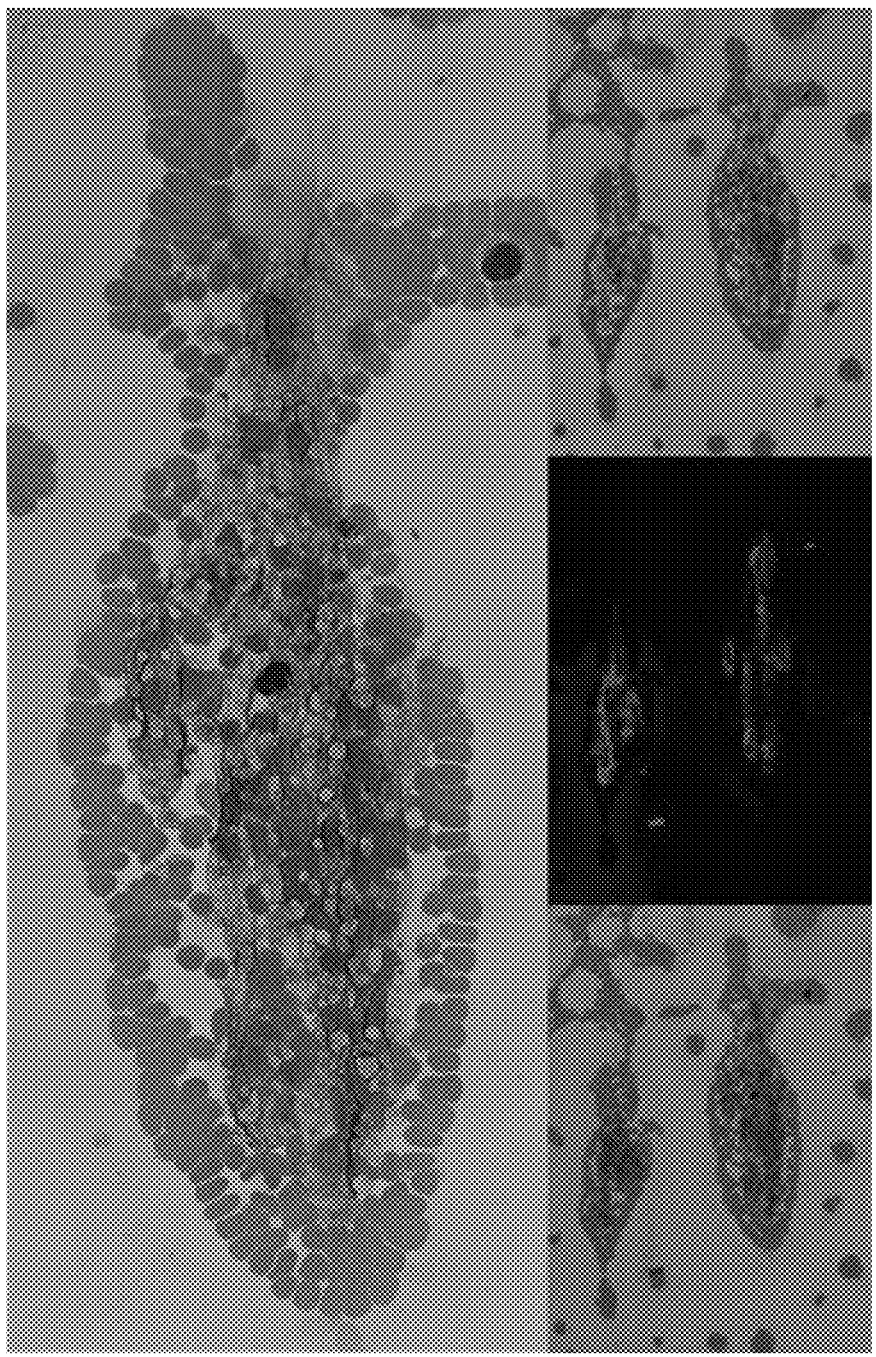
Figure 5:
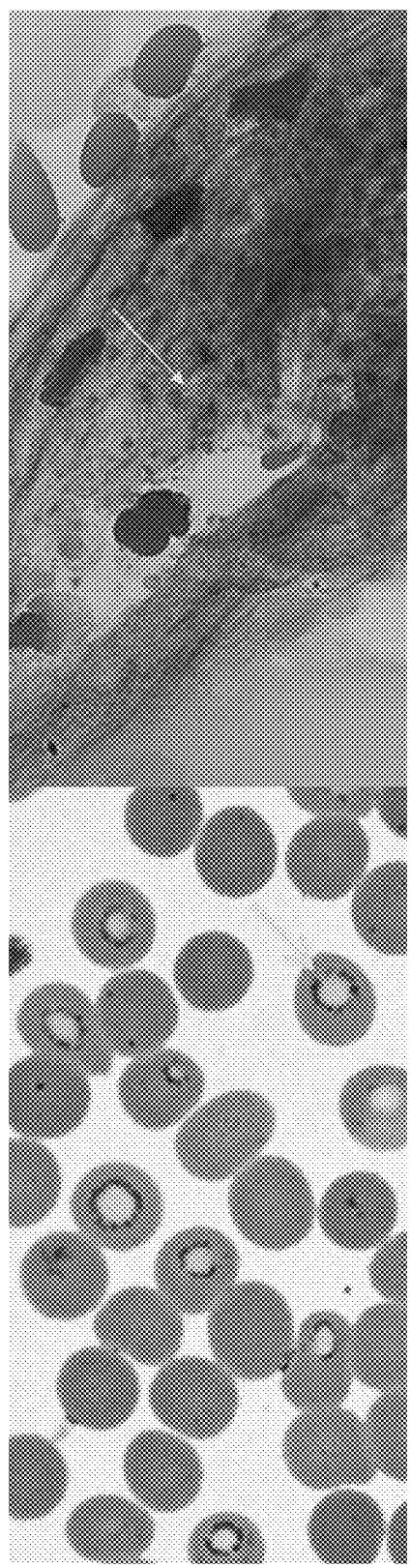
FIG. 5 depicts two panels that are modified May-Grünwald stains (1000×), the Left Panel showing ring forms within red blood cells (yellow arrow) found in association with biofilms and may represent part of the organisms life cycle, and the Right Panel showing biofilm detection with embedded organisms (yellow arrow) which are rarely detected by traditional means.
Figure 6:
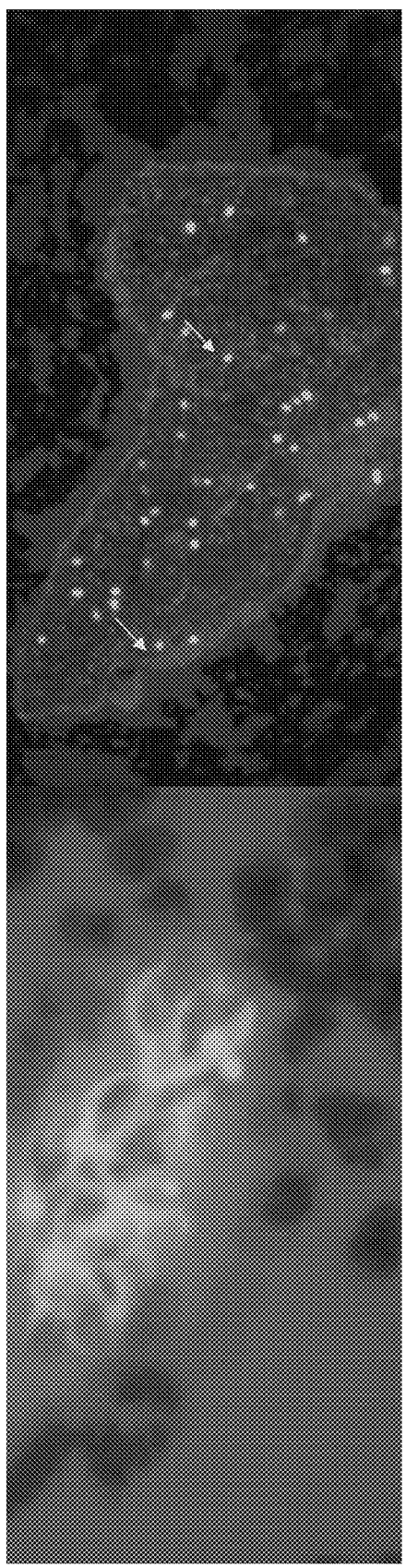
FIG. 6 depicts two panels that are fluorescent DNA stains revealing the presence of biofilms in patients with chronic inflammatory and neurologic disease, the Left Panel showing a high magnification (400×) image revealing irregular size organisms bound by a DNA rich biofilm matrix, and the Right Panel showing a low magnification (100×) image demonstrating the lymphocytic response with adherent white blood cells (yellow arrows) to a large biofilm cluster.
Figure 9:
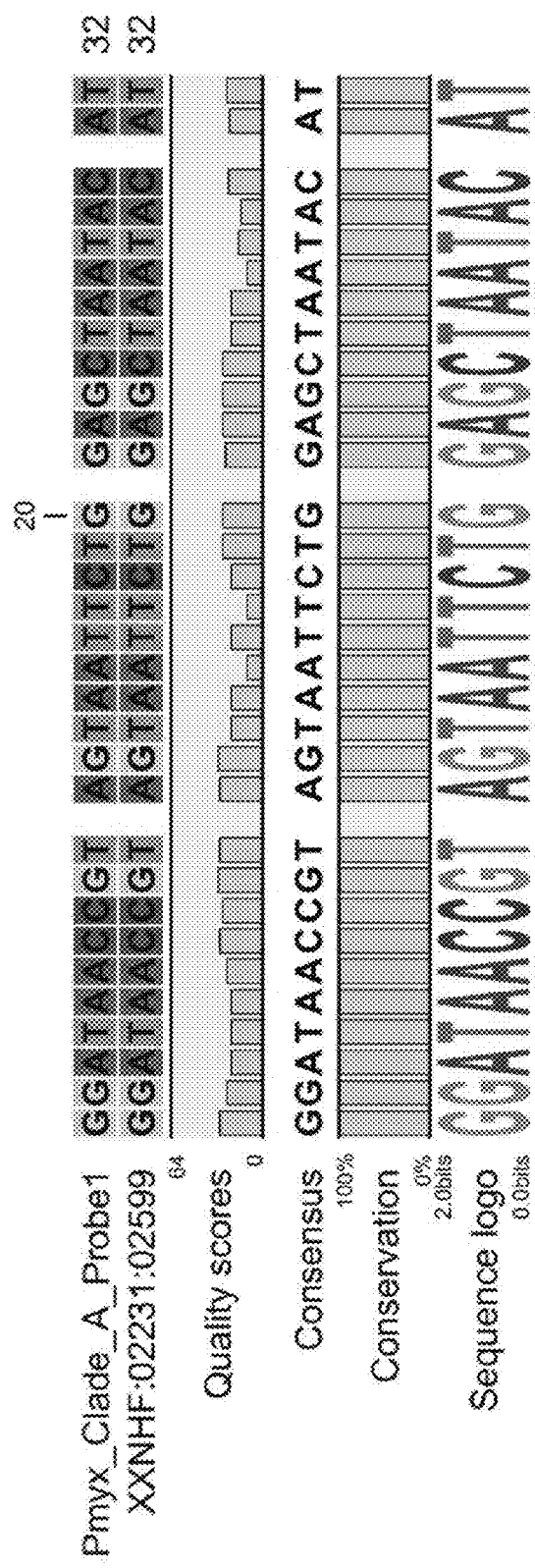
FIG. 9 depicts protozoal species detected with oligonucleotide probe Pmyx_Clade_A_Probe1 (aka Pmyx_Clade_A1 and A1).
Figure 10A:
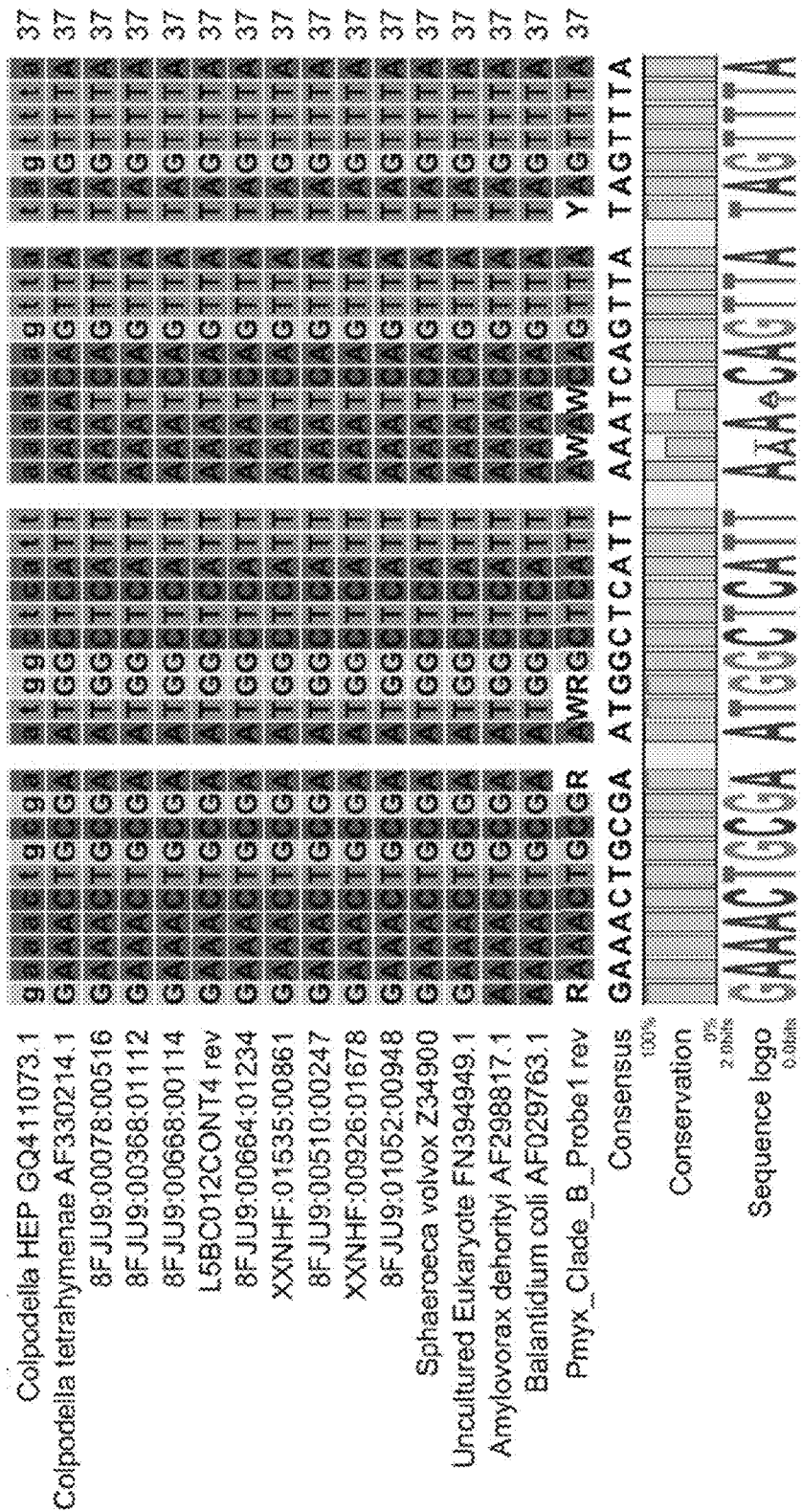
FIG. 10A-10F depict protozoal species detected with oligonucleotide probe Pmyx_Clade_B_Probe1 (aka Pmyx_Clade_B1 and B1).
Figure 10B:
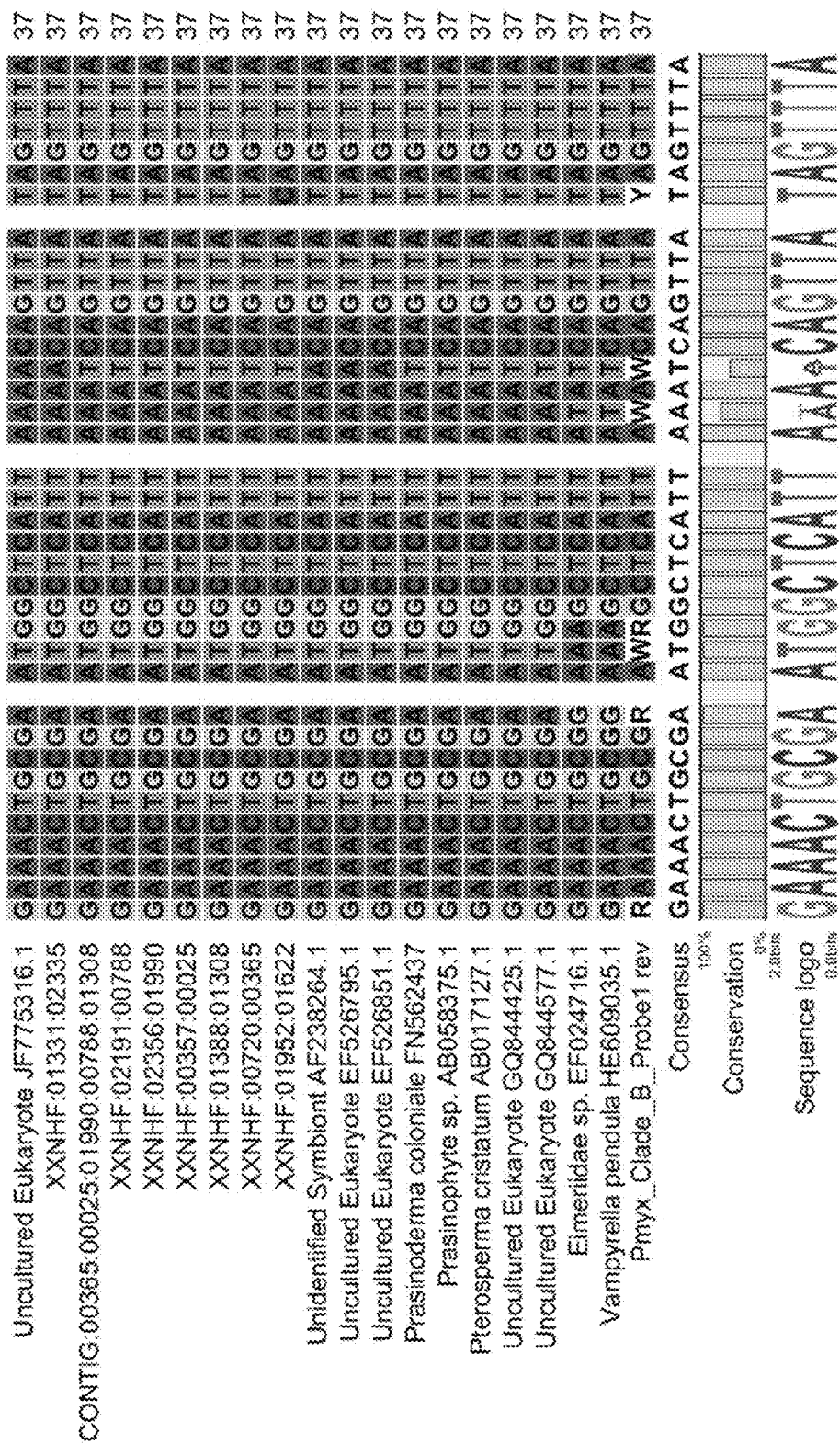
Figure 10C:
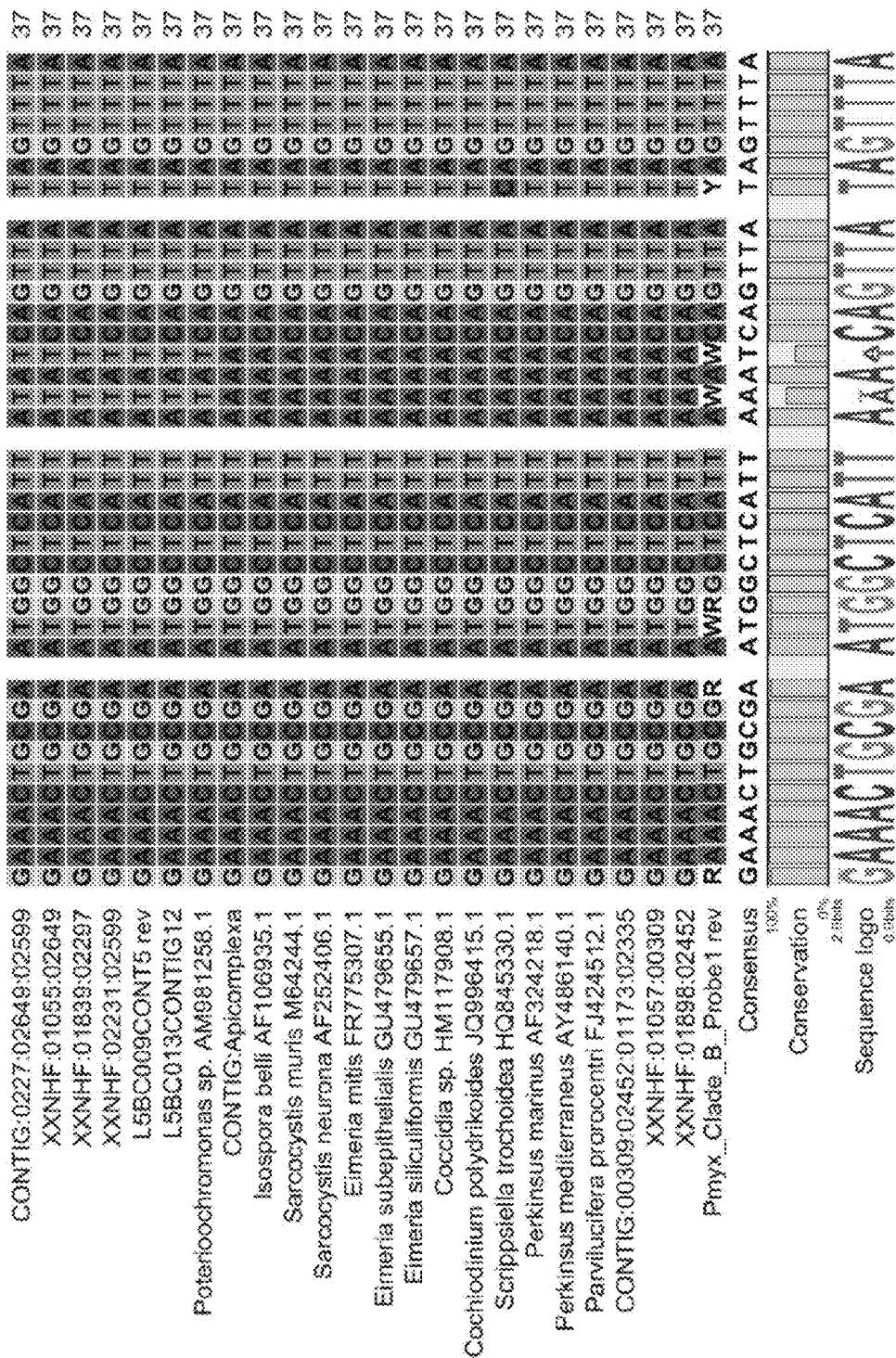
Figure 10D:
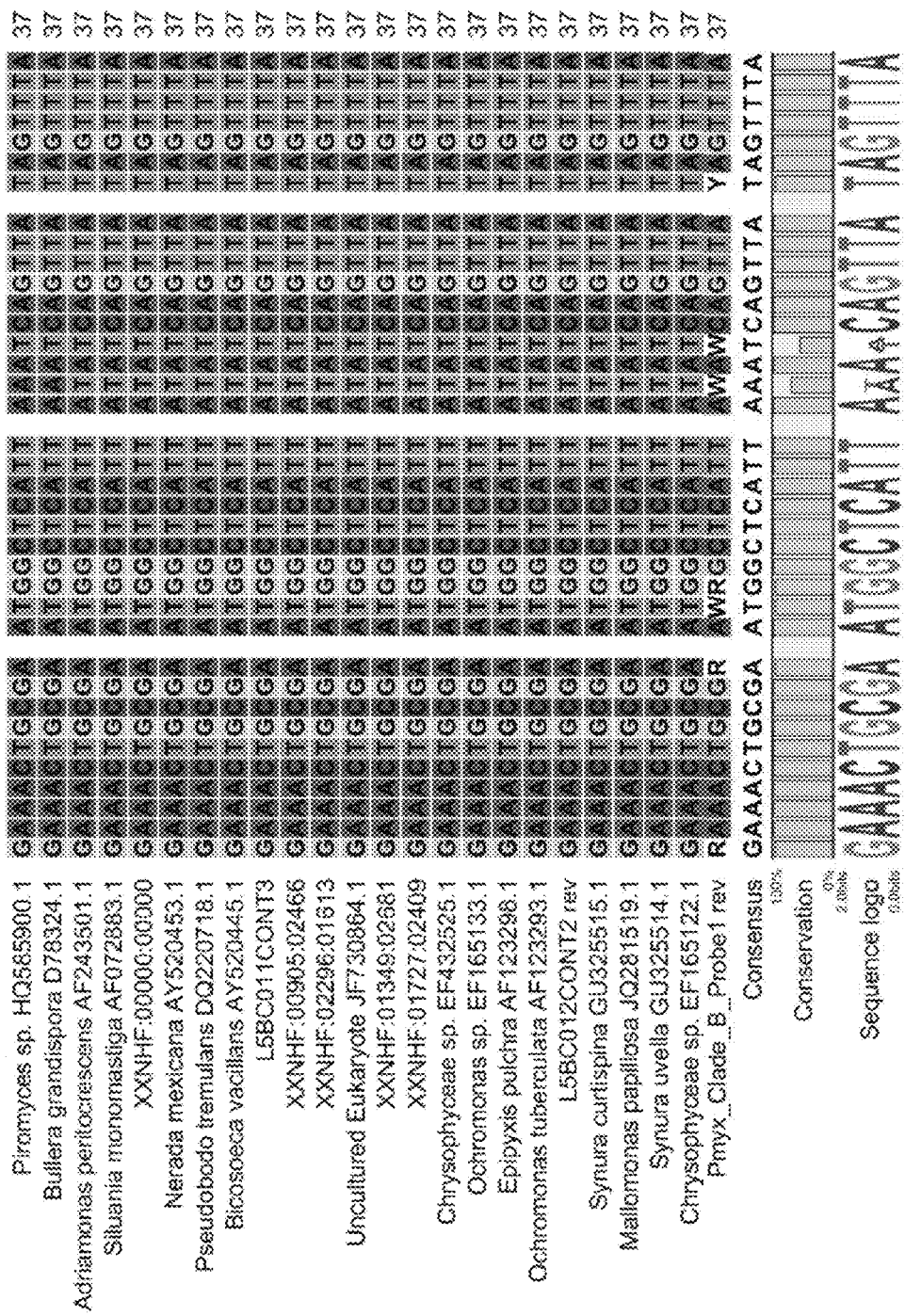
Figure 10E:
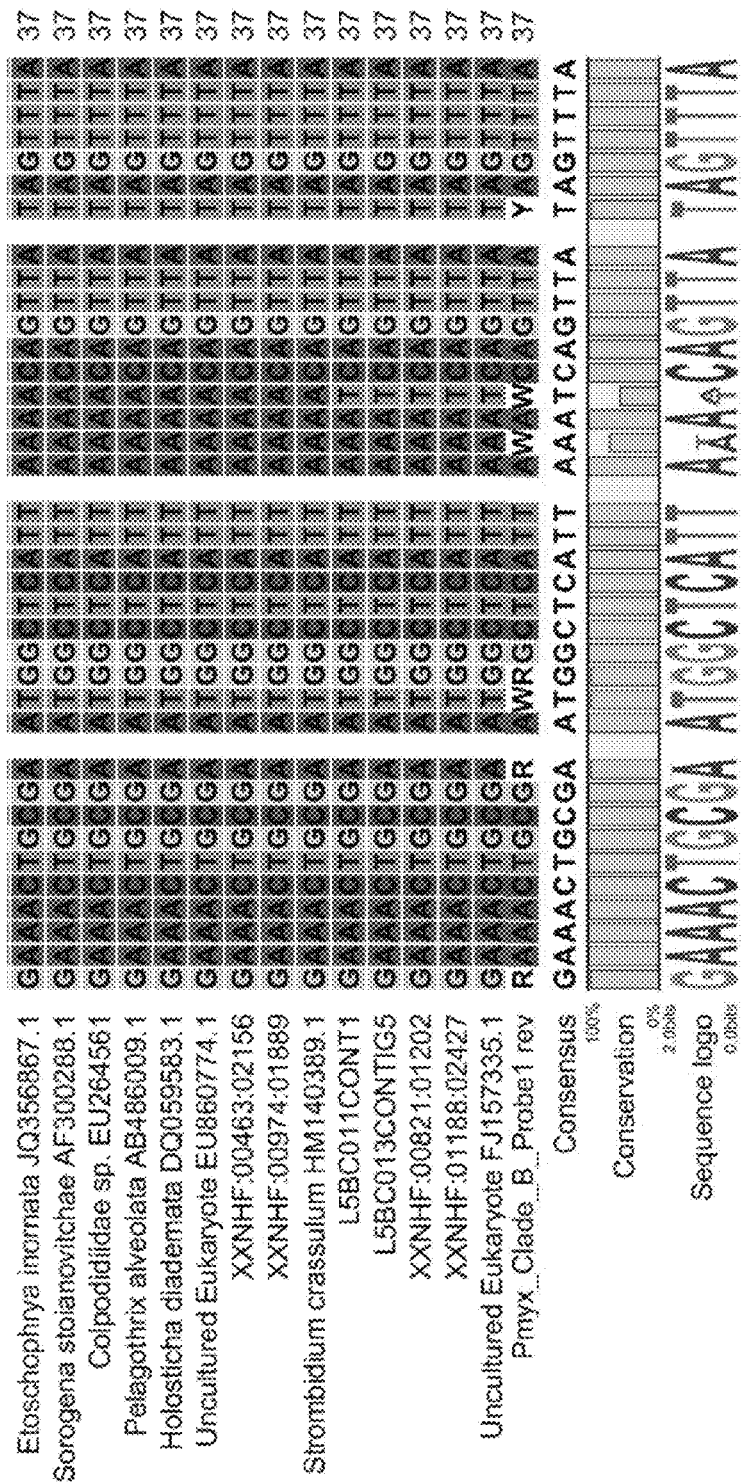
Figure 10F:
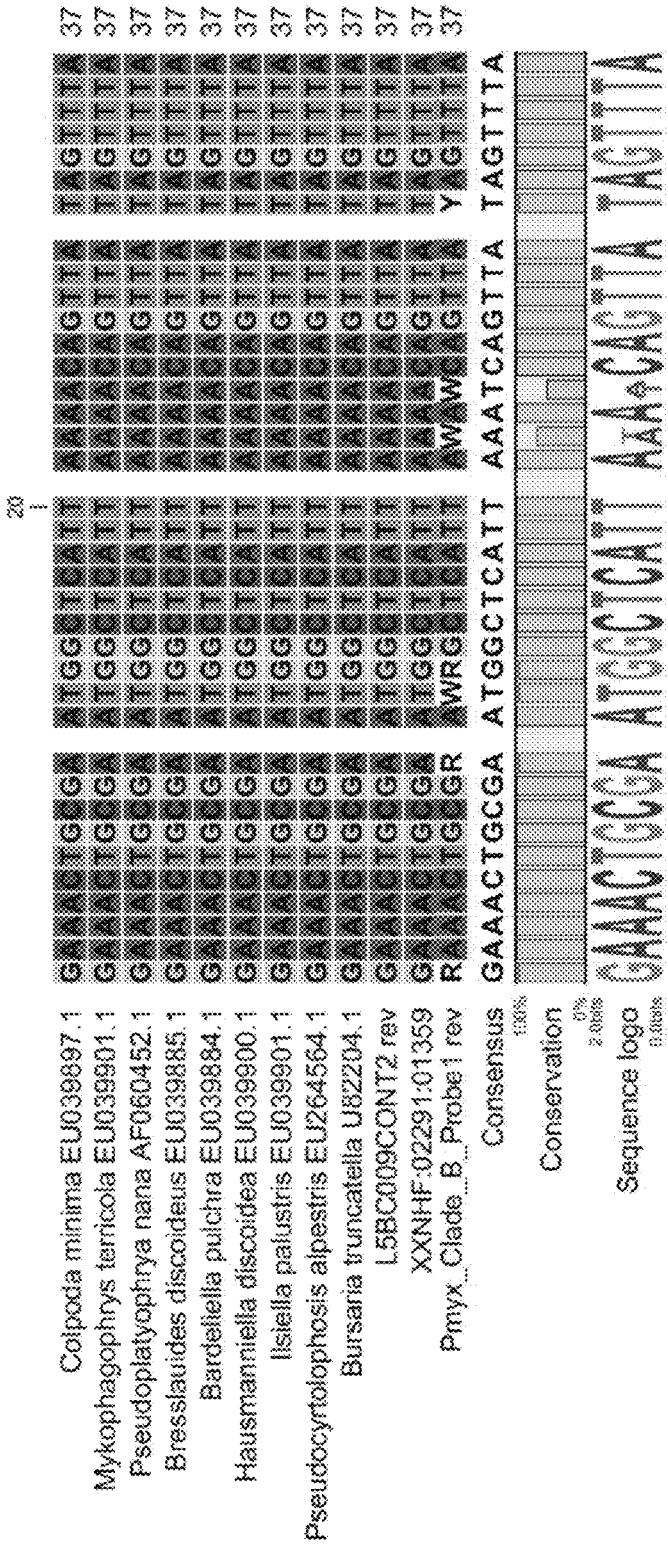
Figure 11:
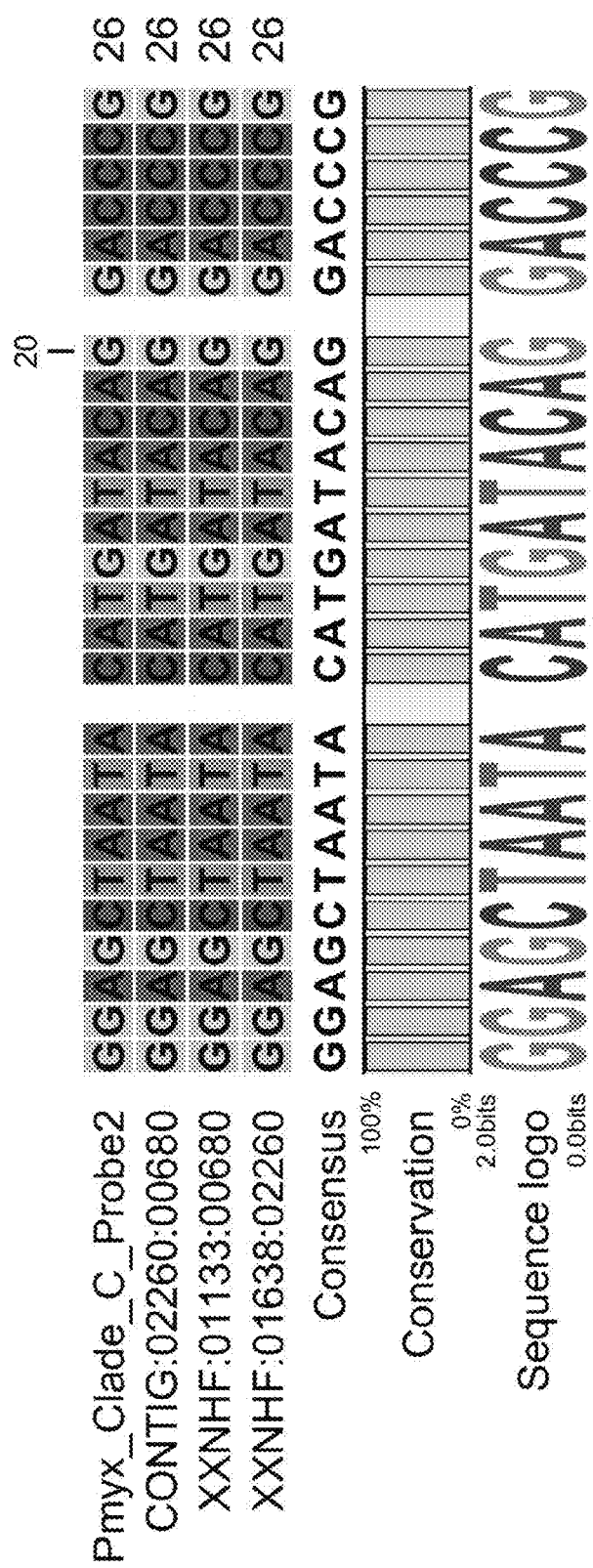
FIG. 11 depicts protozoal species detected with oligonucleotide probe Pmyx_Clade_C_Probe2 (aka Pmyx_Clade_C2 and C2).
Figure 12:
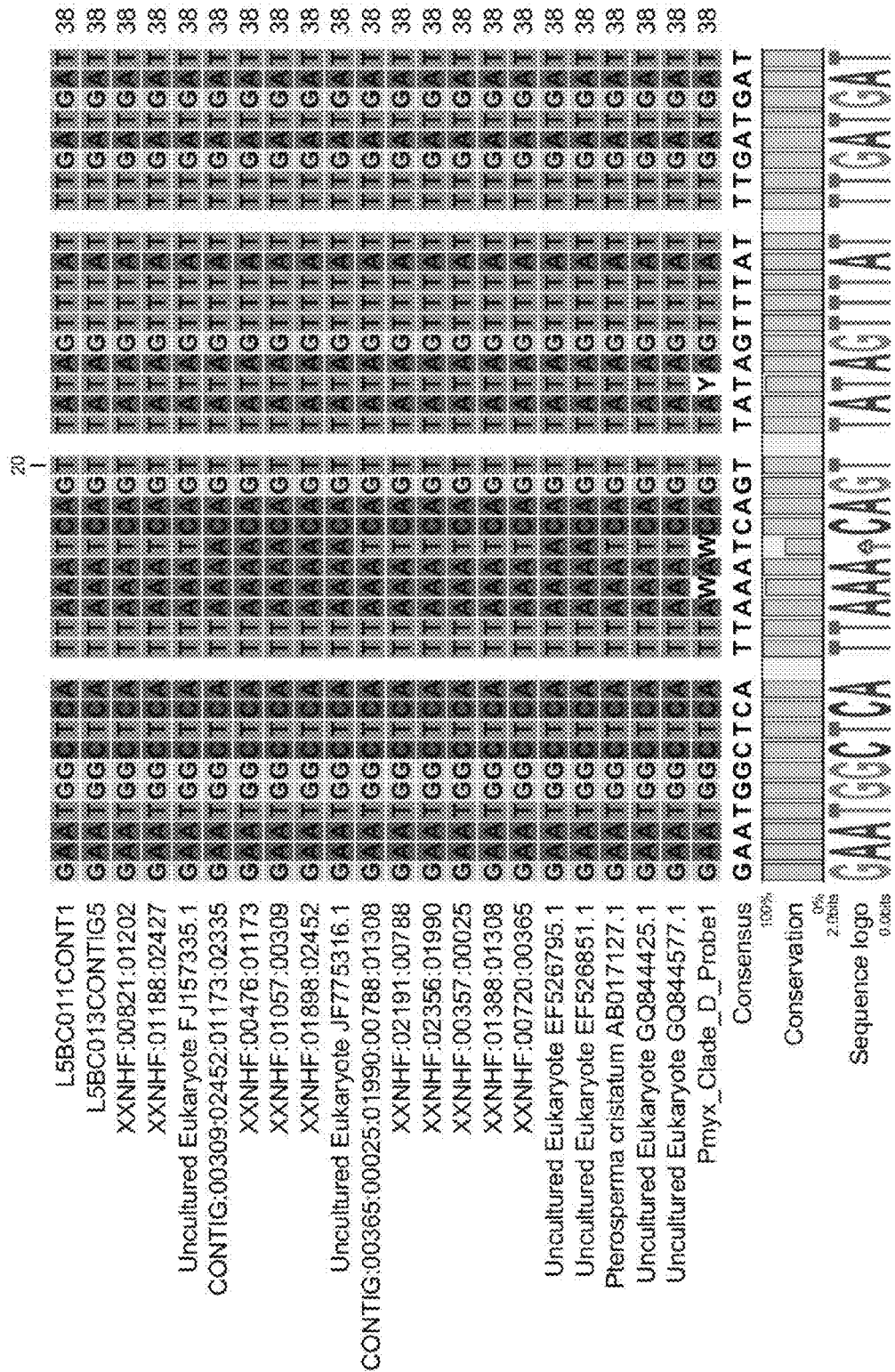
FIG. 12 depicts protozoal species detected with oligonucleotide probe Pmyx_Clade_D_Probe1 (aka Pmyx_Clade_D1 and D1).
Figure 13:
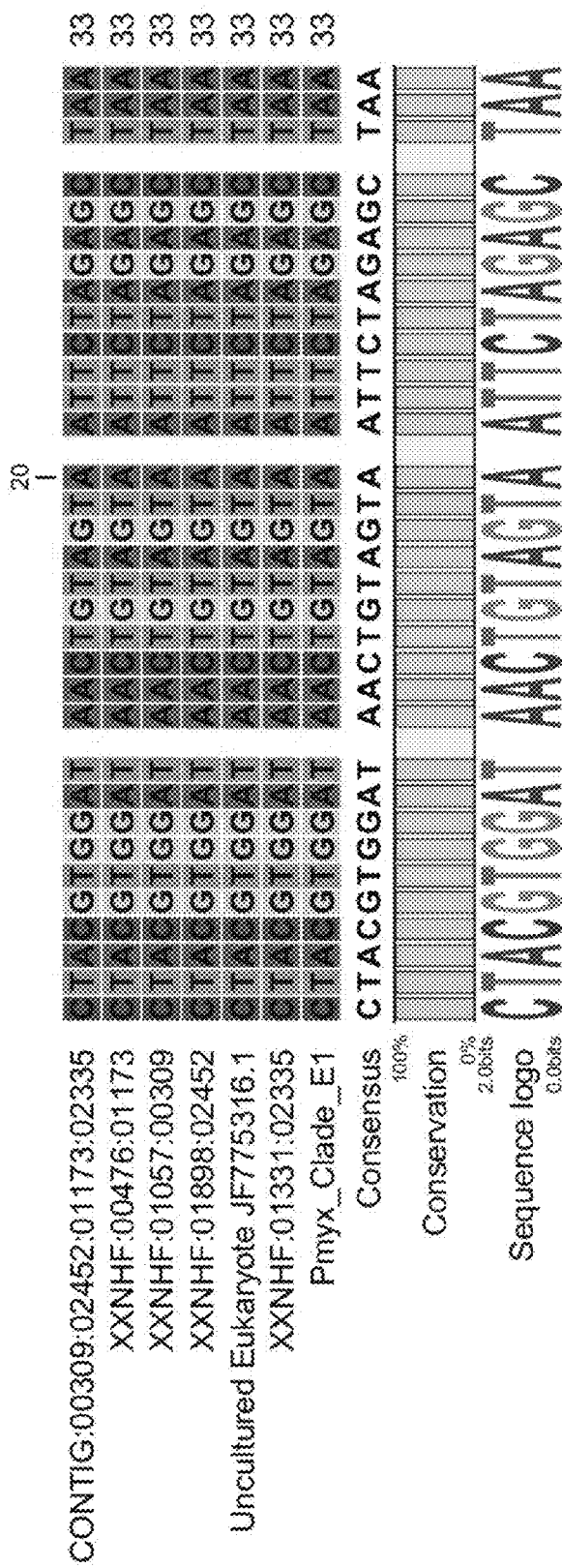
FIG. 13 depicts protozoal species detected with oligonucleotide probe Pmyx_Clade_E_Probe1 (aka Pmyx_Clade_E1 and E1).
Figure 14:
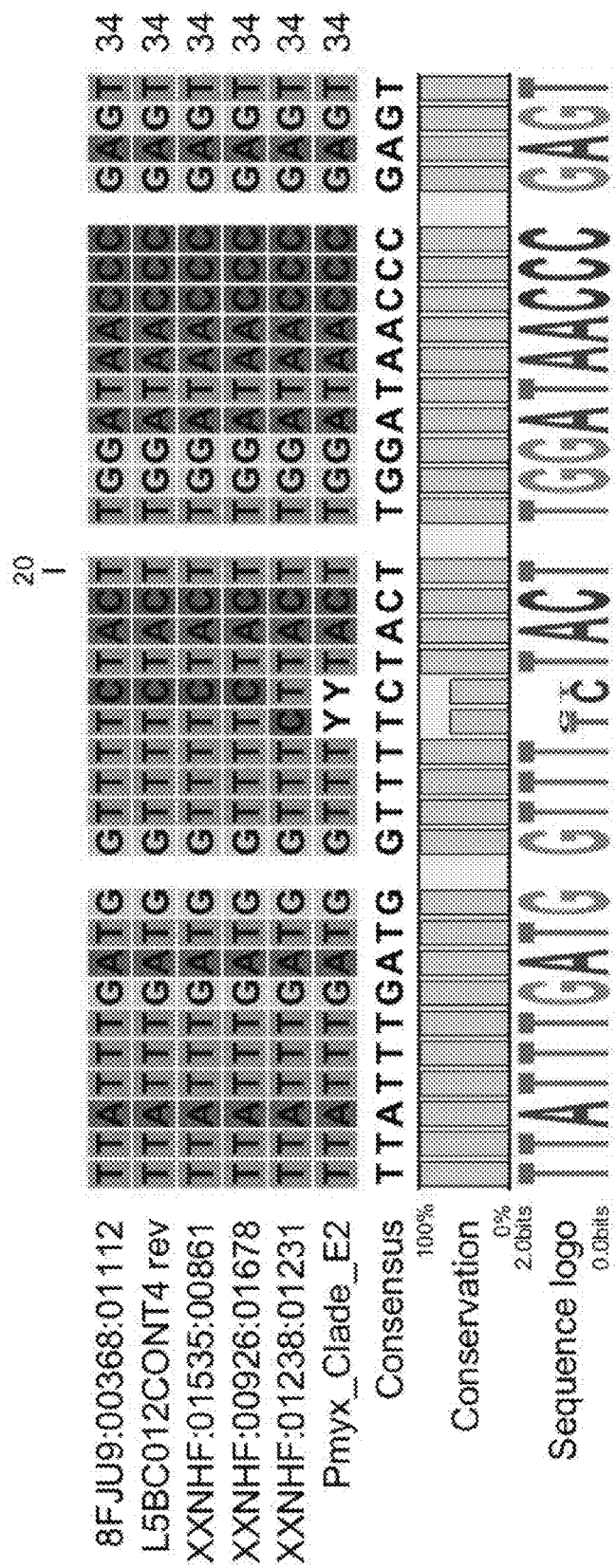
FIG. 14 depicts protozoal species detected with oligonucleotide probe Pmyx_Clade_E_Probe2 (aka Pmyx_Clade_E2 and E2).
Figure 15:
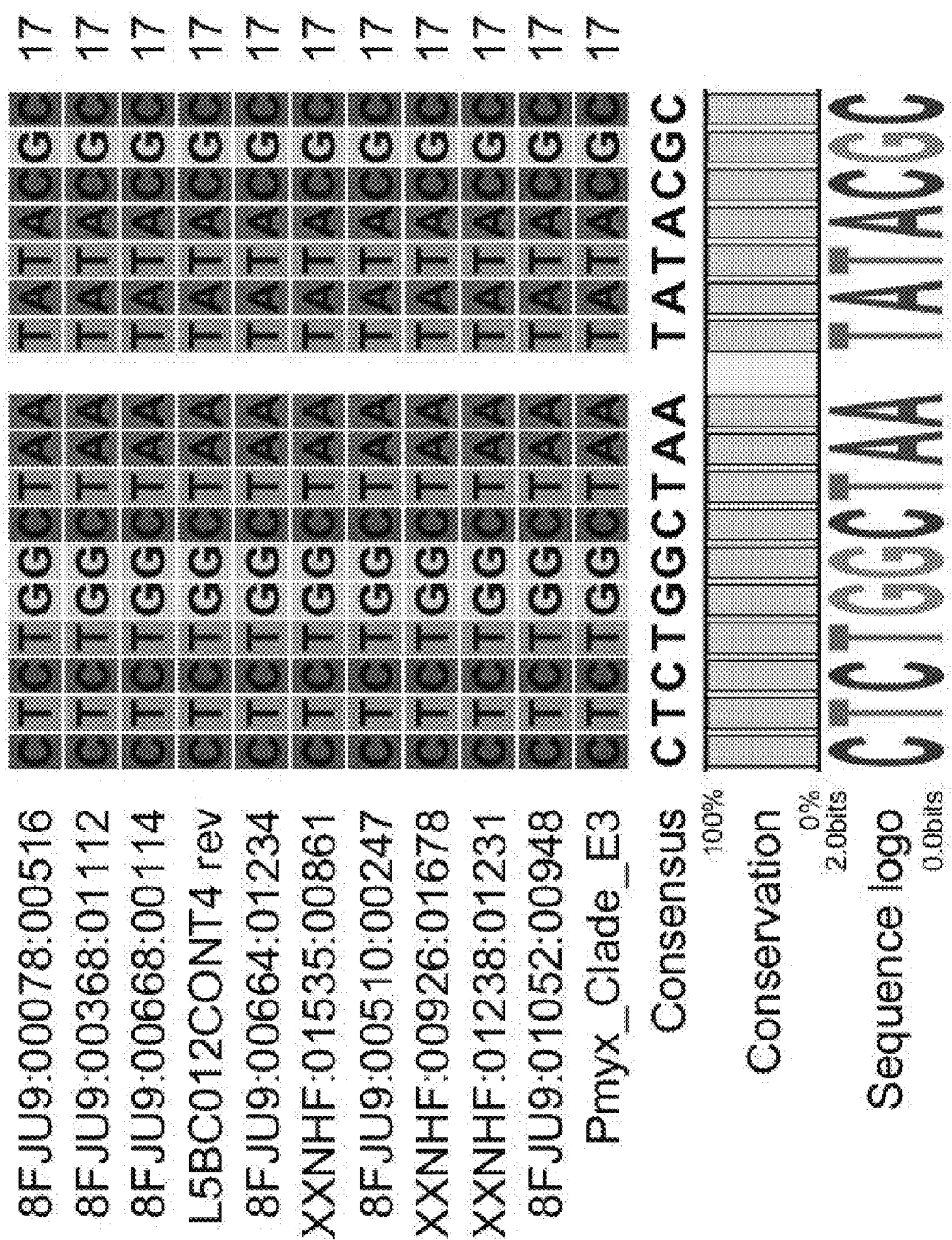
FIG. 15 depicts protozoal species detected with oligonucleotide probe Pmyx_Clade_E_Probe3 (aka Pmyx_Clade_E3 and E3).
Figure 16A:
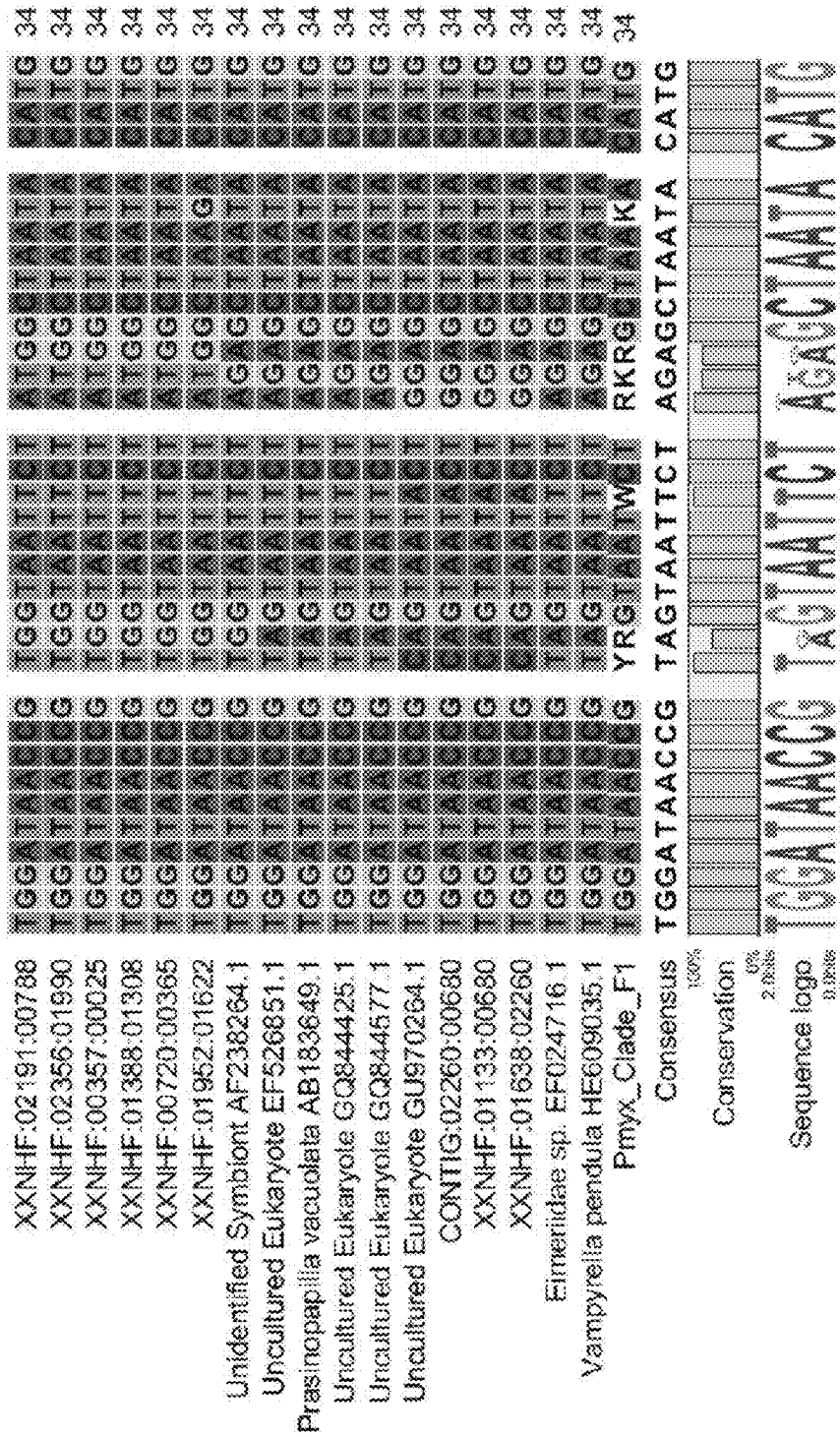
FIG. 16A-16E depict protozoal species detected with oligonucleotide probe Pmyx_Clade_F_Probe1 (aka Pmyx_Clade_F1 and F1).
Figure 16B:
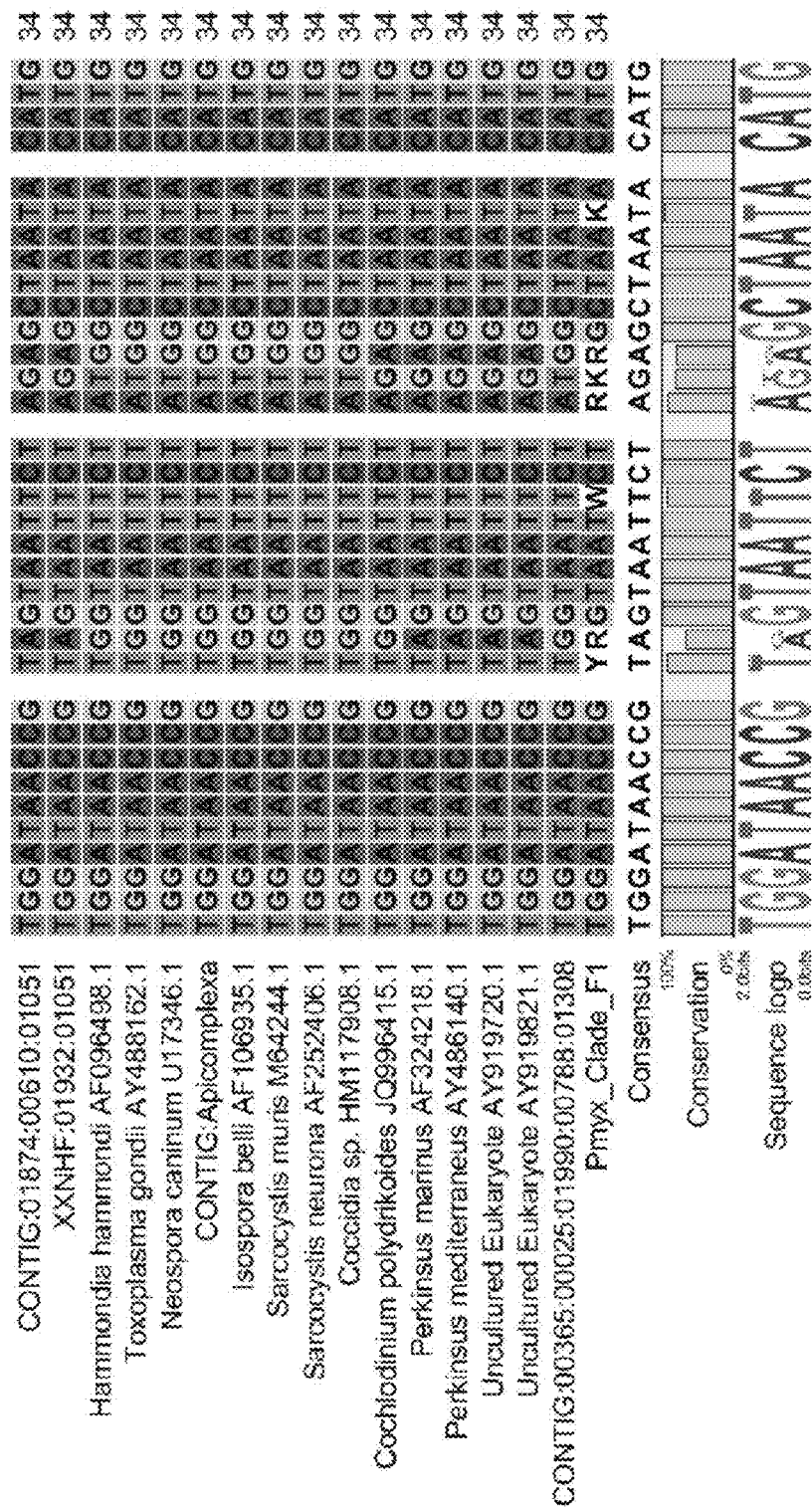
Figure 16C:
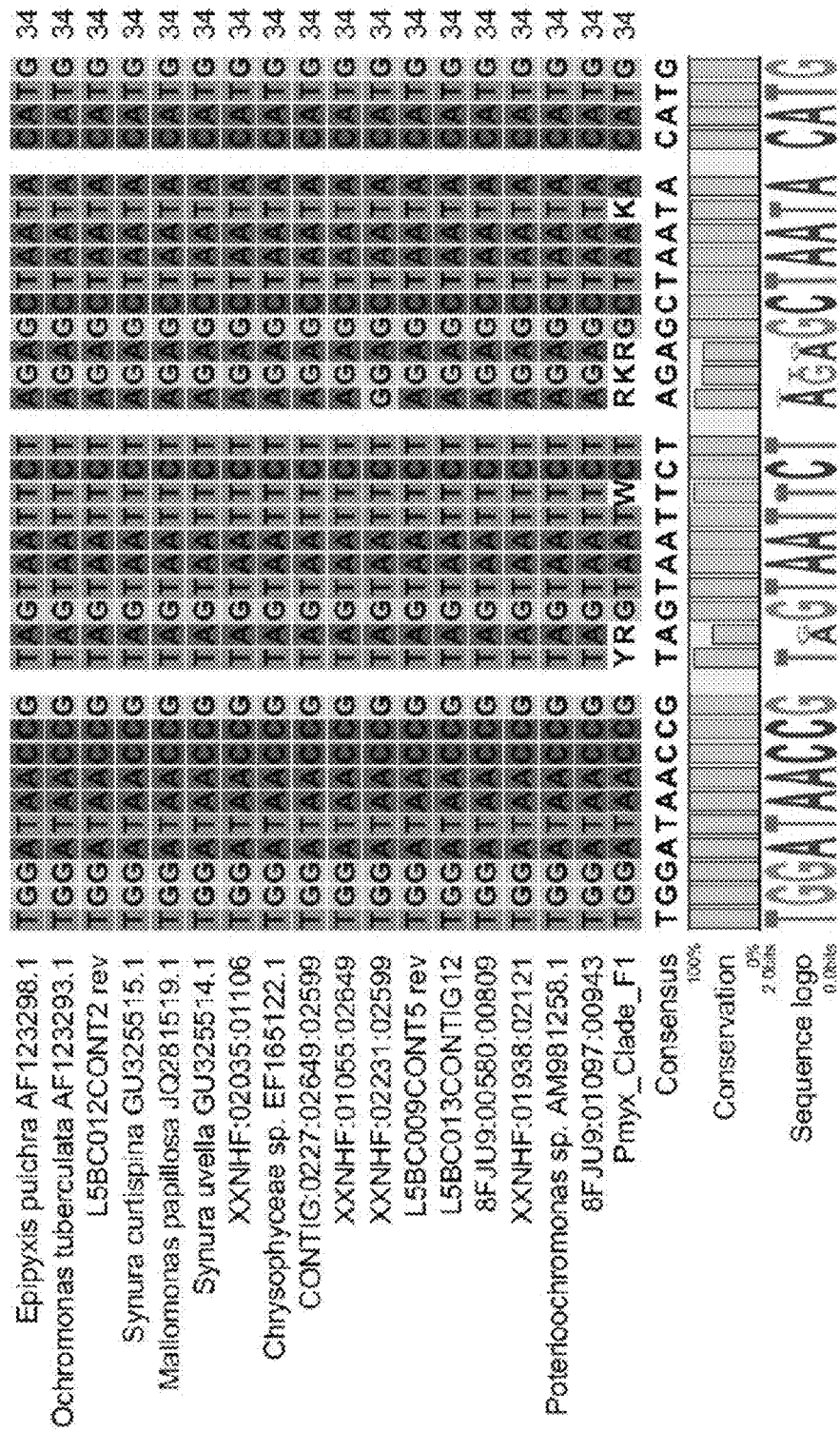
Figure 16D:
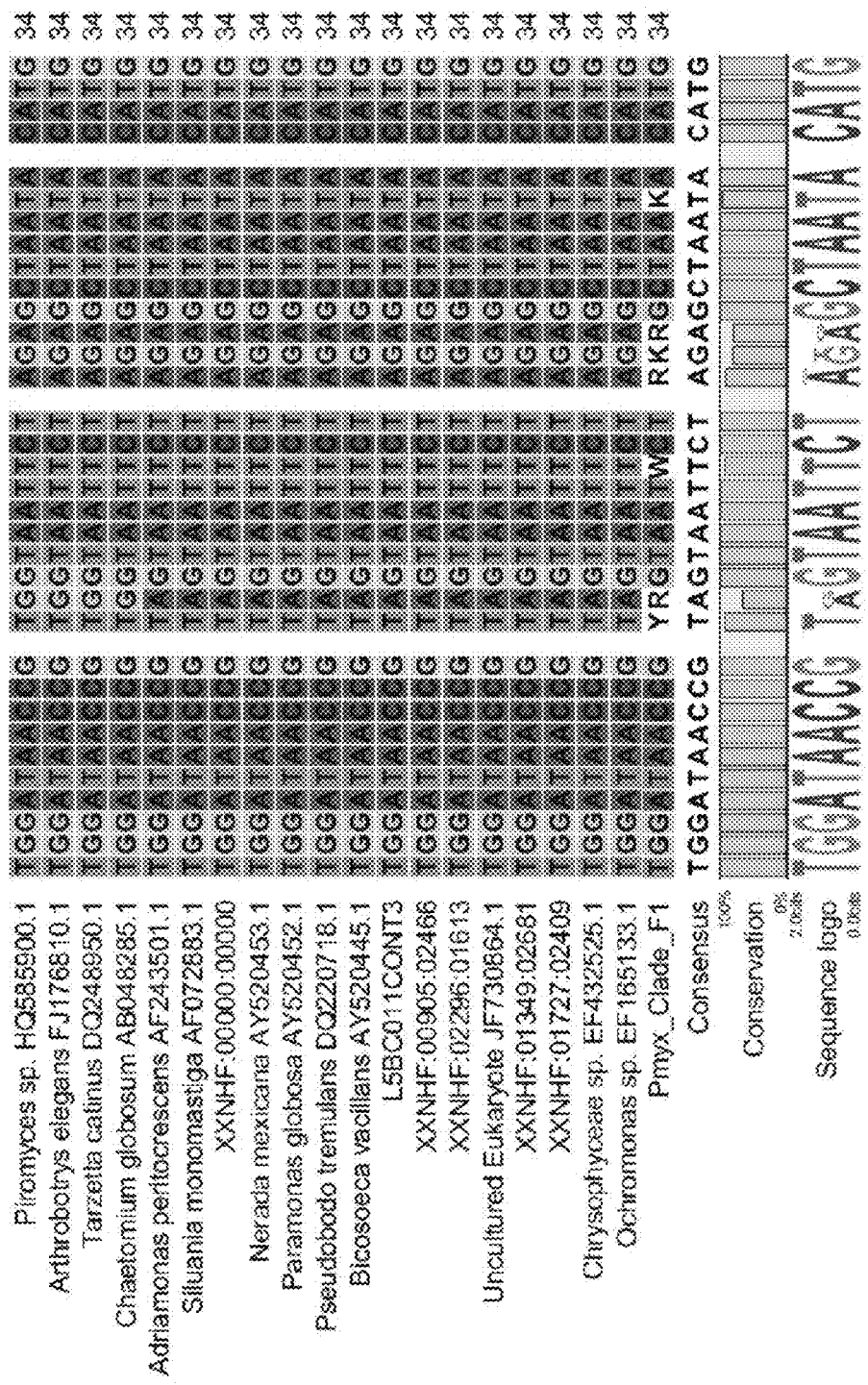
Figure 16E:
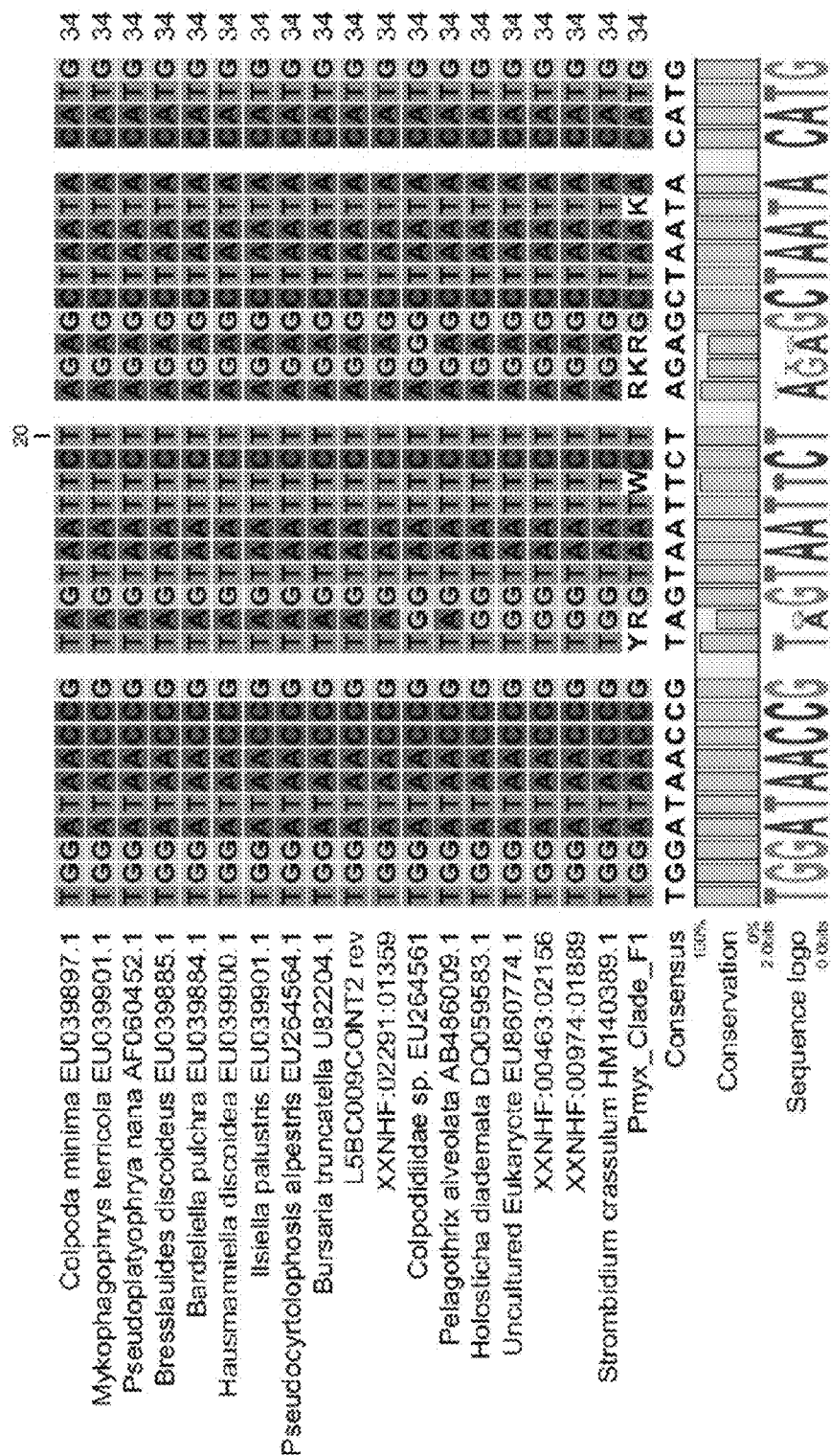
Figure 17A:
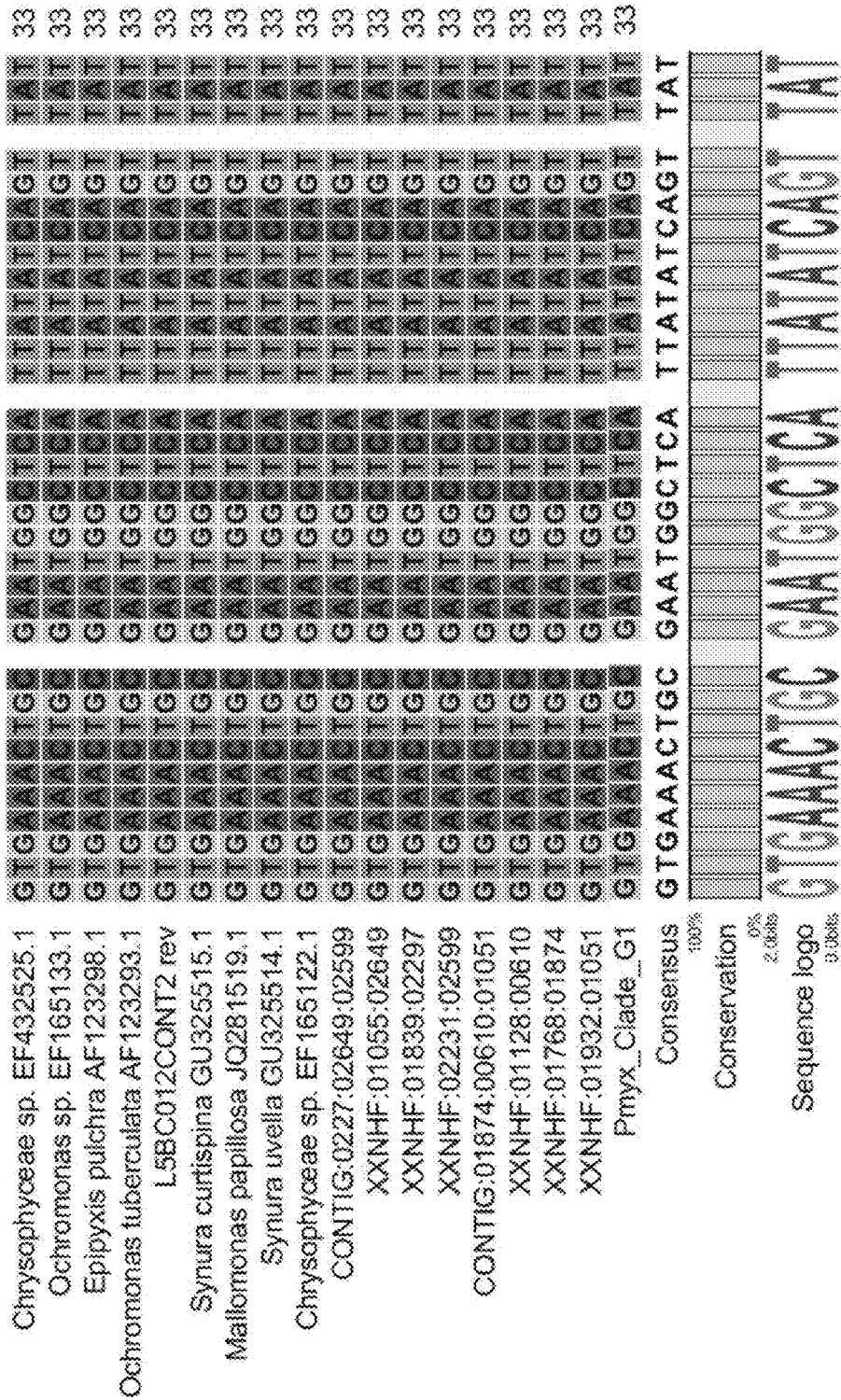
FIG. 17A-17B depict protozoal species detected with oligonucleotide probe Pmyx_Clade_G_Probe1 (aka Pmyx_Clade_G1 and G1).
Figure 17B:
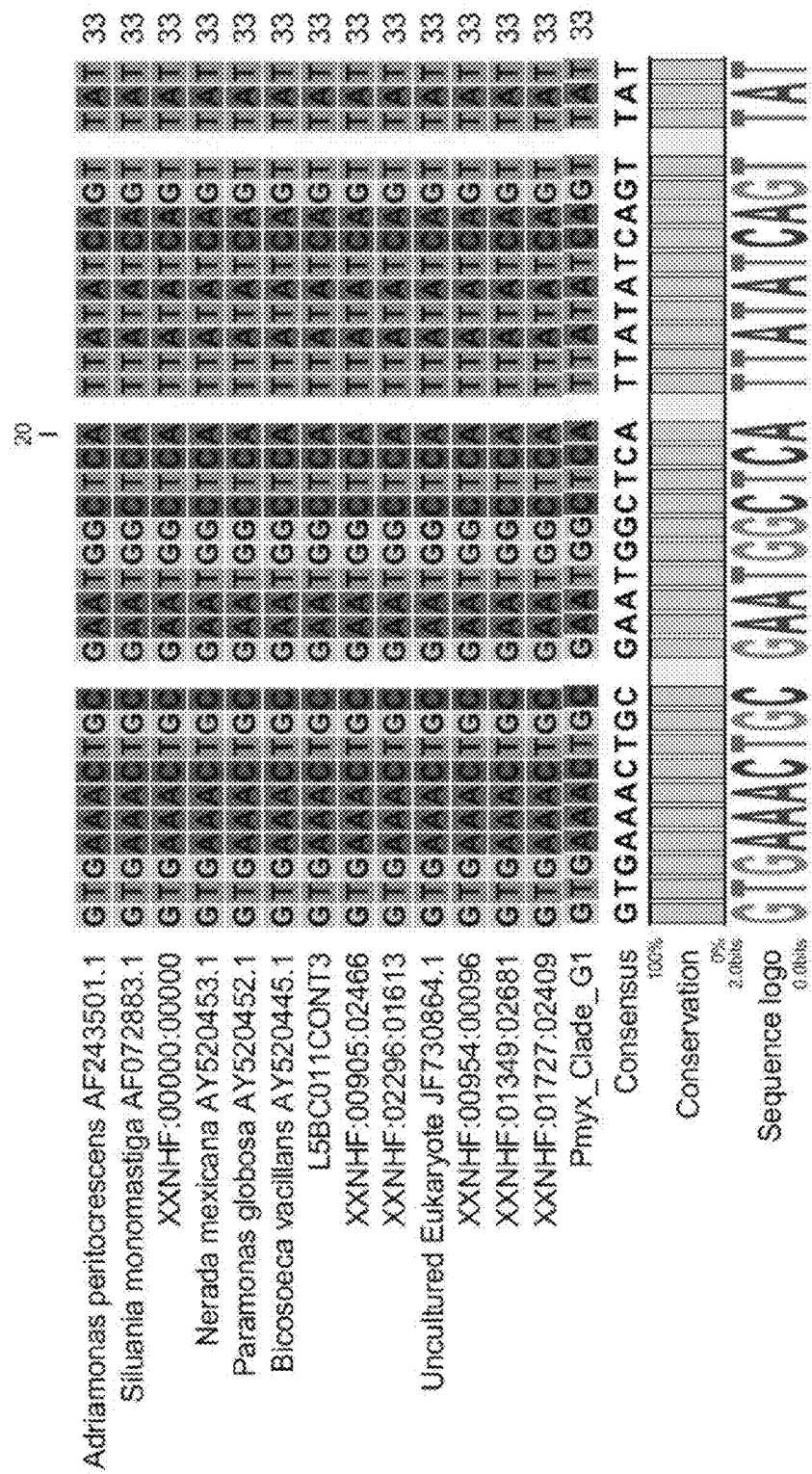
Figure 18A:
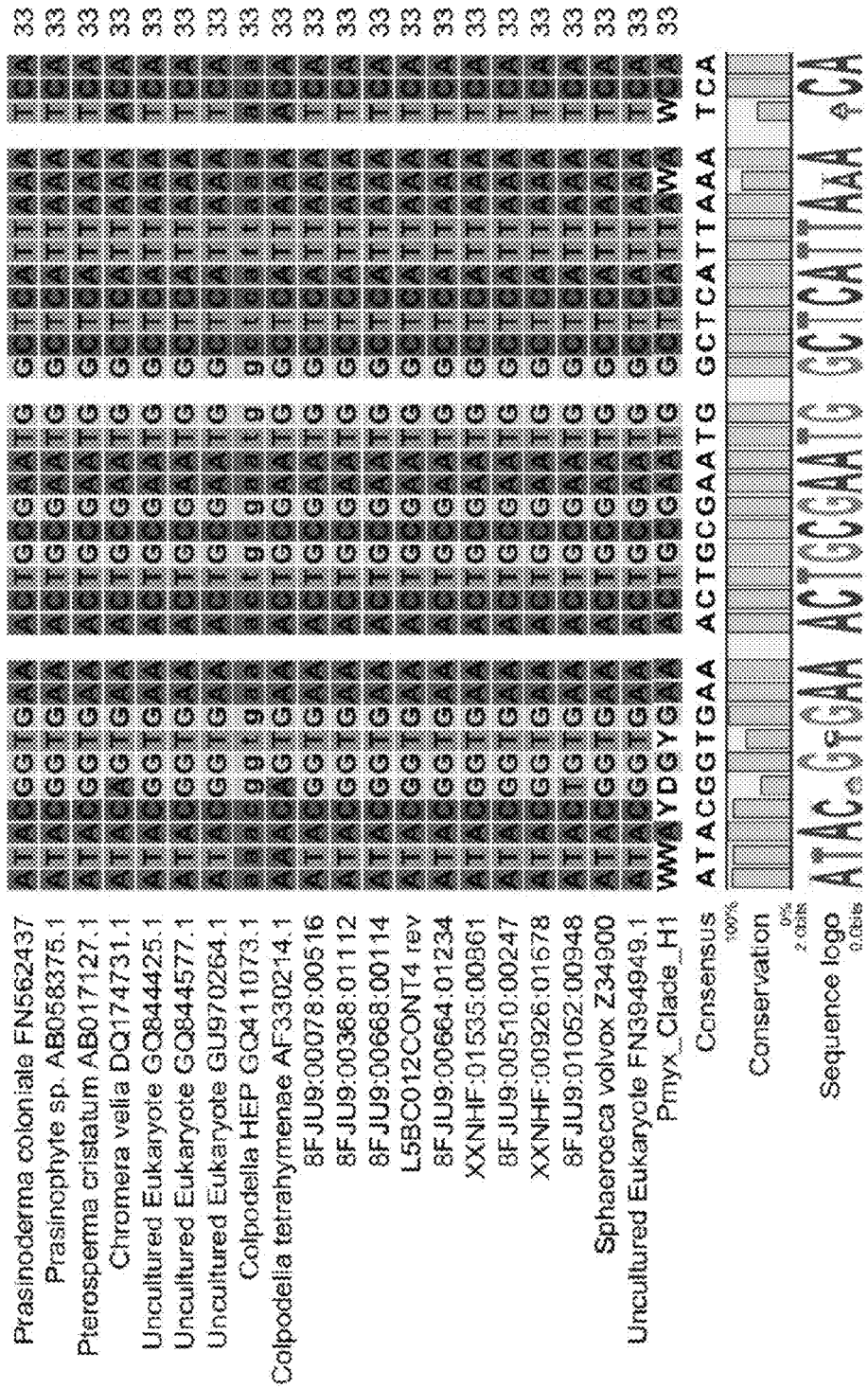
FIG. 18A-18E depicts protozoal species detected with oligonucleotide probe Pmyx_Clade_H_Probe1 (aka Pmyx_Clade_H1 and H1).
Figure 18B:
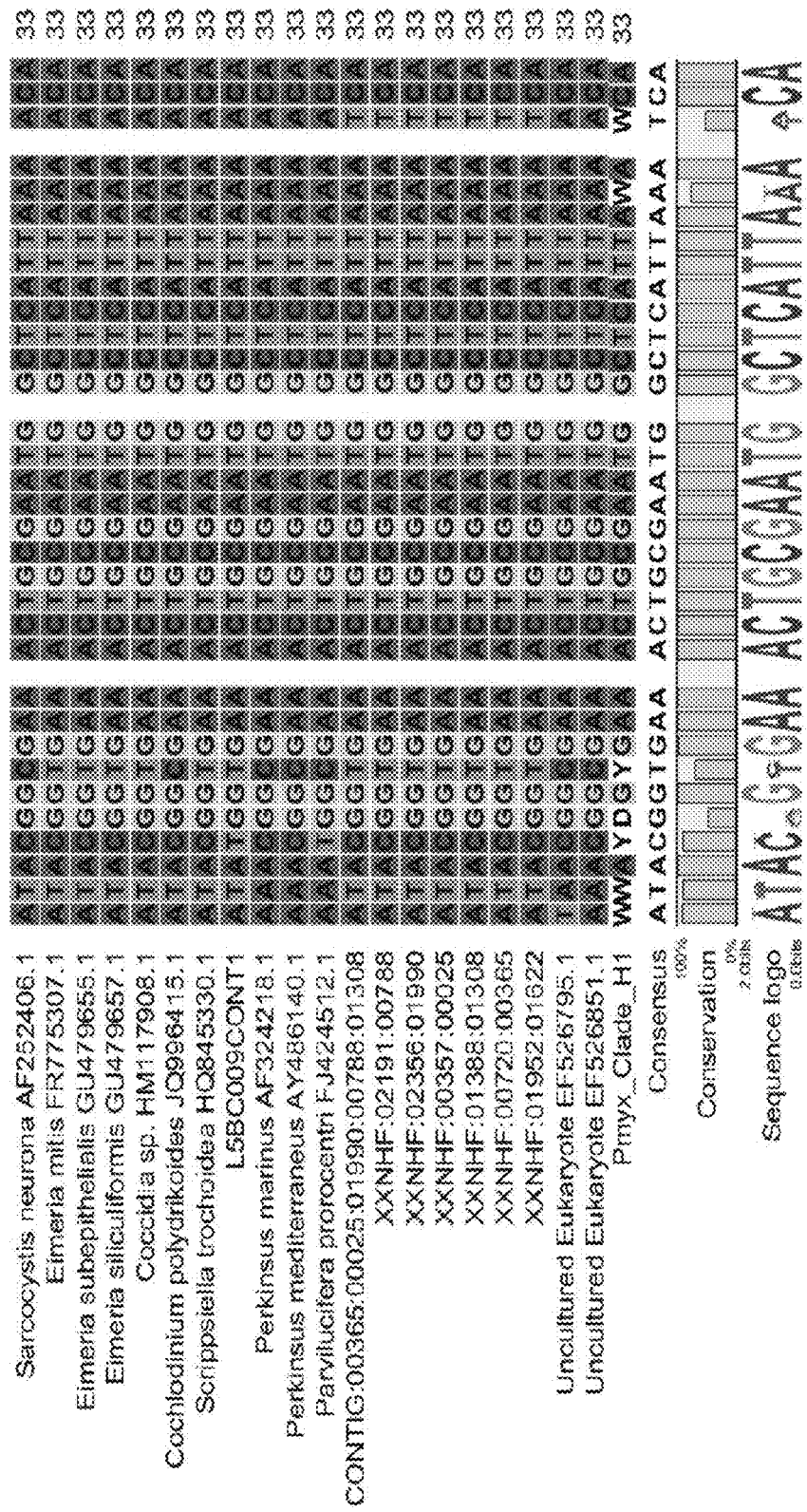
Figure 18C:
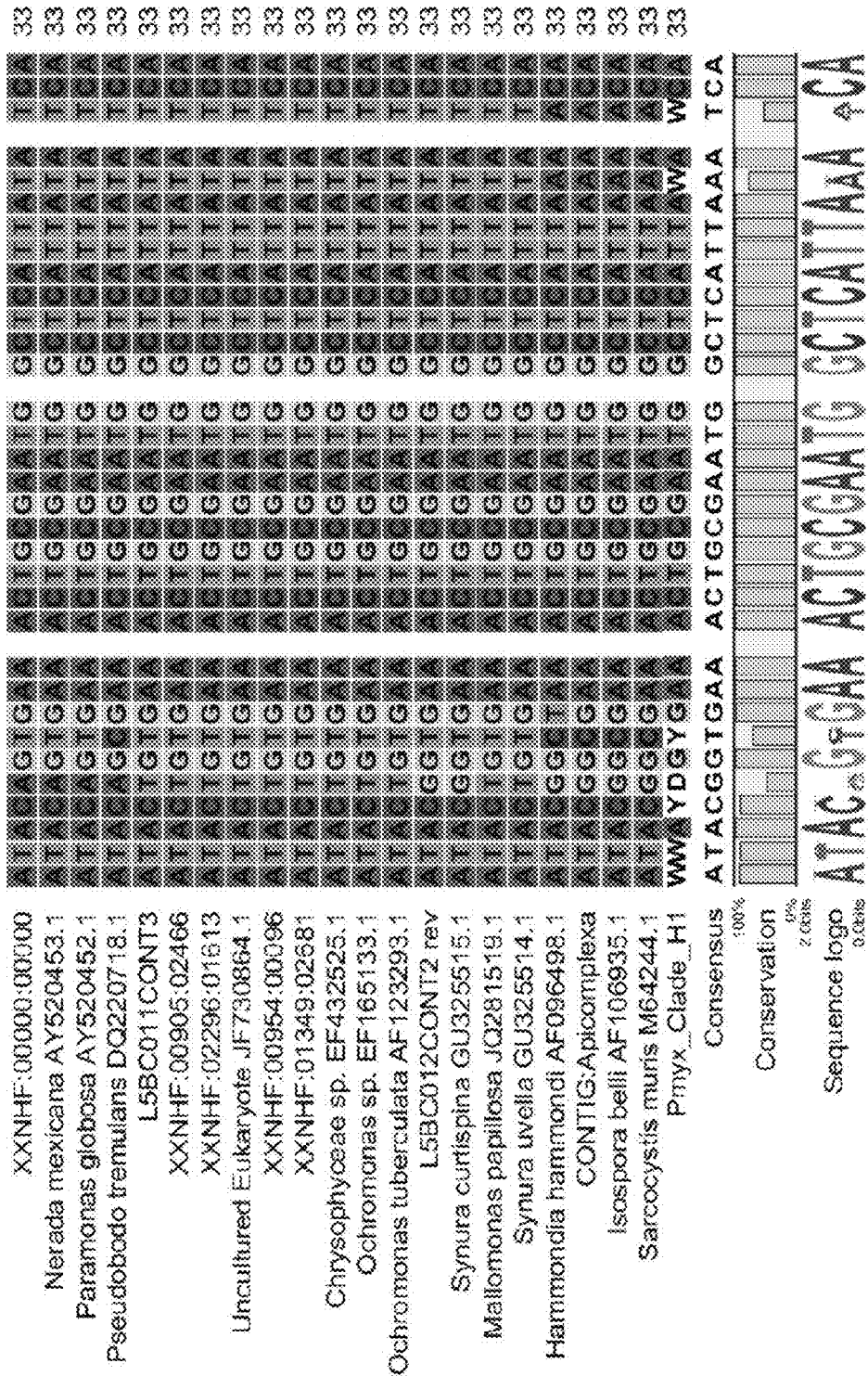
Figure 18D:
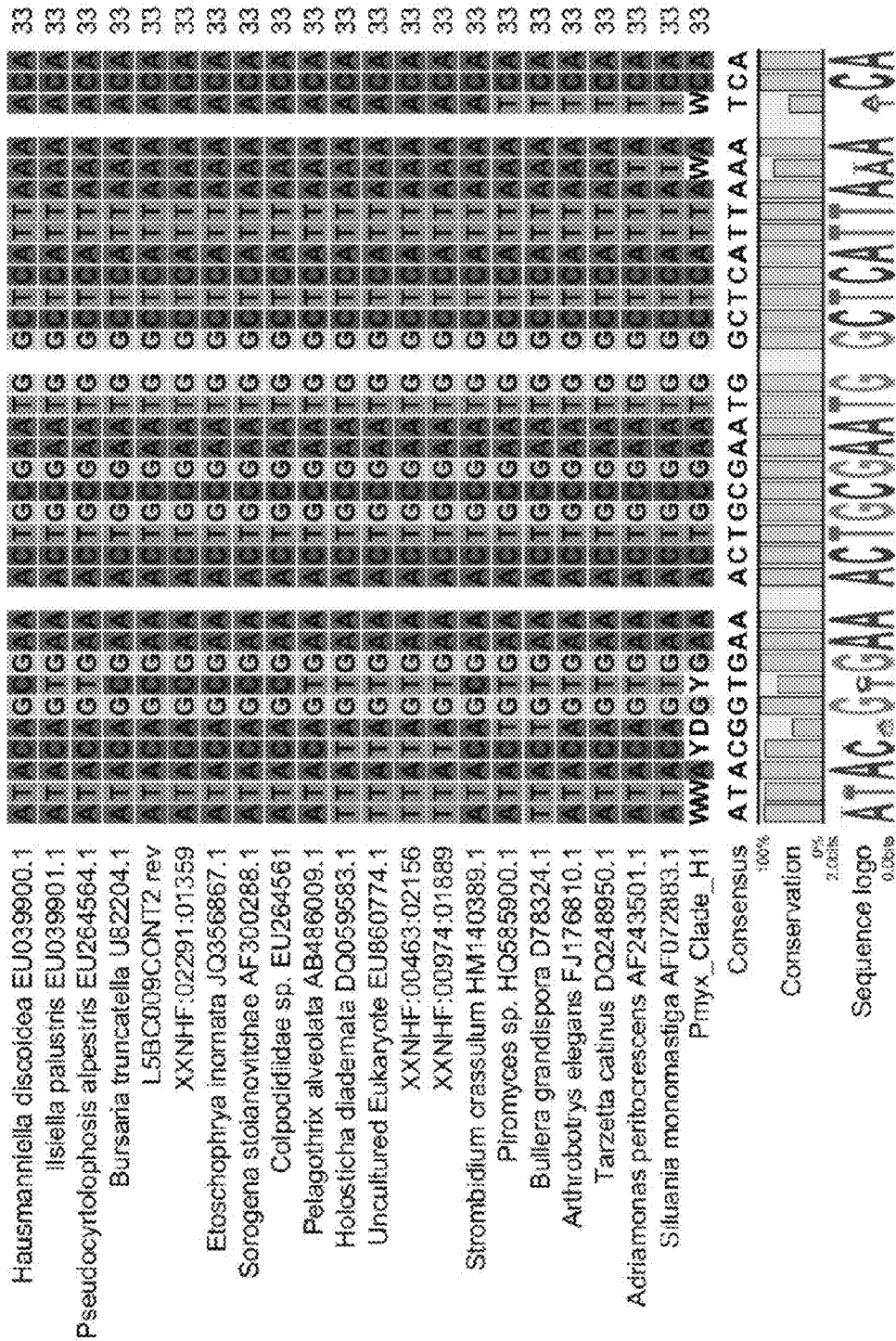
Figure 18E:
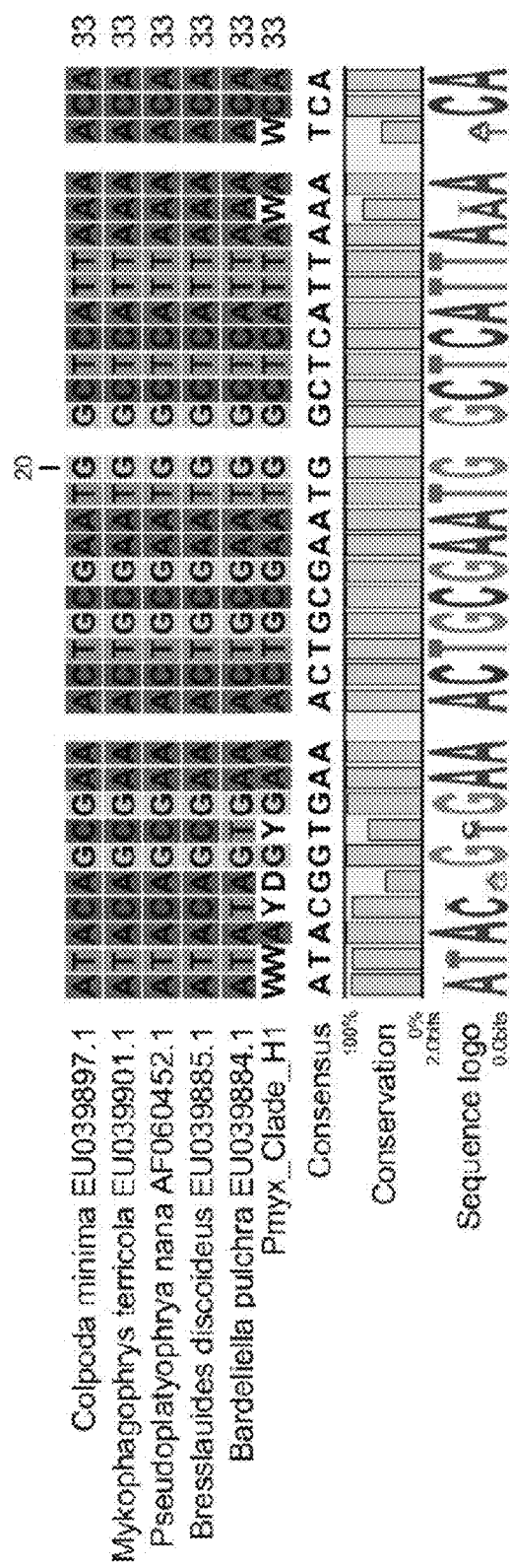
Figure 19A:
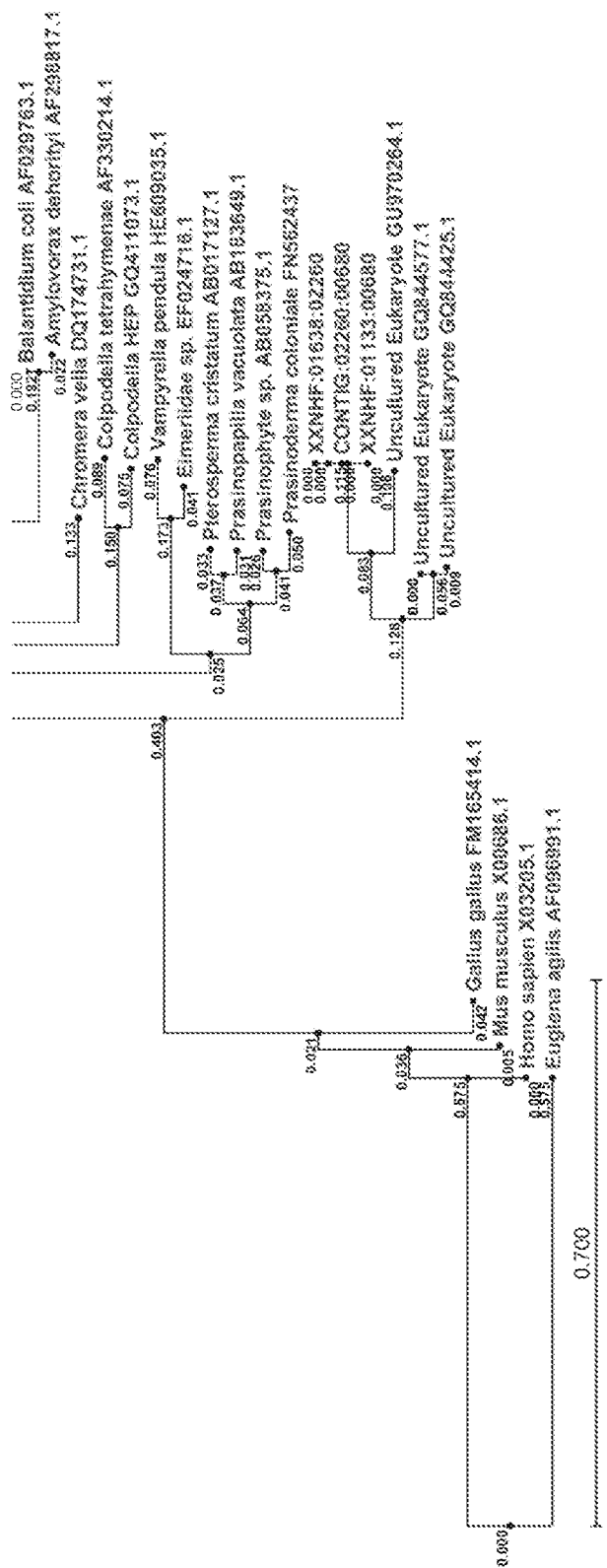
FIG. 19A-19G depicts a cladistics analysis using fungi, vertebrates, and Euglena to root the tree or cladogram at both ends. The cladogram indicates how the protozoal species detected by the oligonucleotide probes array across the chromalveolate group of protozoans.
Figure 19B:
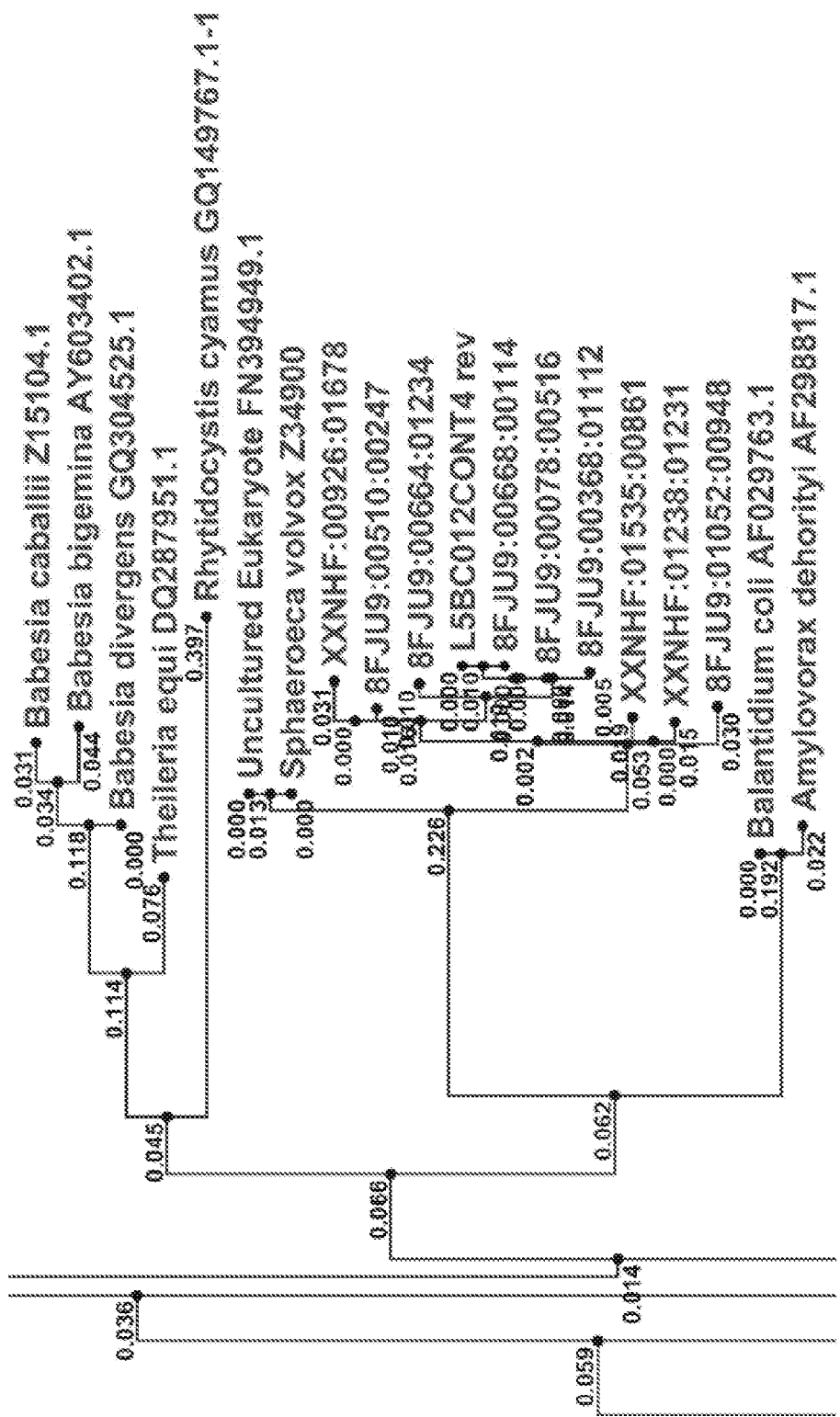
Figure 19C:
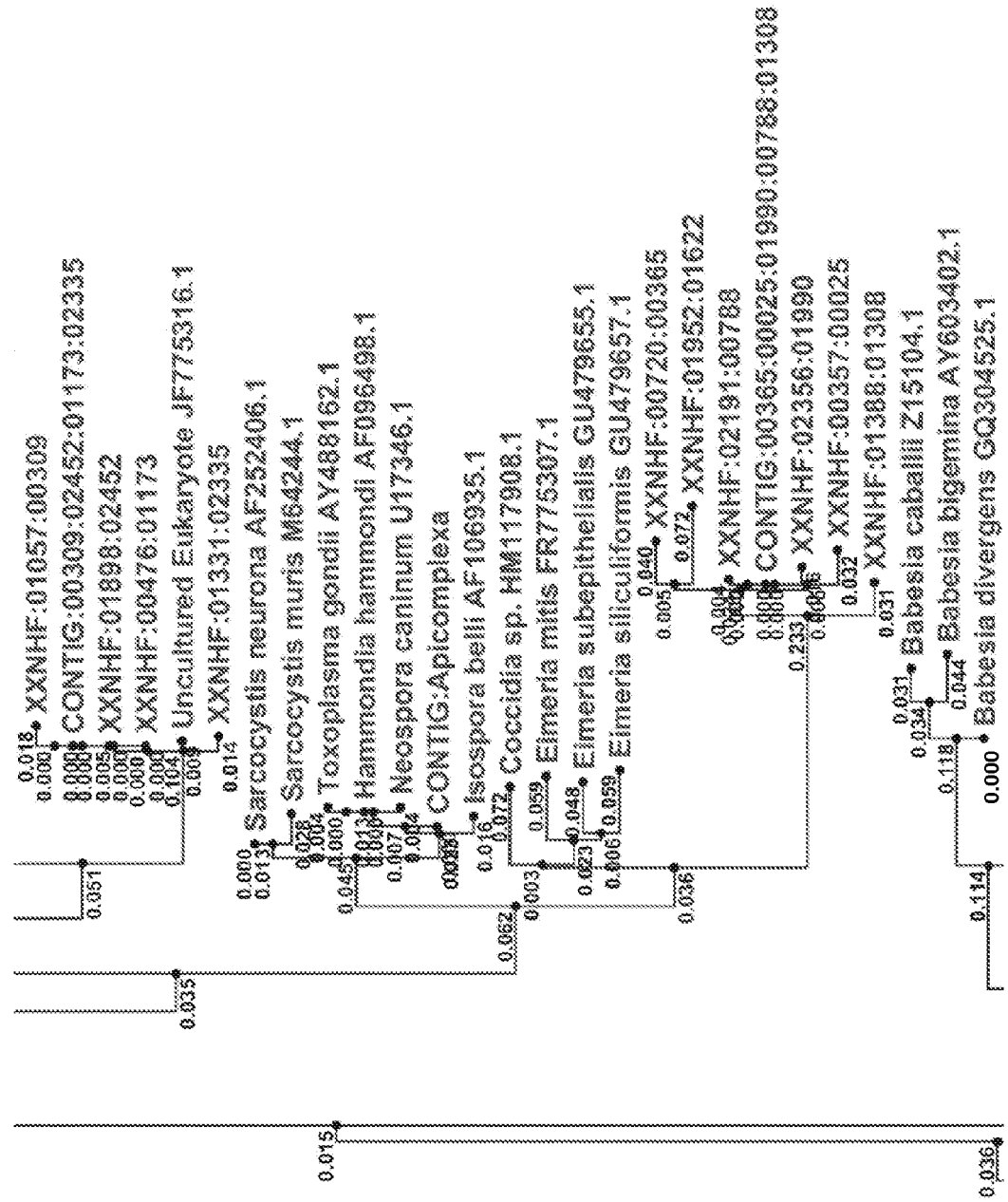
Figure 19D:
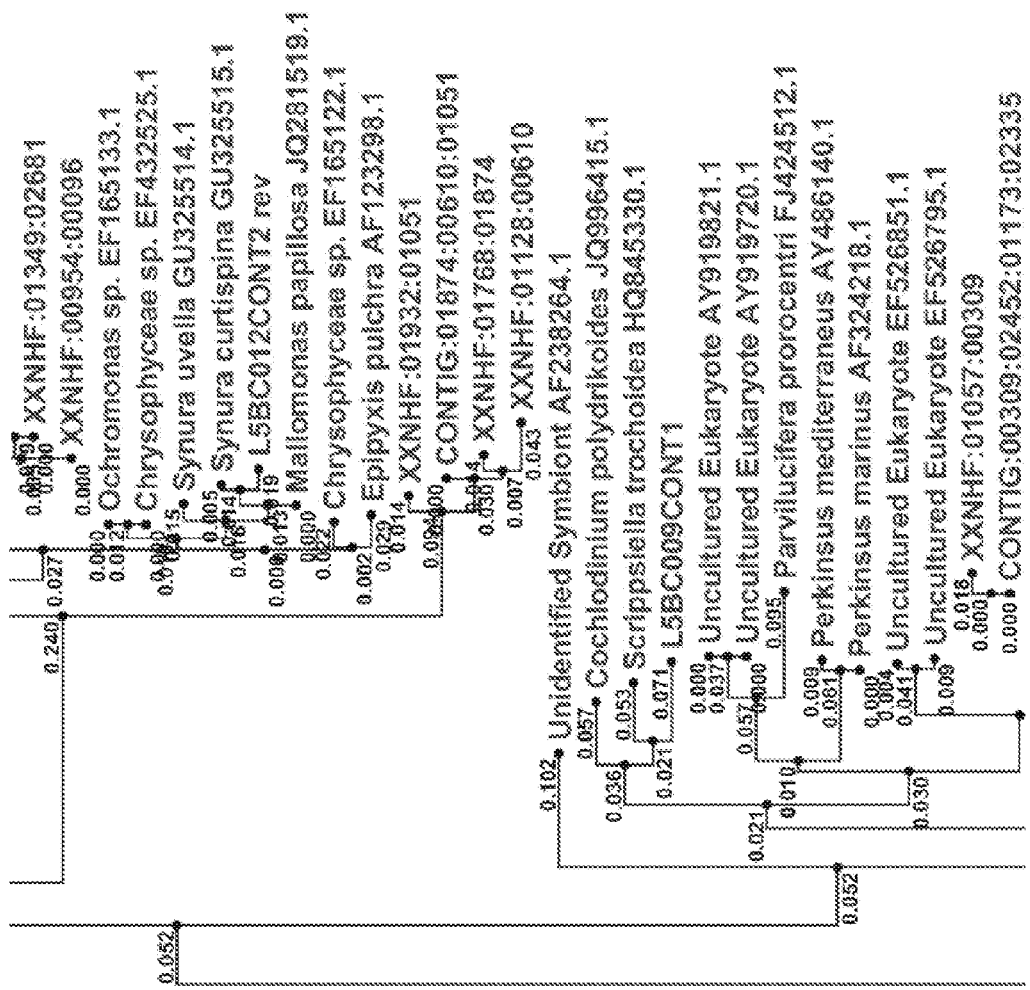
Figure 19E:
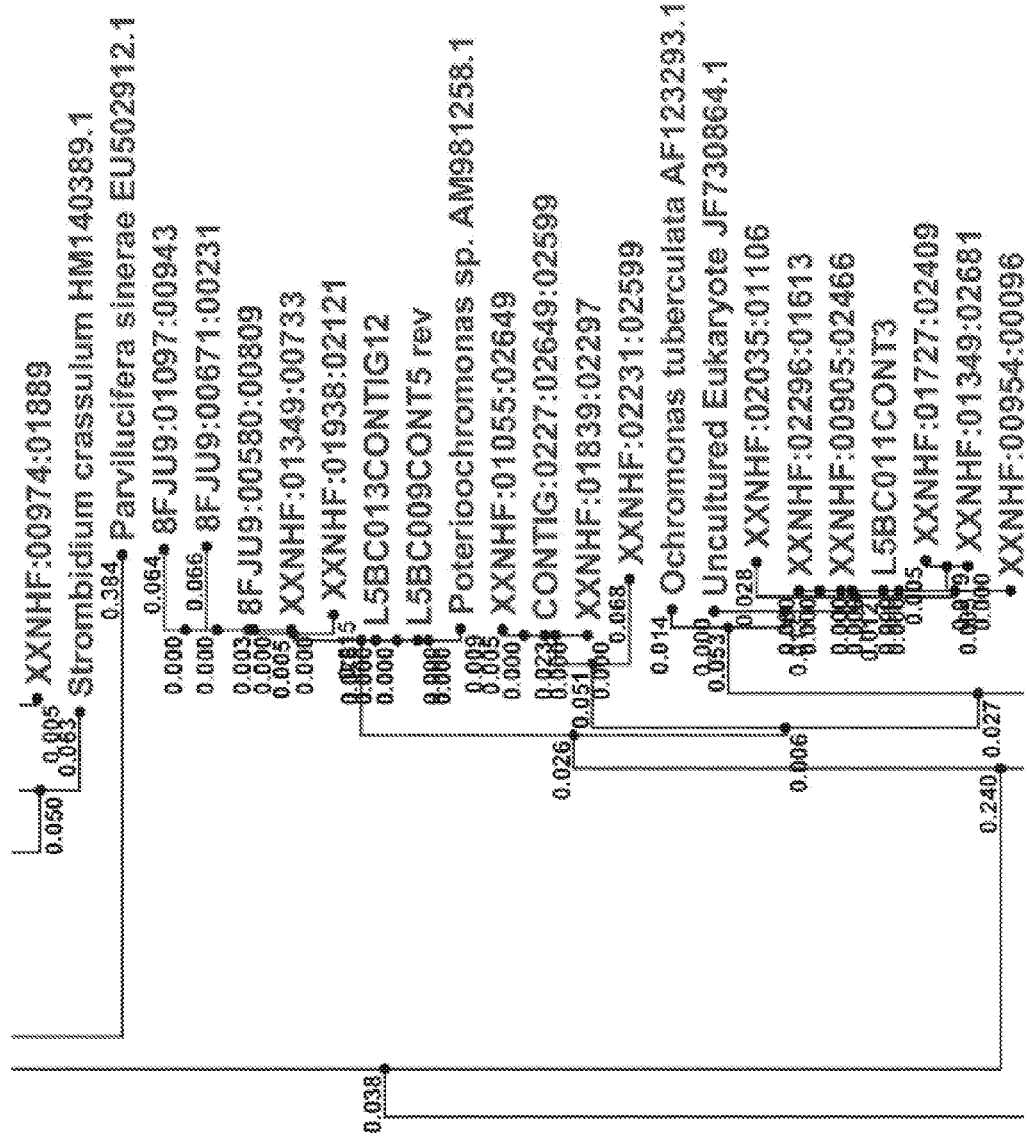
Figure 19F:
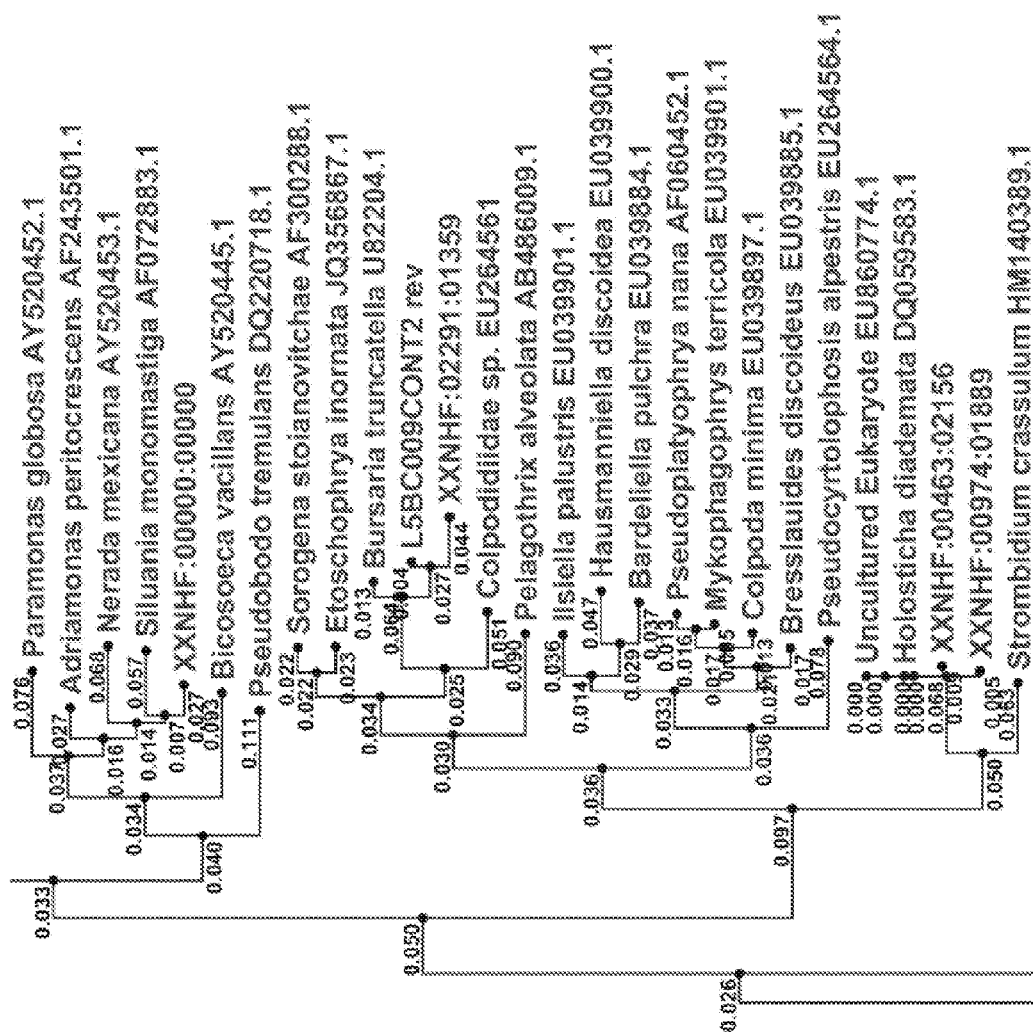
Figure 19G:

Microscopic study of stained blood smears from the 3 ALS patients revealed 1-2 μm diameter epierythrocytic bacteria, while fluorescent DNA staining techniques revealed large amorphous clusters, 20-100 μm in diameter, consisting of eukaryotic organisms, adherent lymphocytes, and bacteria (FIG. 1-*Cluster* fragment from ALS patient peripheral blood 1000×, excitation @ 620 nm; Ethidium Bromide and Höechst stain; visible are multiple organisms from coccobaciili to larger eukaryotic organisms representative of a complex biofilm community). Additionally, Höechst (FIG. 3) and PAS (FIG. 2) stains reveal that the extracellular matrix material associated with these clusters contain both DNA and polysaccharides. The morphology of these structures was consistent with what is observed in environmental biofilm communities. DNA extracted from peripheral blood was assessed by PCR using bacterial, fungal, and protozoan primers. Subsequent sequencing and analysis revealed a mixed population of organisms, including Proteobacteria (primarily *Ralstonia* spp.), fungi, and sequences suggestive of a novel protozoan species (Table 1 and FIG. 4). Microscopic observations combined with PCR results are consistent with a persistent biofilm community found in the peripheral blood of these patients with ALS.

Thus, observation under microscopy and PCR based methods are consistent with a protozoan foundation pathogen and primary biofilm former. It is believed that ALS may be caused by a foundation protozoan which produces a polysaccharide biofilm, hosting a communalistic environment for additional microorganisms. These clusters consist of a biofilm matrix and are freely circulating in the peripheral vascular system. Continued host lymphocytic response is evidenced by both PCR and microscopy. It is suspected that Fungi and *Proteobacteria* spp. are opportunistic members of this biofilm community. The postulated mechanism of disease is a gross obstructive sludging and macroscopic mechanical coagulation producing ischemia, retrograde venous flow, and poor nutrient supply to the surrounding tissues.

The concept of eukaryotic biofilms has been demonstrated recently in the case of the fungi *P. carinii* (6). Protozoan biofilms represent an emerging area in need of further study, particularly their role in ALS and other diseases.

References are as follows:
1. Bromberg M B. Pathogenesis of amyotrophic lateral sclerosis: a critical review. Curr Opin Neurol 1999; 12:581-588.
2. Ince P G, Lowe J, Shaw P J. Amyotrophic lateral sclerosis: current issues in classification, pathogenesis, and molecular pathology. Neuropathology and Applied Neurobiology 1998; 24:104-117.
3. Bancroft J D, Gamble M. Theory and practice of Histological Techniques, 6th ed. Philadelphia: Churchill Livingstone; 2007.
4. Willi B, Boretti F S, Tasker S, Meli M, Wengi N, et al. From Haemobartonella to hemoplasma: molecular methods provide new insights. Vet Microbiol 2007; 125:197-209.
5. Hall-Stoodley L, Stoodley P. Evolving concepts in biofilm infections. Cell Microbiol 2009; 11:1034-1043.
6. Cushion M T, Collins M S, Linke M J. Biofilm formation by *Pneumocystis* spp. Eukaryot Cell 2009; 8:197-206.

Example 2

*Protomyxzoa rheumatica*: A Novel Infectious Organism; Missing Etiology in Chronic Disease Rheumatic and inflammatory diseases have had a long history of links with infectious agents ranging from molecular mimicry effects to the direct activity of human pathogens. The following orphan diseases and conditions are of keen interest: Chronic Fatigue Syndrome; Fibromyalgia; Ulcerative Colitis; Gulf War Veterans Illness; Scleroderma; ALS (Lou Gehrig's Disease); Rheumatoid Arthritis; Parkinson's Disease; Osteoarthritis; Multiple Sclerosis; Crohn's Disease; and Autism.

Using a basic science approach and microscopic techniques *Protomyxzoa rheumatica* (See FIG. 1) was found in patients with a wide range of chronic diseases. It is believed that *Protomyxzoa rheumatica* is a novel hematologic biofilm-forming protozoan with Malaria-like and *Babesia*-like characteristics. *Protomyxzoa rheumatica* is primarily hematogenous, lipid loving, complex (probably 'Myxozoan'), and very drug resistant, but antiprotozoals and antihelminthics may be efficacious. Furthermore, research indicates that multiple species may be found cohabitating within the *Protomyxzoa rheumatica* biofilm. Biofilm communities with *Protomyxzoa rheumatica* as the foundation pathogen cause gross obstructive sludging resulting in macroscopic mechanical coagulation and retrograde venous flow. This results in ischemia and poor nutrient supply to surrounding tissues and chronic infection (chronic inflammatory response by lymphocytes).

Thus, initial results indicate that a variety of pathogenic bacteria and potential viruses are harbored within the biofilm matrix and may be pathogenic factors. Results are consistent with this novel organism having profound biofilm forming properties that are likely related to observed clinical significance in patients with chronic inflammatory diseases. It is not difficult to hypothesize that deficits in blood perfusion may contribute or exacerbate symptoms in these patients.

The work disclosed herein has transitioned from merely microscopic study to molecular characterization and genomic sequencing of *Protomyxzoa rheumatica*. The existence of *Protomyxzoa rheumatica* and continued study may be critically important to the treatment and outcome of patients with chronic inflammatory and neurologic diseases.

Advanced Detection

First, research microscopic techniques that were instrumental in the discovery of *Protomyxzoa rheumatica* have been adapted for use as a clinical diagnostic assay. A proprietary Advanced Stain test is not only specifically designed to detect biofilm based infections in aqueous samples, but it has been rigorously shown to detect known pathogens from bacterial infections, to disseminated fungal infections, to protozoans such as Malaria and *Babesia*. The principle of this assay relies on the simple fact that infectious organisms have DNA. By adding specific DNA dye to the samples coupled with fluorescent microscopy, a direct visualization of hematologic infections can be documented for health care professional and physician use. Blood samples are particularly well suited for this type of staining technique because red blood cells do not have nuclear DNA, thus appearing as a dark backdrop against infectious organisms that shine brightly, with the patient white blood cells providing an excellent internal control for staining quality.

In addition to microscopy-based detection of biofilms by an Advanced Stain test, a *Protomyxzoa rheumatica* PCR based test can be used. This assay provides information about the detectable levels of *Protomyxzoa rheumatica* in a patient sample.

This suite of tools will assist health care professionals to accurately identify, monitor, and treat patients found to harbor *Protomyxzoa rheumatica*.

Example 3

Real Time Quantitative PCR to Detect *Protomyxzoa rheumatica* (FL1953)

For the exemplary purposes of this disclosure, as one example, the following 429 base pair sequence (SEQ ID NO: 1) from the protozoan pathogen *Protomyxzoa rheumatica* species can be detected by real time quantitative PCR using the following primers and probe to amplify and detect a 153 base pair fragment with the following PCR conditions.

```
                                                  SEQ ID NO: 1
CCATGCATGT CTAAGTATAA GCACTTATAC AGTGAAACTG CGAATGGCTC 50

ATTATATCAG TTATAGTTTA TTTGATAGTC CCTACTACTT GGATAACCGT 100

AGTAATTCTA GAGCTAATAC ATGCGCTAAC TCCTGACCTC ACGGAAAGGA 150

TGTATTTATT AGATACAACC AACCTTGTTT GGTGAATCAT AATAACTGAG 200

CGAACCGCAT GCTTCGGCGG CGGTGGTTCA TTCAAGTTTC TGACCTATCA 250

GCTTTCGATG GTAGGGTATT GGCCTACCAT GGCGTTAACG GGTAACGGAG 300

AATTAGGGTT CGATTCCGGA GAGGGAGCCT GAGAGATGGC TACCACATCC 350

AAGGAAGGCA GCAGGCGCGT AAATTACCCA ATCCTGACAC AGGGAGGTAG 400

TGACAAGAAA TAACAATGCG GAGCCTTCG 429

Forward Primer                                      (SEQ ID NO: 2)
FL1953_F2(5'-ATGGCTCATTATATCAGTTATAGT-3')

Reverse Primer                                      (SEQ ID NO: 3)
FL1953_R1(5'-GTTATTATGATTCACCAAACAAG-3')

Probe                                               (SEQ ID NO: 4)
FL1953_PROBE(5'-FAM-ACATCCTTT/ZEN/CCGTGAGGTCAGGAGTT-
3IABkFQ-3')
```

The PCR conditions are as follows:
37° C. 15 min
95° C. 10 min
50 cycles of: 95° C. 30 sec; 60° C. 1 min; 72° C. 30 sec

Example 4

Standard PCR and Gel Electrophoresis to Detect *Protomyxzoa rheumatica* (FL1953)

For the exemplary purposes of this disclosure, as another example, standard PCR using the following primers can amplify a 196 base pair fragment also for the sequence above (SEQ ID NO: 1) that can be visualized by gel electrophoresis. Primers for Standard PCR:

```
Forward Primer                          (SEQ ID NO: 5)
FL1953_F1 (5'-CCATGCATGTCTAAGTATA-3')

Reverse Primer                          (SEQ ID NO: 3)
FL1953_R1 (5'-GTTATTATGATTCACCAAACAAG-3')
```

Gel electrophoresis is a technique that is well known in the art. As a non-limiting example, PCR products may be visualized by 2% agarose gel electrophoresis using Tris-acetate acid buffer (1×TAE) run at room temperature. The gel may be stained by ethidium bromide and exposed by UV for imaging.

Example 5

Detection of *Protomyxzoa rheumatica* (FL1953) by Expended Extraction, Sample Enrichment, and PCR By way of other examples, the detection of *Protomyxzoa rheumatica* by PCR can be achieved by the following methods:

A. An expanded extraction followed by a *Protomyxzoa rheumatica* specific PCR;

B. A sample enrichment and subsequent expanded extraction followed by a *Protomyxzoa rheumatica* specific PCR; and C. *Protomyxzoa rheumatica* specific PCR.

A. Expanded Extraction Method The following expanded extraction procedure is an "extreme" extraction procedure referenced herein as the "Expanded Extraction Method". Most other organisms and DNA would be destroyed.

This method also requires the *Protomyxzoa rheumatica* specific PCR discussed below in section C. for reproducible detection of the *Protomyxzoa rheumatica* genomic fragment.

The steps are as follows:

1. 750 µL of Qiagen Buffer AL is measured using a P1000 and dispensed into a labeled Zymo Research ZR Bashing Bead Lysis Tube.
2. Next, 200 µL of whole EDTA preserved blood is measured using a P200 and added to the same tube.
3. The screw cap of the Bashing Bead Lysis Tube is secured tightly and the sample is briefly vortexed.
4. The sample is placed in a centrifuge and briefly spun at 8000 rpm (~6000 g) to remove solution from the screw cap.
5. 40 µL of reconstituted Proteinase K (>600 mAU/mL) is added to the sample in the Bashing Bead Lysis Tube. Note: The brand of Proteinase K does not appear to make any difference on efficiency of extraction and Qiagen's proprietary Protease may be substituted in most circumstances.
6. The screw cap of the Bashing Bead Lysis Tube is secured tightly and the sample is briefly vortexed.
7. The sample is then incubated for 5 minutes at 56° C. on a heating block.
8. The sample is then vortexed at maximum speed for 30 second.
9. The sample is then incubated for 5 minutes at 56° C. on a heating block.
10. The sample is then vortexed at maximum speed for 5 second.
11. The sample is allowed to rest for 5 second at room temperature.
12. Steps 10 and 11 are repeated 5 times. Proceed to step 13 after the final repetition of step 11.
13. The sample is then incubated for 2 minutes at 56° C. on a heating block.
14. The sample is then vortexed at maximum speed for 5 minutes using a tube holder.
15. The sample is then incubated for 5 minutes at 56° C. on a heating block.
16. The sample is then vortexed at maximum speed for 1 minute.
17. The sample is then incubated for 5 minutes at 56° C. on a heating block.
18. The sample is then vortexed at maximum speed for 1 minute. Note: Additional vortexing and incubation steps may improve sample recovery, but the preceding steps represent a minimal series of steps.
19. The sample is placed in a centrifuge and briefly spun at 8000 rpm (~6000 g) to remove solution from the screw cap.
20. Prepare a Zymo Research Zymo-Spin IV Spin Filter by snapping off and removing the flow through plug, place the Spin Filter into the provided collection tube, and label the accompanying orange screw cap.
21. 600 µL of the sample is decanted using a P1000 and dispensed into the Spin Filter and the accompanying orange screw cap should be affixed securely. Note: Avoid aspirating beads from the Bashing Bead Lysis tube by moving the tip in a circular motion while decanting the sample as the beads may block the pipette tip from functioning.
22. The Spin Filter is placed in a centrifuge and spun at 8000 rpm (~6000 g) for 1 minute.
23. 300 µL of molecular biology grade 100% ethanol is added to the resulting flow through in the collection tube and mixed by repeated pipetting.
24. 700 µL of the flow though and ethanol mix is added to a labeled QIAamp Mini Spin Column (in a 2 mL collection tube) using a P1000 without wetting the rim.
25. The cap is gently closed and the tube is placed in a centrifuge and spun at 8000 rpm (~6000 g) for 1 minute.
26. The Spin Column is placed in a new 2 mL collection tube and the old collection tube with resulting filtrate is discarded.
27. The Spin Column is gently opened and 500 µL of Buffer AW1 is added using a P1000 without wetting the rim.
28. The cap is gently closed and the tube is place in a centrifuge and spun at 8000 rpm (~6000 g) for 1 minute.
29. The Spin Column is placed in a new 2 mL collection tube and the old collection tube with resulting filtrate is discarded.
30. The Spin Column is gently opened and 500 µL of Buffer AW2 is added using a P1000 without wetting the rim.
31. The cap is gently closed and the tube is placed in a centrifuge and spun at maximum rpm (~20,000 g) for 1 minute.
32. The Spin Column is placed in a new 1.5 mL microcentrifuge tube and the old collection tube with resulting filtrate is discarded.
33. 30 µL of Buffer AE is added to the Spin Column and incubated for 2 minutes at room temperature. Note: Alteration of elution volume may increase template concentration.
34. After incubation the sample is placed in a centrifuge and spun at 8000 rpm (~6000 g) for 1 minute.
35. The Spin Column is discarded. The resulting labeled and dated tube contains purified DNA from the starting blood sample.
36. The sample concentration may be determined by Nano-Drop or traditional spectrophotometer methods. Note: Expected concentration ranges between 5 ng/µL to 50 ng/µL, depending on the state and quality of the blood sample.
37. For short term storage the DNA sample may be kept at −20° C. For long term storage the DNA sample should be kept at −70° C.
38. Proceed to section C. below for PCR conditions and methods.

B. Combined Sample Enrichment and Expanded Extraction Method

This method requires both a sample enrichment method and expanded extraction method as discussed above in section A. in addition to the *Protomyxzoa rheumatica* specific PCR discussed below in section C. for reproducible detection of the *Protomyxzoa rheumatica* genomic fragment. This method is referenced herein as the "Combined Sample Enrichment and Expanded Extraction Method."

The steps are as follows:

1. Measure out 1.5 mL of well mixed human blood (EDTA preserved blood, although other blood preservation methods and possibly serum may work) into a new labeled 1.5 mL Eppendorf tube.
2. Place the tube into the microcentrifuge and spin at 300 g for 15 minutes.
3. Carefully remove tube and decant the supernatant off the sample into a new labeled 1.5 mL Eppendorf tube using a P200. Be careful not to aspirate any of the blood cells. Leaving some of the supernatant reduces the introduction of any blood cells.
4. Place the tube into the microcentrifuge and spin at 14,000 or maximum g for 10 minutes.

5. Carefully remove the tube and decant the supernatant off the pellet. Be careful to not disturb the pellet that formed in the bottom of the tube. Discard the supernatant.

6. Add 200 μL of molecular biology grade water to the pellet and pulse vortex until the pellet is fully resuspended.

7. 750 μL of Qiagen Buffer AL is measured using a P1000 and dispensed into a labeled Zymo Research ZR Bashing Bead Lysis Tube.

8. All 200 μL of the resuspended sample is added to the same tube.

9. Follow steps #3 to #38 in Section A. discussed above.

C. *Protomyxzoa rheumatica* PCR Detection Method

This method is used for reproducible detection of the *Protomyxzoa rheumatica* genomic fragment. The steps are as follows:

1. A master mix is formulated using the following reagents added in the following order in the listed volumes per 10 μL reaction using standard PCR techniques.
   i. 3.48 μL of H2O
   ii. 5 μL of Sigma Extract-N-Amp Enzyme Mix
   iii. 0.26 μL of FL1953_F1 primer (5'-CCATGCAT-GTCTAAGTATA-3') (SEQ ID NO: 5)
   iv. 0.26 μL of FL1953_R1 primer (5'-GTTATTATGAT-TCACCAAACAAG-3') (SEQ ID NO: 3)

2. Once the master mix is thoroughly mixed and dispensed into individual PCR tubes 1 μL of the extracted DNA sample from either Section A. or Section B. above is added to each PCR tube with one negative control per 10 samples and minimally one positive control. Note: It is highly recommended that a separate set of PCRs accompany these samples using a pair of universal primers, such as 18S, to ensure that PCR inhibitors are not present in the sample.

3. The resulting 10 μL volume is thoroughly mixed and placed in a validated PCR thermocycler using the following PCR reaction conditions:
   i. 95° C. for 2 minutes
   ii. 95° C. for 30 seconds
   iii. 55° C. for 30 seconds
   iv. 72° C. for 20 seconds
   v. Repeat steps ii, iii, and iv 50 times
   vi. 72° C. for 7 minutes
   vii. Hold at 4° C., until sample is to be analyzed 4. Resulting PCR products are visualized by gel electrophoresis on a 2% gel and stained with ethidium bromide. A positive result corresponds to a band that migrates at approximately 190 bp identically with the positive control band. Negative samples should be re-extracted by methods in Section A. or Section B. above and tested again by PCR to confirm the negative result.

Example 6

A Semi-Pan-Protozoal Quantitative PCR (qPCR) Assay

The Semi-Pan-Protozoal qPCR conditions are as follows:

| Primers: | |
|---|---|
| Protozoal_F (forward primer)<br>CCATGCATGTCTAAGTATAAGC | (SEQ ID NO: 6) |
| Protozoal_R (reverse primer)<br>CAGAAACTTGAATGATCTATCG | (SEQ ID NO: 7) |

| Thermocycler Conditions: | | | |
|---|---|---|---|
| Step # | Temp | Time | Notes |
| 1) | 95° C. | 10 minutes | |
| 2) | 95° C. | 30 seconds | |
| 3) | 50° C. | 1 minute | Measure Endpoint |
| 4) | 72° C. | 30 seconds | |
| 5) | — | — | Repeat 2-4 50x |
| 6) | 25° C. | Indefinitely | |

| Probes: | |
|---|---|
| Pmyx_Clade_A_Probe1 (ROX) (aka A1)<br>/56-ROXN/GGATAACCGTAGTAATTCTGGAGCTAATACAT/3IABRQSp/ | (SEQ ID NO: 8) |
| Pmyx_Clade_B_Probe1 (HEX) (aka B1)<br>/HEX/TAAACTRTA/ZEN/ACTGWTWTAATGAGCYWTYCGCAGTTTY/3IABkFQ/ | (SEQ ID NO: 9) |
| Pmyx_Clade_C_Probe2 (Cy3) (aka C2)<br>/5Cy3/GGAGCTAATACATGATACAGGACCCG/3IAbRQSp/ | SEQ ID NO: 10) |
| Pmyx_Clade_D_Probe1 (Cy3) (aka D1)<br>/5Cy3/GAATGGCTCATTAWAWCAGTTAYAGTTTATTTGATGAT/3IAbRQSp/ | (SEQ ID NO: 11) |
| Pmyx_Clade_E_Probe1 (FAM) (aka E1)<br>/56-FAM/CTACGTGGATAACTGTAGTAATTCTAGAGCTAA/3IABkFQ/ | (SEQ ID NO: 12) |
| Pmyx_Clade_E_Probe2 (FAM) (aka E2)<br>/56-FAM/TTATTTGAT/ZEN/GGTTTYYTACTTGGATAACCCGAGT/3IABkFQ/ | (SEQ ID NO: 13) |
| Pmyx_Clade_E_Probe3 (Cy5) (aka E3)<br>/5Cy5/CTCTGGCTAATATACGCTGAAGACC/3IAbRQSp/ | (SEQ ID NO: 14) |
| Pmyx_Clade_F_Probe1 (Cy5) (aka F1)<br>/5Cy5/TGGATAACCGYRGTAATWCTRKRGCTAAKACATG/3IAbRQSp/ | (SEQ ID NO: 15) |

| Probes: | |
|---|---|
| Pmyx_Clade_G_Probe1 (Cy5) (aka G1)<br>/5Cy5/GTGAAACTGCGAATGGCTCATTATATCAGTTAT/3IAbRQSp/ | (SEQ ID NO: 16) |
| Pmyx_Clade_H_Probe1 (FAM) (aka H1)<br>/56-FAM/WAYDGYGAA/ZEN/ACTGCGAATGGCTCATTAWAWCA/<br>3IABkFQ/ | (SEQ ID NO: 17) |

Example 7

Analysis of Patient Samples with the Semi-Pan-Protozoal qPCR Assay

The qPCR assay described in Example 6 was used to analyze two patient samples (FL-A and FL-B). Positive control (+Ctrl) and negative control (−Ctrl) samples were included in the analysis. The positive control sample contained nucleic acids known to be amplified and recognized by the 166_Probe (aka FL1953_PROBE or 166), Pmyx_Clade_A_Probe1 (A1), Pmyx_Clade_B_Probe1 (B1), and Pmyx_Clade_H_Probe1 (H1) probes. Amplification of an endogenous control, β-actin, was performed to standardize the amount of sample DNA added to the reactions.

The results of the qPCR assay are shown in FIG. 8. The Ct values shown in the bottom row in FIG. 8 are examples of possible threshold cycle values that can be used with the disclosed assay. Reasonable variations of these Ct values can be used to achieve similar results.

The FL-A patient sample was positive with the A1, B1, G1, and H1 probes, and the FL-B patient sample was positive for the A1, E1, F1, and H1, probes. By comparing the sequences of the oligonucleotide probes to known protozoal genomic sequences, the pathogenic protozoans were tentatively identified in the patient samples. Alignments of the oligonucleotide probes with known protozoal genomic sequences are shown in FIG. 9-FIG. 18. The 166 probe is only known to detect *Protomyxzoa rheymatica* (aka XXNHF:00000:00000).

The aspects/implementations outlined here, and many others, will become readily apparent to those of ordinary skill in the art from this disclosure. Those of ordinary skill in the art will readily understand the versatility with which this disclosure may be applied.

In places where the description above refers to particular implementations of compositions and methods for detecting pathogenic protozoan, it should be readily apparent that a number of modifications may be made without departing from the spirit thereof and that these implementations may be alternatively applied. The accompanying CLAIMS are intended to cover such modifications as would fall within the true spirit and scope of the disclosure set forth in this document. The presently disclosed implementations are, therefore, to be considered in all respects as illustrative and not restrictive, the scope of the disclosure being indicated by the appended CLAIMS rather than the foregoing DESCRIPTION. All changes that come within the meaning of and range of equivalency of the CLAIMS are intended to be embraced therein.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

It is understood that the disclosed invention is not limited to the particular methodology, protocols and materials described as these can vary. It is also understood that the terminology used herein is for the purposes of describing particular embodiments only and is not intended to limit the scope of the present invention, which will be limited only by the appended claims.

The invention claimed is:

1. A method for determining whether a sample contains or has an increased likelihood of containing a pathogenic protozoan comprising:
   a) providing a vessel containing a reaction mixture, wherein the reaction mixture comprises at least one forward primer comprising SEQ ID NO: 6, at least one reverse primer comprising SEQ ID NO: 7, a nucleic acid target from the sample, and a pool of oligonucleotide probes selected from the group consisting of:
      i) oligonucleotide probes comprising the sequences of SEQ ID NO: 4, SEQ ID NO: 8, and SEQ ID NO: 9;
      ii) oligonucleotide probes comprising the sequences of SEQ ID NO: 10, SEQ ID NO: 12 and SEQ ID NO: 15;
      iii) oligonucleotide probes comprising the sequences of SEQ ID NO: 11, SEQ ID NO: 13 and SEQ ID NO: 14; and
      iv) oligonucleotide probes comprising the sequences of SEQ ID NO: 16 and SEQ ID NO: 17;
   wherein the reaction mixture is capable of amplifying, by a multiplex quantitative real time polymerase chain reaction (qPCR), a segment of the nucleic acid target to produce an amplicon; and wherein production of the amplicon is primed by the at least one forward primer and the at least one reverse primer;
   b) incubating the vessel under conditions allowing production of the amplicon if the sample contains the pathogenic protozoan; and
   c) determining that the sample contains the pathogenic protozoan or that the sample has an increased likelihood of containing the pathogenic protozoan if the amplicon is detected, or determining that the sample does not contain the pathogenic protozoan or that the sample does not have an increased likelihood of containing the pathogenic protozoan if the amplicon is not detected.

2. The method of claim 1, wherein the oligonucleotide probes further comprise a fluorophore and/or a quencher.

3. The method of claim 1, further comprising:
   (d) detecting fluorescence from the oligonucleotide probes in the reaction mixture; and
   (e) identifying the pathogenic protozoan using an alignment of a sequence of the oligonucleotide probes with a genomic sequence from the pathogenic protozoan.

4. The method of claim 3, wherein the alignment indicates at least 60%, at least 70%, at least 80%, at least 90%, or at least 95% identity between the sequence of the oligonucleotide probe and the genomic sequence.

5. The method of claim 1, wherein the pathogenic protozoan is selected from the group consisting of *Protomyxzoa* spp., *Sarcocystis* spp., *Cyclophora* spp., *Eimeria* spp., *Goussia* spp., *Entomoeba histolytica*, *Acanthamoeba castellanii*, *Balamuthia mandrillaris*, *Trichomonas* spp., *Trypanosoma* spp., *Leishmania* spp, *Pneumocystis pneumonia*, *Naegleria fowleri*, *Giardia intestinalis*, *Blastocystis hominis*, *Babesia microti*, *Cryptosporidium* spp., *Cyclospora cayetanensis*, *Toxoplasma gondii*, and *Theileria* spp.

6. The method of claim 5, wherein the *Protomyxzoa* spp. is *Protomyxzoa rheumatica*.

7. The method of claim 5, wherein the *Cryptosporidium* spp. is selected from *Cryptosporidium parvum*, *Cryptosporidium hominis*, *Cryptosporidium canis*, *Cryptosporidium felis*, *Cryptosporidium meleagridis*, and *Cryptosporidium muris*.

8. The method of claim 5, wherein the *Trichomonas* spp. is selected from *Trichomonas tenas, Trichomonas hominis,* and *Trichomonas vaginalis.*

9. The method of claim 5, wherein the *Trypanosoma* spp. is selected from *Trypanosoma gambiense, Trypanosoma rhodesiense, Trypanosoma cruzi* and *Trypanosoma brucei.*

10. The method of claim 5, wherein the *Leishmania* spp. is selected from *Leishmania donovani, Leishmania tropica,* and *Leishmania braziliensis.*

11. The method of claim 5, wherein the *Theileria* spp. is selected from *Theileria lawrenci* and *Theileria parva.*

12. A diagnostic kit used to determine whether a sample contains or has an increased likelihood of containing a pathogenic protozoan comprising:

at least one forward primer comprising SEQ ID NO: 6 and at least one reverse primer comprising SEQ ID NO: 7;

a pool of oligonucleotide probes selected from the group consisting of:

i) oligonucleotide probes comprising the sequences of SEQ ID NO: 4, SEQ ID NO: 8, and SEQ ID NO: 9;

ii) oligonucleotide probes comprising the sequences of SEQ ID NO: 10, SEQ ID NO: 12, and SEQ ID NO: 15;

iii) oligonucleotide probes comprising the sequences of SEQ ID NO: 11, SEQ ID NO: 13, and SEQ ID NO: 14; and iv) oligonucleotide probes comprising the sequences of SEQ ID NO: 16 and SEQ ID NO: 17;

wherein the oligonucleotide probes further comprise a fluorophore and/or a quencher;

an indication of a result of the presence of a nucleic acid from a pathogenic protozoan;

and instructions for using the kit;

wherein the kit utilizes multiplex quantitative real time PCR (qPCR).

* * * * *

SEQUENCE LISTING

```
<160> NUMBER OF SEQ ID NOS: 17

<210> SEQ ID NO 1
<211> LENGTH: 429
<212> TYPE: DNA
<213> ORGANISM: Protomyxzoa rheumatica

<400> SEQUENCE: 1
ccatgcatgt ctaagtataa gcacttatac agtgaaactg cgaatggctc attatatcag      60
ttatagttta tttgatagtc cctactactt ggataaccgt agtaattcta gagctaatac     120
atgcgctaac tcctgacctc acggaaagga tgtatttatt agatacaacc aaccttgttt     180
ggtgaatcat aataactgag cgaaccgcat gcttcggcgg cggtggttca ttcaagtttc     240
tgacctatca gctttcgatg gtagggtatt ggcctaccat ggcgttaacg ggtaacggag     300
aattagggtt cgattccgga gagggagcct gagagatggc taccacatcc aaggaaggca     360
```

-continued

```
gcaggcgcgt aaattaccca atcctgacac agggaggtag tgacaagaaa taacaatgcg    420
gagccttcg                                                            429

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
atggctcatt atatcagtta tagt                                           24

<210> SEQ ID NO 3
<211> LENGTH: 23
<212> TYPE: DNA
<213> ORGANISM: Artificial Sequence
<220> FEATURE:
<223> OTHER INFORMATION: PCR Primer

<400> SEQUENCE: 3
gttattatga ttcaccaaac aag                                            23

<210> SEQ ID NO 4
<211> LENGTH: 26
<212> TYPE: DNA
<213> ORGANISM: Artificial Sequence
<220> FEATURE:
<223> OTHER INFORMATION: PCR Probe

<400> SEQUENCE: 4
acatcctttc cgtgaggtca ggagtt                                         26

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
ccatgcatgt ctaagtata                                                 19

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
ccatgcatgt ctaagtataa gc                                             22

<210> SEQ ID NO 7
<211> LENGTH: 22
<212> TYPE: DNA
<213> ORGANISM: Artificial Sequence
<220> FEATURE:
<223> OTHER INFORMATION: PCR Primer

<400> SEQUENCE: 7
cagaaacttg aatgatctat cg                                             22

<210> SEQ ID NO 8
```

```
<211> LENGTH: 32
<212> TYPE: DNA
<213> ORGANISM: Artificial Sequence
<220> FEATURE:
<223> OTHER INFORMATION: PCR Probe

<400> SEQUENCE: 8
ggataaccgt agtaattctg gagctaatac at                            32

<210> SEQ ID NO 9
<211> LENGTH: 37
<212> TYPE: DNA
<213> ORGANISM: Artificial Sequence
<220> FEATURE:
<223> OTHER INFORMATION: PCR Probe

<400> SEQUENCE: 9
taaactrtaa ctgwtwtaat gagcywtycg cagttty                       37

<210> SEQ ID NO 10
<211> LENGTH: 26
<212> TYPE: DNA
<213> ORGANISM: Artificial Sequence
<220> FEATURE:
<223> OTHER INFORMATION: PCR Probe

<400> SEQUENCE: 10
ggagctaata catgatacag gacccg                                   26

<210> SEQ ID NO 11
<211> LENGTH: 38
<212> TYPE: DNA
<213> ORGANISM: Artificial Sequence
<220> FEATURE:
<223> OTHER INFORMATION: PCR Probe

<400> SEQUENCE: 11
gaatggctca ttawawcagt tayagtttat ttgatgat                      38

<210> SEQ ID NO 12
<211> LENGTH: 33
<212> TYPE: DNA
<213> ORGANISM: Artificial Sequence
<220> FEATURE:
<223> OTHER INFORMATION: PCR Probe

<400> SEQUENCE: 12
ctacgtggat aactgtagta attctagagc taa                           33

<210> SEQ ID NO 13
<211> LENGTH: 34
<212> TYPE: DNA
<213> ORGANISM: Artificial Sequence
<220> FEATURE:
<223> OTHER INFORMATION: PCR Probe

<400> SEQUENCE: 13
ttatttgatg gtttyytact tggataaccc gagt                          34

<210> SEQ ID NO 14
<211> LENGTH: 25
<212> TYPE: DNA
<213> ORGANISM: Artificial Sequence
<220> FEATURE:
<223> OTHER INFORMATION: PCR Probe

<400> SEQUENCE: 14
```

```
ctctggctaa tatacgctga agacc                                      25

<210> SEQ ID NO 15
<211> LENGTH: 34
<212> TYPE: DNA
<213> ORGANISM: Artificial Sequence
<220> FEATURE:
<223> OTHER INFORMATION: PCR Probe

<400> SEQUENCE: 15
tggataaccg yrgtaatwct rkrgctaaka catg                            34

<210> SEQ ID NO 16
<211> LENGTH: 33
<212> TYPE: DNA
<213> ORGANISM: Artificial Sequence
<220> FEATURE:
<223> OTHER INFORMATION: PCR Probe

<400> SEQUENCE: 16
gtgaaactgc gaatggctca ttatatcagt tat                             33

<210> SEQ ID NO 17
<211> LENGTH: 32
<212> TYPE: DNA
<213> ORGANISM: Artificial Sequence
<220> FEATURE:
<223> OTHER INFORMATION: PCR Probe

<400> SEQUENCE: 17
waydgygaaa ctgcgaatgg ctcattawaw ca                              32
```